United States Patent
Jen et al.

(10) Patent No.: US 12,390,517 B2
(45) Date of Patent: Aug. 19, 2025

(54) COMPOSITIONS, METHODS AND USES FOR ELICITING AN IMMUNE RESPONSE

(71) Applicant: Griffith University, Nathan (AU)

(72) Inventors: Freda E.-C. Jen, Nathan (AU); Kate Seib, Nathan (AU); Evgeny Semchenko, Nathan (AU); Michael Jennings, Nathan (AU)

(73) Assignee: GRIFFITH UNIVERSITY, Nathan (AU)

( * ) Notice: Subject to any disclaimer, the term of this patent is extended or adjusted under 35 U.S.C. 154(b) by 996 days.

(21) Appl. No.: 17/416,271

(22) PCT Filed: Dec. 20, 2019

(86) PCT No.: PCT/AU2019/051418
§ 371 (c)(1),
(2) Date: Jun. 18, 2021

(87) PCT Pub. No.: WO2020/124159
PCT Pub. Date: Jun. 25, 2020

(65) Prior Publication Data
US 2022/0062402 A1    Mar. 3, 2022

(30) Foreign Application Priority Data
Dec. 21, 2018    (AU) ................................ 2018904887

(51) Int. Cl.
*A61K 39/095* (2006.01)
*A61K 39/00* (2006.01)
*C12N 15/86* (2006.01)

(52) U.S. Cl.
CPC ............ *A61K 39/095* (2013.01); *C12N 15/86* (2013.01); *A61K 2039/55566* (2013.01); *A61K 2039/55577* (2013.01); *A61K 2039/575* (2013.01); *A61K 2039/6037* (2013.01); *A61K 2039/70* (2013.01)

(58) Field of Classification Search
None
See application file for complete search history.

(56) References Cited

U.S. PATENT DOCUMENTS

| | | |
|---|---|---|
| 2006/0008476 A1 | 1/2006 | Pizza |
| 2012/0052092 A1 | 3/2012 | Exley et al. |
| 2012/0070457 A1 | 3/2012 | Daugherty |

FOREIGN PATENT DOCUMENTS

| | | |
|---|---|---|
| WO | WO 1992/005266 | 4/1992 |
| WO | WO 1995/030763 | 11/1995 |
| WO | WO 1996/037626 | 11/1996 |
| WO | WO 2002/079243 A2 | 10/2002 |
| WO | WO 2017/123886 A1 | 7/2017 |
| WO | WO 2018/169926 A1 | 9/2018 |

OTHER PUBLICATIONS

Altschul et al., "Gapped BLAST and PSI-BLAST: a new generation of protein database search programs," Nucleic Acids Research, 1997, vol. 25, No. 17, pp. 3389-3402.
Alves et al., "Bacterial Nanobioreactors-Directing Enzyme Packaging into Bacterial Outer Membrane Vesicles," ACS Applied Material & Interfaces, 2015, 7, pp. 24963-24972.
Bos et al., "Involvement of Neissseria meningitidis Lipoprotein GNA2091 in the Assembly of Subset of Outer Membrane Proteins," The Journal of Biological Chemistry, May 30, 2014, vol. 289, No. 22 pp. 5602-15610.
Brandler et al., "A recombinant measles vaccine expressing chikungunya virus-like particles is strongly immunogenic and protects mice from lethal challenge with chikungunya virus," Vaccine 31, 2013, pp. 3718-3725.
Brot et al., "The Thioredoxin Domain of Neisseria gonorrhoeae PilB Can Use Electrons from DsbD to Reduce Downstream Methionine Sulfoxide Reductases," The Journal of Biological Chemistry, Oct. 27, 2006, vol. 281, No. 43, pp. 32668-32675.
Cantarella et al., "Recombinant measles virus-HPV vaccine candidates for prevention of cervical carcinoma," Vaccine 27, 2009, pp. 3385-3390.
Choi et al., "Viral vectors for vaccine applications," Clinical and Experimental Vaccine Research, 2013, 2, pp. 97-105.
Coler et al., "Development and Characterization of Synthetic Glucopyranosyl Lipid Adjuvnt System as a Vaccine Adjuvant," Plos ONE, 2011, vol. 6, Issue 1, pp. 1-12.
Craig et al., "The potential impact of vaccination on the prevalence of gonorhea," Vaccine33, 2015, pp. 4520-4525.
Devereux t al., "A comprhenive analysis programs for the VAX," Nucleic Acids Research, 1984, vol. 12. No. 1. pp. 387-395.
Diethelm-Okita et al., "Universal Epitopes for Human CD4+ Cells on Tetanus and Diphtheria Toxins," The Journal of Infectious Diseases, 2000, 181, 1001-1009.
Edwards et al.,"Is gonococcal disease preventable? The importance of understandingimmunity and pathogenesis in vaccine development," Critical Reviews in Microbiology, 2016, 42:6, 928-941.

(Continued)

*Primary Examiner* — Brian Gangle
(74) *Attorney, Agent, or Firm* — Knobbe, Martens, Olson & Bear, LLP

(57) ABSTRACT

This invention relates generally to polynucleotides, polypeptides, compositions, methods and uses for eliciting an immune response to *Neisseria*, methods for immunizing a subject against a *Neisseria* infection, and methods for preventing and/or treating a *Neisseria* infection in a subject. More particularly, the invention relates to antigenic *Neisseria* polypeptides and encoding polynucleotides, and related uses and methods, including use for preparing compositions and medicaments for eliciting an immune response to *Neisseria*, for immunizing a subject against a *Neisseria* infection, and for preventing and/or treating a *Neisseria* infection in a subject. The invention also relates to methods for producing therapeutic anti-*Neisseria* antigen-binding molecules, and therapeutic uses of those antigen-binding molecules.

27 Claims, 6 Drawing Sheets
Specification includes a Sequence Listing.

(56) References Cited

OTHER PUBLICATIONS

Ezraty et al.,"Methionine sulfoxide reductases in prokaryotes," Biochimica et Biophysica Acta 1703, 2005, pp. 221-229.
Farris et al., "Micro- and nanoparticulates for DNA vaccine delivery," Experimental Biology and Medicine, 2016, 241: 919-929.
Garçon et al., "From discovery to licensure, the Adjuvant System story," Human Vaccines & Immunotherapeutics, 2017, vol. 13, No. 1, pp. 19-33.
GenBank, "Neisseria gonorrhoeae 1291 supercont1.3 genomic scaffold, whole genome shotgun sequence," GenBank: DS999919.1, 2016.
Genpept, "Peptide methionine sulfoxide reductase msrA/msrB [Neisseria gonorrhoeae 1291]," GenBank: EEH61172.1, 2016.
Gerritzen et al., "Bioengineering bacterial outer membrane vesicles as vaccine platform," Biotechnology Advances 35, 2017, pp. 565-574.
Gilbert, Sarah C., "Clinical development of Modified Vaccinia virus Ankara vaccines," Vaccine 31, 2013, pp. 4241-4246.
Greenstein et al., "A universal T cell epitope-containing peptide from hepatitis B surface antigen can enhance antibody specific for HIV gp120.," The Journal of Immunology, Jun. 15, 1992, vol. 148, No. 12, pp. 3970-3977.
Gregory et al., "Vaccine delivery using nanoparticles," Frontiers in Cellular and Infection Microbiology, Mar. 2013, vol. 3, Article 13, pp. 1-13.
Humphreys et al., "Novel viral vectors in infectious diseases," Immunology, The Journal of cells, molecules, systems and technologies, 2017, 153, pp. 1-9.
Ieva et a., "CrgA Is an Inducible LysR-Type Regulator of Neisseria meningitidis, Acting both as a Repressor and as an Activator of Gene Transcription," Journal of Bacteriology, May 2005, vol. 187, No. 10, pp. 3421-3430.
Jerse, Ann E., "Experimental Gonococcal Genital Tract Infection and Opacity Protein Expression in Estradiol-Treated Mice," Infection and Immunity, Nov. 1999, vol. 67, No. 11, pp. 5699-5708.
Jerse, et al., "Vaccines against gonorrhea: Current status and future challenges," Vaccine 32, 2014, pp. 1579-1587.
Joshi et al., "Targeting tumor antigens to dendritic cells using particulate carriers," Journal of Controlled Release 161, 2012, pp. 25-37.
Krogh et al., "Predicting Transmembrane Protein Topology with a Hidden Markov Model: Aplication to Complete Genomes," J. Mol. Biol., 2001, 305, pp. 567-580.
Lerner Richard A., "Combinatorial antibody libraries: new advances, new immunologicalIinsights," Department of Cell and Molecular Biology, The Scripps Research Institute, Aug. 2016, vol. 16, pp. 498-508.
Lowther e al., "The mirrored methionine sulfoxide reductases of Neisseria gonorrhoeae pilB," Nature Sructural Biology, May 2002, vol. 9, No. 5, pp. 348-352.
Lundstrom, Kenneth, "Alphavirus Vectors in Vaccine Development," Journal of Vaccines & Vaccination, 2012, vol. 3, Issue 3, pp. 1-8.
McQuillen et al., "Complement-Mediated Bacterial Killing Assays," Methods in Enxymology, 1994, vol. 236, pp. 137-147.
Naso et al., "Adeno-Associated Virus (AAV) as a Vector for Gene Therapy," BioDrugs, 2017, 31:317-334.
Packiam et al., "Mouse Strain-Dependent Differeencs in Susceptibility to Neisseria gonorrhoeae Infection and Induction of Innate Immune Responses," Infection and Immunity, Jan. 2010, vol. v78, No. 1, pp. 433-440.
Petousis-Harris et al., "Effectiveness of a group B outer membrane vesicle meningococcal vaccine against gonorrhoea in New Zealand: a retrospective case-control study," Lancet, Sep. 30, 2017, vol. 390, pp. 1603-1610.
Pira et al., "High Throughput T Epitope Mapping and Vaccine Development," Journal f Biomedecine and Biotechnology, 2010 vol. 2010, Article ID 325720, pp. 1-12.

Power et al., "The Phase-Variable Allele of the Pilus Glycosylation Gene pglA Is Not Strongly Associate with Strains of Neisseria gonorrhoeae Isolated from Patients with Disseminated Gonococcal Infection," Infection and Immunity, Jun. 2007, vol. 75, No. 6, pp. 3202-3204.
Rice et al., "Neisseria gonorrhoeae: Drug Resistance, Mouse Models, and Vaccine Development," Annual Review of Microbiology, 2017, vol. 71, pp. 665-686.
Romero-Steiner et al., "Standardization of an Opsonophagocytic Assay for the Measurement of Functional Antibody Activity against *Streptococcus pneumoniae* Using Differentiated HL-60 Cells," Clinical and Diagnostic Laboratory Immunology, Jul. 1997, vol. 4, No. 4, pp. 415-422.
Seib et al., "Influence of serogroup B meningococcal vaccine antigens on growth and survival of the meningococcus in vitro and in ex vivo and in vivo models of infection," Vaccine 28, 2010, pp. 2416-2427.
Semchenko et al., "MetQ of Neisseria gonorrhoeae Is a Surface-Expressed Antigen ThatElicits Bactericidal and Functional Blocking Antibodies," Infection and Immunity, Feb. 2017, vol. 85, Issue 2, pp. 1-17.
Steichen et al., "Gonococcal Cervicitis: A Role for Biofilm in Pathogenesis," Joural of Infectious Diseases, Dec. 15, 2008, 198, pp. 1856-1861.
Steinhagen et al., "TLR-based immune adjuvants," Vaccine 29, 2011, pp. 3341-3355.
Tan et al.,"Outer Membrane Vesicles: Current Status and Future Direction of These Novel Vaccine Adjuvants," Frontiers in Microbiology, Apr. 2018, vol. 9, Article 783, pp. 1-12.
Tomusange et al., "Engineering human rhinovirus serotype-A1 as a vaccine vector," Virus Research 203, 2015, pp. 72-76.
UniProtKB/Swiss-Prot., P14930, Peptide methionine sulfoxide reductase MsrA/MsrB, 1990.
Ura et al., "Developments in Viral Vector-Based Vaccines," Vaccines, 2014, 2, pp. 624-641.
Vincent et al., "Biological feasibility and importance of a gonorrhea vaccine for global public health," Vaccine 37, 2019, pp. 7419-7426.
Virji et al.,"Opc- and pilus-dependent interactions of meningococci with human endothelial cells: molecular mechanisms and modulation by surface polysaccharides," Molecular Microbiology, 1995, 18(4), pp. 741-754.
Wagner et al.,"Liposome Technology for Industrial Purposes," Journal of Drug Delivery, vol. 2011, Article ID 591325, pp. 1-9.
Weissbach t al., "Methionine sulfoxide reductases: history and cellular role in protecting against oxidative damage," Biochimica et Biophysica Acta 1703, 2005, pp. 203-212.
Weyand, Nathan J., "Neisseria models of infection and persistence in the upper respiratory tract," Pathogens and Disease, 2017, vol. 75, No. 3, pp. 1-13.
Yi et al., "Development and Evaluation of an Improved Mouse Model of Meningococcal Colonization," Infection and Immunity, Apr. 2003, vol. 71, No. 4, pp. 1849-1855.
Yu et al., "Microfluidic Methods for Production of Lipsomes," Methods in Enzymology, 2009, vol. 465, pp. 129-140.
Zhang et al.,"Adenoviral vector-based strategies against infectious disease and cancer," Human Vaccines & Immunotherapeutics, 2016, vol. 12, No. 8, pp. 2064-2074.
Zhao et al., "Nanoparticle vaccines," Vaccine 32, 2014, pp. 327-337.
Boschi-Muller, S., Molecular Mechanisms of the Methionine Sulfoxide Reductase System from Neisseria meningitidis, Antioxidants, vol. 7, No. 131, 11 pages, 2018.
Brot et al., The Thioredoxin Domain of Neisseria gonorrhoeae PilB Can Use Electrons from DsbD to Reduce Downstream Methionine Sulfoxide Reductases, The Journal of Biological Chemistry, vol. 281, No. 43, pp. 32668-32675, 2006.
Lowther et al., Thiol-disulfide exchange is involved in the catalytic mechanism of peptide methionine sulfoxide reductase, PNAS, vol. 97, No. 12, pp. 6463-6468, 2000.
Lowther et al., The mirriored methionione sulfoxide reductases of Neisseria gonorrhoeae pilB, Nature Structural Biology, vol. 9, No. 5, pp. 348-352, 2002.

(56) References Cited

OTHER PUBLICATIONS

Peptide methionine sulfoxide reductase msrA/msrB [Neisseria gonorrhoeae 1291] GenBank: EEH61172.1, 2016.

Full=Peptide methionine sulfoxide reductase MsrA/MsrB UniProtKB/Swiss-Prot: P14930.2, 1990.

Wu et al., The N-terminal Domain of PILB from Neisseria meningitidis is a Disulfide Reductase That Can Recycle Methionine Sulfoxide Reductases, The Journal of Biological Chemistry, vol. 280, No. 13, pp. 12344-12350, 2005.

Quintemet et al., Formation of the Complex between DsbD and PilB N-Terminal Domains from Neisseria meningitidis Necessitates an Adaptability of nDsbD, Structure, vol. 17, pp. 1024-1033, 2009.

UniProt database protein Q5F571 (Q5F571_NEIG1), Version 100, dated Feb. 28, 2018, Retrieved from: https://rest.uniprot.org/unisave/Q5F571?format=txt&versions=100.

UniProt database protein Q5F571 (Q5F571_NEIG1), Version 98, dated Feb. 28, 2018, Retrieved from: https://rest.uniprot.org/unisave/Q5F571?format=txt&versions=100.

Freda E.-C. et al., The Neisseria gonorrhoeae Methionine Sulfoxide Reductase (MsrA/B) Is a Surface Exposed, Immunogenic, Vaccine Candidate, Frontiers in Immunology, vol. 10, Article 137, pp. 1-9, 2019.

Skaar et al., The outer membrane localization of the Neisseria gonorrhoeae MsrA/B is involved in survival against reactive oxygen species, Proceedings of the National Academy of Sciences of the United States of America, vol. 99, No. 15, pp. 10108-10113, 2002.

International Search Report mailed on Mar. 6, 2020 in International Application No. PCT/AU2019/051418.

Written Opinion mailed on Mar. 6, 2020 in International Application No. PCT/AU2019/051418.

International Preliminary Report on Patentability mailed on Jul. 1, 2021 in International Application No. PCT/AU2019/051418.

A.

C.

SEQUENCE LISTING

```
<160> NUMBER OF SEQ ID NOS: 40

<210> SEQ ID NO 1
<211> LENGTH: 522
<212> TYPE: PRT
<213> ORGANISM: Neisseria gonorrhoeae

<400> SEQUENCE: 1

Met Lys His Arg Thr Phe Phe Ser Leu Cys Ala Lys Phe Gly Cys Leu
1               5                   10                  15

Leu Ala Leu Gly Ala Cys Ser Pro Lys Ile Val Asp Ala Gly Thr Ala
            20                  25                  30

Thr Val Pro His Thr Leu Ser Thr Leu Lys Thr Ala Asp Asn Arg Pro
        35                  40                  45

Ala Ser Val Tyr Leu Lys Lys Asp Lys Pro Thr Leu Ile Lys Phe Trp
    50                  55                  60

Ala Ser Trp Cys Pro Leu Cys Leu Ser Glu Leu Gly Gln Ala Glu Lys
65                  70                  75                  80

Trp Ala Gln Asp Ala Lys Phe Ser Ser Ala Asn Leu Ile Thr Val Ala
                85                  90                  95

Ser Pro Gly Phe Leu His Glu Lys Lys Asp Gly Glu Phe Gln Lys Trp
            100                 105                 110

Tyr Ala Gly Leu Asn Tyr Pro Lys Leu Pro Val Val Thr Asp Asn Gly
        115                 120                 125

Gly Thr Ile Ala Gln Asn Leu Asn Ile Ser Val Tyr Pro Ser Trp Ala
    130                 135                 140

Leu Ile Gly Lys Asp Gly Asp Val Gln Arg Ile Val Lys Gly Ser Ile
145                 150                 155                 160
```

```
Asn Glu Ala Gln Ala Leu Ala Leu Ile Arg Asn Pro Asn Ala Asp Leu
            165                 170                 175
Gly Ser Leu Lys His Ser Phe Tyr Lys Pro Asp Thr Gln Lys Lys Asp
        180                 185                 190
Ser Ala Ile Met Asn Thr Arg Thr Ile Tyr Leu Ala Gly Gly Cys Phe
    195                 200                 205
Trp Gly Leu Glu Ala Tyr Phe Gln Arg Ile Asp Gly Val Val Asp Ala
210                 215                 220
Val Ser Gly Tyr Ala Asn Gly Asn Thr Glu Asn Pro Ser Tyr Glu Asp
225                 230                 235                 240
Val Ser Tyr Arg His Thr Gly His Ala Glu Thr Val Lys Val Thr Tyr
                245                 250                 255
Asp Ala Asp Lys Leu Ser Leu Asp Asp Ile Leu Gln Tyr Tyr Phe Arg
            260                 265                 270
Val Val Asp Pro Thr Ser Leu Asn Lys Gln Gly Asn Asp Thr Gly Thr
        275                 280                 285
Gln Tyr Arg Ser Gly Val Tyr Tyr Thr Asp Pro Ala Glu Lys Ala Val
    290                 295                 300
Ile Ala Ala Ala Leu Lys Arg Glu Gln Gln Lys Tyr Gln Leu Pro Leu
305                 310                 315                 320
Val Val Glu Asn Glu Pro Leu Lys Asn Phe Tyr Asp Ala Glu Glu Tyr
                325                 330                 335
His Gln Asp Tyr Leu Ile Lys Asn Pro Asn Gly Tyr Cys His Ile Asp
            340                 345                 350
Ile Arg Lys Ala Asp Glu Pro Leu Pro Gly Lys Thr Lys Ala Ala Pro
        355                 360                 365
Gln Gly Lys Gly Phe Asp Ala Ala Thr Tyr Lys Lys Pro Ser Asp Ala
    370                 375                 380
Glu Leu Lys Arg Thr Leu Thr Glu Glu Gln Tyr Gln Val Thr Gln Asn
385                 390                 395                 400
Ser Ala Thr Glu Tyr Ala Phe Ser His Glu Tyr Asp His Leu Phe Lys
                405                 410                 415
Pro Gly Ile Tyr Val Asp Val Val Ser Gly Glu Pro Leu Phe Ser Ser
            420                 425                 430
Ala Asp Lys Tyr Asp Ser Gly Cys Gly Trp Pro Ser Phe Thr Arg Pro
        435                 440                 445
Ile Asp Ala Lys Ser Val Thr Glu His Asp Asp Phe Ser Phe Asn Met
    450                 455                 460
Arg Arg Thr Glu Val Arg Ser Arg Ala Ala Asp Ser His Leu Gly His
465                 470                 475                 480
Val Phe Pro Asp Gly Pro Arg Asp Lys Gly Gly Leu Arg Tyr Cys Ile
                485                 490                 495
Asn Gly Ala Ser Leu Lys Phe Ile Pro Leu Glu Gln Met Asp Ala Ala
            500                 505                 510
Gly Tyr Gly Ala Leu Lys Gly Lys Val Lys
        515                 520

<210> SEQ ID NO 2
<211> LENGTH: 182
<212> TYPE: PRT
<213> ORGANISM: Neisseria gonorrhoeae

<400> SEQUENCE: 2

His Ser Phe Tyr Lys Pro Asp Thr Gln Lys Lys Asp Ser Ala Ile Met
1               5                   10                  15
```

```
Asn Thr Arg Thr Ile Tyr Leu Ala Gly Gly Cys Phe Trp Gly Leu Glu
            20                  25                  30

Ala Tyr Phe Gln Arg Ile Asp Gly Val Val Asp Ala Val Ser Gly Tyr
        35                  40                  45

Ala Asn Gly Asn Thr Glu Asn Pro Ser Tyr Glu Asp Val Ser Tyr Arg
 50                  55                  60

His Thr Gly His Ala Glu Thr Val Lys Val Thr Tyr Asp Ala Asp Lys
 65                  70                  75                  80

Leu Ser Leu Asp Asp Ile Leu Gln Tyr Tyr Phe Arg Val Val Asp Pro
                85                  90                  95

Thr Ser Leu Asn Lys Gln Gly Asn Asp Thr Gly Thr Gln Tyr Arg Ser
            100                 105                 110

Gly Val Tyr Tyr Thr Asp Pro Ala Glu Lys Ala Val Ile Ala Ala Ala
                115                 120                 125

Leu Lys Arg Glu Gln Gln Lys Tyr Gln Leu Pro Leu Val Val Glu Asn
            130                 135                 140

Glu Pro Leu Lys Asn Phe Tyr Asp Ala Glu Glu Tyr His Gln Asp Tyr
145                 150                 155                 160

Leu Ile Lys Asn Pro Asn Gly Tyr Cys His Ile Asp Ile Arg Lys Ala
                165                 170                 175

Asp Glu Pro Leu Pro Gly
            180

<210> SEQ ID NO 3
<211> LENGTH: 156
<212> TYPE: PRT
<213> ORGANISM: Neisseria gonorrhoeae

<400> SEQUENCE: 3

Arg Thr Ile Tyr Leu Ala Gly Gly Cys Phe Trp Gly Leu Glu Ala Tyr
 1               5                  10                  15

Phe Gln Arg Ile Asp Gly Val Val Asp Ala Val Ser Gly Tyr Ala Asn
            20                  25                  30

Gly Asn Thr Glu Asn Pro Ser Tyr Glu Asp Val Ser Tyr Arg His Thr
        35                  40                  45

Gly His Ala Glu Thr Val Lys Val Thr Tyr Asp Ala Asp Lys Leu Ser
 50                  55                  60

Leu Asp Asp Ile Leu Gln Tyr Tyr Phe Arg Val Val Asp Pro Thr Ser
65                  70                  75                  80

Leu Asn Lys Gln Gly Asn Asp Thr Gly Thr Gln Tyr Arg Ser Gly Val
                85                  90                  95

Tyr Tyr Thr Asp Pro Ala Glu Lys Ala Val Ile Ala Ala Ala Leu Lys
            100                 105                 110

Arg Glu Gln Gln Lys Tyr Gln Leu Pro Leu Val Val Glu Asn Glu Pro
        115                 120                 125

Leu Lys Asn Phe Tyr Asp Ala Glu Glu Tyr His Gln Asp Tyr Leu Ile
    130                 135                 140

Lys Asn Pro Asn Gly Tyr Cys His Ile Asp Ile Arg
145                 150                 155

<210> SEQ ID NO 4
<211> LENGTH: 148
<212> TYPE: PRT
<213> ORGANISM: Neisseria gonorrhoeae

<400> SEQUENCE: 4
```

```
Ala Ala Thr Tyr Lys Lys Pro Ser Asp Ala Glu Leu Lys Arg Thr Leu
1               5                   10                  15

Thr Glu Glu Gln Tyr Gln Val Thr Gln Asn Ser Ala Thr Glu Tyr Ala
            20                  25                  30

Phe Ser His Glu Tyr Asp His Leu Phe Lys Pro Gly Ile Tyr Val Asp
        35                  40                  45

Val Val Ser Gly Glu Pro Leu Phe Ser Ala Asp Lys Tyr Asp Ser
    50                  55                  60

Gly Cys Gly Trp Pro Ser Phe Thr Arg Pro Ile Asp Ala Lys Ser Val
65                  70                  75                  80

Thr Glu His Asp Asp Phe Ser Phe Asn Met Arg Arg Thr Glu Val Arg
            85                  90                  95

Ser Arg Ala Ala Asp Ser His Leu Gly His Val Phe Pro Asp Gly Pro
        100                 105                 110

Arg Asp Lys Gly Gly Leu Arg Tyr Cys Ile Asn Gly Ala Ser Leu Lys
            115                 120                 125

Phe Ile Pro Leu Glu Gln Met Asp Ala Ala Gly Tyr Gly Ala Leu Lys
130                 135                 140

Gly Lys Val Lys
145

<210> SEQ ID NO 5
<211> LENGTH: 124
<212> TYPE: PRT
<213> ORGANISM: Neisseria gonorrhoeae

<400> SEQUENCE: 5

Asp Ala Glu Leu Lys Arg Thr Leu Thr Glu Glu Gln Tyr Gln Val Thr
1               5                   10                  15

Gln Asn Ser Ala Thr Glu Tyr Ala Phe Ser His Glu Tyr Asp His Leu
            20                  25                  30

Phe Lys Pro Gly Ile Tyr Val Asp Val Val Ser Gly Glu Pro Leu Phe
        35                  40                  45

Ser Ser Ala Asp Lys Tyr Asp Ser Gly Cys Gly Trp Pro Ser Phe Thr
50                  55                  60

Arg Pro Ile Asp Ala Lys Ser Val Thr Glu His Asp Asp Phe Ser Phe
65                  70                  75                  80

Asn Met Arg Arg Thr Glu Val Arg Ser Arg Ala Ala Asp Ser His Leu
            85                  90                  95

Gly His Val Phe Pro Asp Gly Pro Arg Asp Lys Gly Gly Leu Arg Tyr
        100                 105                 110

Cys Ile Asn Gly Ala Ser Leu Lys Phe Ile Pro Leu
        115                 120

<210> SEQ ID NO 6
<211> LENGTH: 158
<212> TYPE: PRT
<213> ORGANISM: Neisseria gonorrhoeae

<400> SEQUENCE: 6

Leu Ala Leu Gly Ala Cys Ser Pro Lys Ile Val Asp Ala Gly Thr Ala
1               5                   10                  15

Thr Val Pro His Thr Leu Ser Thr Leu Lys Thr Ala Asp Asn Arg Pro
            20                  25                  30

Ala Ser Val Tyr Leu Lys Lys Asp Lys Pro Thr Leu Ile Lys Phe Trp
        35                  40                  45
```

Ala Ser Trp Cys Pro Leu Cys Leu Ser Glu Leu Gly Gln Ala Glu Lys
 50                  55                  60

Trp Ala Gln Asp Ala Lys Phe Ser Ser Ala Asn Leu Ile Thr Val Ala
 65                  70                  75                  80

Ser Pro Gly Phe Leu His Glu Lys Lys Asp Gly Glu Phe Gln Lys Trp
                 85                  90                  95

Tyr Ala Gly Leu Asn Tyr Pro Lys Leu Pro Val Val Thr Asp Asn Gly
                100                 105                 110

Gly Thr Ile Ala Gln Asn Leu Asn Ile Ser Val Tyr Pro Ser Trp Ala
                115                 120                 125

Leu Ile Gly Lys Asp Gly Asp Val Gln Arg Ile Val Lys Gly Ser Ile
130                 135                 140

Asn Glu Ala Gln Ala Leu Ala Leu Ile Arg Asn Pro Asn Ala
145                 150                 155

<210> SEQ ID NO 7
<211> LENGTH: 491
<212> TYPE: PRT
<213> ORGANISM: Neisseria gonorrhoeae

<400> SEQUENCE: 7

Ala Thr Val Pro His Thr Leu Ser Thr Leu Lys Thr Ala Asp Asn Arg
1               5                   10                  15

Pro Ala Ser Val Tyr Leu Lys Lys Asp Lys Pro Thr Leu Ile Lys Phe
                20                  25                  30

Trp Ala Ser Trp Cys Pro Leu Cys Leu Ser Glu Leu Gly Gln Ala Glu
                35                  40                  45

Lys Trp Ala Gln Asp Ala Lys Phe Ser Ser Ala Asn Leu Ile Thr Val
 50                  55                  60

Ala Ser Pro Gly Phe Leu His Glu Lys Lys Asp Gly Glu Phe Gln Lys
 65                  70                  75                  80

Trp Tyr Ala Gly Leu Asn Tyr Pro Lys Leu Pro Val Val Thr Asp Asn
                85                  90                  95

Gly Gly Thr Ile Ala Gln Asn Leu Asn Ile Ser Val Tyr Pro Ser Trp
                100                 105                 110

Ala Leu Ile Gly Lys Asp Gly Asp Val Gln Arg Ile Val Lys Gly Ser
                115                 120                 125

Ile Asn Glu Ala Gln Ala Leu Ala Leu Ile Arg Asn Pro Asn Ala Asp
130                 135                 140

Leu Gly Ser Leu Lys His Ser Phe Tyr Lys Pro Asp Thr Gln Lys Lys
145                 150                 155                 160

Asp Ser Ala Ile Met Asn Thr Arg Thr Ile Tyr Leu Ala Gly Gly Cys
                165                 170                 175

Phe Trp Gly Leu Glu Ala Tyr Phe Gln Arg Ile Asp Gly Val Val Asp
                180                 185                 190

Ala Val Ser Gly Tyr Ala Asn Gly Asn Thr Glu Asn Pro Ser Tyr Glu
                195                 200                 205

Asp Val Ser Tyr Arg His Thr Gly His Ala Glu Thr Val Lys Val Thr
                210                 215                 220

Tyr Asp Ala Asp Lys Leu Ser Leu Asp Ile Leu Gln Tyr Tyr Phe
225                 230                 235                 240

Arg Val Val Asp Pro Thr Ser Leu Asn Lys Gln Gly Asn Asp Thr Gly
                245                 250                 255

Thr Gln Tyr Arg Ser Gly Val Tyr Tyr Thr Asp Pro Ala Glu Lys Ala

```
                260                 265                 270
Val Ile Ala Ala Leu Lys Arg Glu Gln Gln Lys Tyr Gln Leu Pro
            275                 280                 285

Leu Val Val Glu Asn Glu Pro Leu Lys Asn Phe Tyr Asp Ala Glu
            290                 295                 300

Tyr His Gln Asp Tyr Leu Ile Lys Asn Pro Asn Gly Tyr Cys His Ile
305                 310                 315                 320

Asp Ile Arg Lys Ala Asp Glu Pro Leu Pro Gly Lys Thr Lys Ala Ala
                325                 330                 335

Pro Gln Gly Lys Gly Phe Asp Ala Ala Thr Tyr Lys Lys Pro Ser Asp
                340                 345                 350

Ala Glu Leu Lys Arg Thr Leu Thr Glu Glu Gln Tyr Gln Val Thr Gln
            355                 360                 365

Asn Ser Ala Thr Glu Tyr Ala Phe Ser His Glu Tyr Asp His Leu Phe
            370                 375                 380

Lys Pro Gly Ile Tyr Val Asp Val Val Ser Gly Glu Pro Leu Phe Ser
385                 390                 395                 400

Ser Ala Asp Lys Tyr Asp Ser Gly Cys Gly Trp Pro Ser Phe Thr Arg
                405                 410                 415

Pro Ile Asp Ala Lys Ser Val Thr Glu His Asp Asp Phe Ser Phe Asn
                420                 425                 430

Met Arg Arg Thr Glu Val Arg Ser Arg Ala Ala Asp Ser His Leu Gly
            435                 440                 445

His Val Phe Pro Asp Gly Pro Arg Asp Lys Gly Gly Leu Arg Tyr Cys
            450                 455                 460

Ile Asn Gly Ala Ser Leu Lys Phe Ile Pro Leu Glu Gln Met Asp Ala
465                 470                 475                 480

Ala Gly Tyr Gly Ala Leu Lys Gly Lys Val Lys
                485                 490

<210> SEQ ID NO 8
<211> LENGTH: 493
<212> TYPE: PRT
<213> ORGANISM: Neisseria gonorrhoeae

<400> SEQUENCE: 8

Gly Thr Ala Thr Val Pro His Thr Leu Ser Thr Leu Lys Thr Ala Asp
1               5                   10                  15

Asn Arg Pro Ala Ser Val Tyr Leu Lys Lys Asp Lys Pro Thr Leu Ile
                20                  25                  30

Lys Phe Trp Ala Ser Trp Cys Pro Leu Cys Leu Ser Glu Leu Gly Gln
            35                  40                  45

Ala Glu Lys Trp Ala Gln Asp Ala Lys Phe Ser Ser Ala Asn Leu Ile
        50                  55                  60

Thr Val Ala Ser Pro Gly Phe Leu His Glu Lys Lys Asp Gly Glu Phe
65                  70                  75                  80

Gln Lys Trp Tyr Ala Gly Leu Asn Tyr Pro Lys Leu Pro Val Val Thr
                85                  90                  95

Asp Asn Gly Gly Thr Ile Ala Gln Asn Leu Asn Ile Ser Val Tyr Pro
                100                 105                 110

Ser Trp Ala Leu Ile Gly Lys Asp Gly Asp Val Gln Arg Ile Val Lys
            115                 120                 125

Gly Ser Ile Asn Glu Ala Gln Ala Leu Ala Leu Ile Arg Asn Pro Asn
        130                 135                 140
```

```
Ala Asp Leu Gly Ser Leu Lys His Ser Phe Tyr Lys Pro Asp Thr Gln
145                 150                 155                 160

Lys Lys Asp Ser Ala Ile Met Asn Thr Arg Thr Ile Tyr Leu Ala Gly
            165                 170                 175

Gly Cys Phe Trp Gly Leu Glu Ala Tyr Phe Gln Arg Ile Asp Gly Val
        180                 185                 190

Val Asp Ala Val Ser Gly Tyr Ala Asn Gly Asn Thr Glu Asn Pro Ser
    195                 200                 205

Tyr Glu Asp Val Ser Tyr Arg His Thr Gly His Ala Glu Thr Val Lys
210                 215                 220

Val Thr Tyr Asp Ala Asp Lys Leu Ser Leu Asp Asp Ile Leu Gln Tyr
225                 230                 235                 240

Tyr Phe Arg Val Val Asp Pro Thr Ser Leu Asn Lys Gln Gly Asn Asp
                245                 250                 255

Thr Gly Thr Gln Tyr Arg Ser Gly Val Tyr Tyr Thr Asp Pro Ala Glu
            260                 265                 270

Lys Ala Val Ile Ala Ala Leu Lys Arg Glu Gln Gln Lys Tyr Gln
        275                 280                 285

Leu Pro Leu Val Val Glu Asn Glu Pro Leu Lys Asn Phe Tyr Asp Ala
290                 295                 300

Glu Glu Tyr His Gln Asp Tyr Leu Ile Lys Asn Pro Asn Gly Tyr Cys
305                 310                 315                 320

His Ile Asp Ile Arg Lys Ala Asp Glu Pro Leu Pro Gly Lys Thr Lys
                325                 330                 335

Ala Ala Pro Gln Gly Lys Gly Phe Asp Ala Thr Tyr Lys Lys Pro
        340                 345                 350

Ser Asp Ala Glu Leu Lys Arg Thr Leu Thr Glu Glu Gln Tyr Gln Val
    355                 360                 365

Thr Gln Asn Ser Ala Thr Glu Tyr Ala Phe Ser His Glu Tyr Asp His
370                 375                 380

Leu Phe Lys Pro Gly Ile Tyr Val Asp Val Ser Gly Glu Pro Leu
385                 390                 395                 400

Phe Ser Ser Ala Asp Lys Tyr Asp Ser Gly Cys Gly Trp Pro Ser Phe
                405                 410                 415

Thr Arg Pro Ile Asp Ala Lys Ser Val Thr Glu His Asp Asp Phe Ser
            420                 425                 430

Phe Asn Met Arg Arg Thr Glu Val Arg Ser Arg Ala Ala Asp Ser His
                435                 440                 445

Leu Gly His Val Phe Pro Asp Gly Pro Arg Asp Lys Gly Gly Leu Arg
    450                 455                 460

Tyr Cys Ile Asn Gly Ala Ser Leu Lys Phe Ile Pro Leu Glu Gln Met
465                 470                 475                 480

Asp Ala Ala Gly Tyr Gly Ala Leu Lys Gly Lys Val Lys
                485                 490
```

<210> SEQ ID NO 9
<211> LENGTH: 522
<212> TYPE: PRT
<213> ORGANISM: Neisseria gonorrhoeae

<400> SEQUENCE: 9

```
Met Lys His Arg Thr Phe Phe Ser Leu Cys Ala Lys Phe Gly Cys Leu
1               5                   10                  15

Leu Ala Leu Gly Ala Cys Ser Pro Lys Ile Val Asp Ala Gly Ala Ala
                20                  25                  30
```

```
Thr Val Pro His Thr Leu Ser Thr Leu Lys Thr Ala Asp Asn Arg Pro
            35                  40                  45

Ala Ser Val Tyr Leu Lys Lys Asp Lys Pro Thr Leu Ile Lys Phe Trp
 50                  55                  60

Ala Ser Trp Cys Pro Leu Cys Leu Ser Glu Leu Gly Gln Ala Glu Lys
 65                  70                  75                  80

Trp Ala Gln Asp Ala Lys Phe Ser Ser Ala Asn Leu Ile Thr Val Ala
                 85                  90                  95

Ser Pro Gly Phe Leu His Glu Lys Lys Asp Gly Glu Phe Gln Lys Trp
            100                 105                 110

Tyr Ala Gly Leu Asn Tyr Pro Lys Leu Pro Val Val Thr Asp Asn Gly
            115                 120                 125

Gly Thr Ile Ala Gln Asn Leu Asn Ile Ser Val Tyr Pro Ser Trp Ala
            130                 135                 140

Leu Ile Gly Lys Asp Gly Asp Val Gln Arg Ile Val Lys Gly Ser Ile
145                 150                 155                 160

Asn Glu Ala Gln Ala Leu Ala Leu Ile Arg Asn Pro Asn Ala Asp Leu
                165                 170                 175

Gly Ser Leu Lys His Ser Phe Tyr Lys Pro Asp Thr Gln Lys Lys Asp
            180                 185                 190

Ser Ala Ile Met Asn Thr Arg Thr Ile Tyr Leu Ala Gly Gly Cys Phe
            195                 200                 205

Trp Gly Leu Glu Ala Tyr Phe Gln Arg Ile Asp Gly Val Val Asp Ala
            210                 215                 220

Val Ser Gly Tyr Ala Asn Gly Asn Thr Glu Asn Pro Ser Tyr Glu Asp
225                 230                 235                 240

Val Ser Tyr Arg His Thr Gly His Ala Glu Thr Val Lys Val Thr Tyr
                245                 250                 255

Asp Ala Asp Lys Leu Ser Leu Asp Asp Ile Leu Gln Tyr Tyr Phe Arg
            260                 265                 270

Val Val Asp Pro Thr Ser Leu Asn Lys Gln Gly Asn Asp Thr Gly Thr
            275                 280                 285

Gln Tyr Arg Ser Gly Val Tyr Tyr Thr Asp Pro Ala Glu Lys Ala Val
            290                 295                 300

Ile Ala Ala Ala Leu Lys Arg Glu Gln Gln Lys Tyr Gln Leu Pro Leu
305                 310                 315                 320

Val Val Glu Asn Glu Pro Leu Lys Asn Phe Tyr Asp Ala Glu Glu Tyr
                325                 330                 335

His Gln Asp Tyr Leu Ile Lys Asn Pro Asn Gly Tyr Cys His Ile Asp
            340                 345                 350

Ile Arg Lys Ala Asp Glu Pro Leu Pro Gly Lys Thr Lys Ala Ala Pro
            355                 360                 365

Gln Gly Lys Gly Phe Asp Ala Ala Thr Tyr Lys Lys Pro Ser Asp Ala
            370                 375                 380

Glu Leu Lys Arg Thr Leu Thr Glu Glu Gln Tyr Gln Val Thr Gln Asn
385                 390                 395                 400

Ser Ala Thr Glu Tyr Ala Phe Ser His Glu Tyr Asp His Leu Phe Lys
                405                 410                 415

Pro Gly Ile Tyr Val Asp Val Val Ser Gly Glu Pro Leu Phe Ser Ser
            420                 425                 430

Ala Asp Lys Tyr Asp Ser Gly Cys Gly Trp Pro Ser Phe Thr Arg Pro
            435                 440                 445
```

```
Ile Asp Ala Lys Ser Val Thr Glu His Asp Asp Phe Ser Phe Asn Met
450                 455                 460

Arg Arg Thr Glu Val Arg Ser Arg Ala Ala Asp Ser His Leu Gly His
465                 470                 475                 480

Val Phe Pro Asp Gly Pro Arg Asp Lys Gly Gly Leu Arg Tyr Cys Ile
                485                 490                 495

Asn Gly Ala Ser Leu Lys Phe Ile Pro Leu Glu Gln Met Asp Ala Ala
                500                 505                 510

Gly Tyr Gly Ala Leu Lys Gly Lys Val Lys
                515                 520

<210> SEQ ID NO 10
<211> LENGTH: 522
<212> TYPE: PRT
<213> ORGANISM: Neisseria gonorrhoeae

<400> SEQUENCE: 10

Met Lys His Arg Thr Phe Phe Ser Leu Cys Ala Lys Phe Gly Cys Leu
1               5                   10                  15

Leu Ala Leu Gly Ala Cys Ser Pro Lys Ile Val Asp Ala Gly Ala Ala
                20                  25                  30

Thr Val Pro His Thr Leu Ser Thr Leu Lys Thr Ala Asp Asn Arg Pro
                35                  40                  45

Ala Ser Val Tyr Leu Lys Lys Asp Lys Pro Thr Leu Ile Lys Phe Trp
50                  55                  60

Ala Ser Trp Cys Pro Leu Cys Leu Ser Glu Leu Gly Gln Ala Glu Lys
65                  70                  75                  80

Trp Ala Gln Asp Ala Lys Phe Ser Ser Ala Asn Leu Ile Thr Val Ala
                85                  90                  95

Ser Pro Gly Phe Leu His Glu Lys Lys Asp Gly Glu Phe Gln Lys Trp
                100                 105                 110

Tyr Ala Gly Leu Asn Tyr Pro Lys Leu Pro Val Val Thr Asp Asn Gly
                115                 120                 125

Gly Thr Ile Ala Gln Asn Leu Asn Ile Ser Val Tyr Pro Ser Trp Ala
130                 135                 140

Leu Ile Gly Lys Asp Gly Asp Val Gln Arg Ile Val Lys Gly Ser Ile
145                 150                 155                 160

Asn Glu Ala Gln Ala Leu Ala Leu Ile Arg Asn Pro Asn Ala Asp Leu
                165                 170                 175

Gly Ser Leu Lys His Ser Phe Tyr Lys Pro Asp Thr Gln Lys Lys Asp
                180                 185                 190

Ser Ala Ile Met Asn Thr Arg Thr Ile Tyr Leu Ala Gly Gly Cys Phe
                195                 200                 205

Trp Gly Leu Glu Ala Tyr Phe Gln Arg Ile Asp Gly Val Val Asp Ala
                210                 215                 220

Val Ser Gly Tyr Ala Asn Gly Asn Thr Glu Asn Pro Ser Tyr Glu Asp
225                 230                 235                 240

Val Ser Tyr Arg His Thr Gly His Ala Glu Thr Val Lys Val Thr Tyr
                245                 250                 255

Asp Ala Asp Lys Leu Ser Leu Asp Ile Leu Gln Tyr Tyr Phe Arg
                260                 265                 270

Val Val Asp Pro Thr Ser Leu Asn Lys Gln Gly Asn Asp Thr Gly Thr
                275                 280                 285

Gln Tyr Arg Ser Gly Val Tyr Tyr Thr Asp Pro Ala Glu Lys Ala Val
290                 295                 300
```

Ile Ala Ala Ala Leu Lys Arg Glu Gln Gln Lys Tyr Gln Leu Pro Leu
305                 310                 315                 320

Val Val Glu Asn Glu Pro Leu Lys Asn Phe Tyr Asp Ala Glu Glu Tyr
            325                 330                 335

His Gln Asp Tyr Leu Ile Lys Asn Pro Asn Gly Tyr Cys His Ile Asp
            340                 345                 350

Ile Arg Lys Ala Asp Glu Pro Leu Pro Gly Lys Thr Lys Ala Ala Pro
355                 360                 365

Gln Gly Lys Gly Phe Asp Ala Ala Thr Tyr Lys Lys Pro Ser Asp Ala
        370                 375                 380

Glu Leu Lys Arg Thr Leu Thr Glu Glu Gln Tyr Gln Val Thr Gln Asn
385                 390                 395                 400

Ser Ala Thr Glu Tyr Ala Phe Ser His Glu Tyr Asp His Leu Phe Lys
            405                 410                 415

Pro Gly Ile Tyr Val Asp Val Val Ser Gly Glu Pro Leu Phe Ser Ser
        420                 425                 430

Ala Asp Lys Tyr Asp Ser Gly Cys Gly Trp Pro Ser Phe Thr Arg Pro
        435                 440                 445

Ile Asp Ala Lys Ser Val Thr Glu His Asp Asp Phe Ser Phe Asn Met
450                 455                 460

Arg Arg Thr Glu Val Arg Ser Arg Ala Ala Asp Ser His Leu Gly His
465                 470                 475                 480

Val Phe Pro Asp Gly Pro Arg Asp Lys Gly Leu Arg Tyr Cys Ile
            485                 490                 495

Asn Gly Ala Ser Leu Lys Phe Ile Pro Leu Glu Gln Met Asp Ala Ala
            500                 505                 510

Gly Tyr Gly Ala Leu Lys Gly Glu Val Lys
        515                 520

<210> SEQ ID NO 11
<211> LENGTH: 522
<212> TYPE: PRT
<213> ORGANISM: Neisseria gonorrhoeae

<400> SEQUENCE: 11

Met Lys His Arg Thr Phe Phe Ser Leu Cys Ala Lys Phe Gly Cys Leu
1               5                   10                  15

Leu Ala Leu Gly Ala Cys Ser Pro Lys Ile Val Asp Ala Gly Thr Ala
            20                  25                  30

Thr Val Pro His Thr Leu Ser Thr Leu Lys Thr Ala Asp Asn Arg Pro
        35                  40                  45

Ala Ser Val Tyr Leu Lys Lys Asp Lys Pro Thr Leu Ile Lys Phe Trp
    50                  55                  60

Ala Ser Trp Cys Pro Leu Cys Leu Ser Glu Leu Gly Gln Ala Glu Lys
65                  70                  75                  80

Trp Ala Gln Asp Ala Lys Phe Ser Ala Asn Leu Ile Thr Val Ala
            85                  90                  95

Ser Pro Gly Phe Leu His Glu Lys Lys Asp Gly Glu Phe Gln Lys Trp
            100                 105                 110

Tyr Ala Gly Leu Asn Tyr Pro Lys Leu Pro Val Val Thr Asp Asn Gly
        115                 120                 125

Gly Thr Ile Ala Gln Asn Leu Asn Ile Ser Val Tyr Pro Ser Trp Ala
    130                 135                 140

Leu Ile Gly Lys Asp Gly Asp Val Gln Arg Ile Val Lys Gly Ser Ile

```
                145                 150                 155                 160
Asn Glu Ala Gln Ala Leu Ala Leu Ile Arg Asn Pro Asn Ala Asp Leu
                    165                 170                 175

Gly Ser Leu Lys His Ser Phe Tyr Lys Pro Asp Thr Gln Lys Lys Asp
                180                 185                 190

Ser Ala Ile Met Asn Thr Arg Thr Ile Tyr Leu Ala Gly Gly Cys Phe
                195                 200                 205

Trp Gly Leu Glu Ala Tyr Phe Gln Arg Ile Asp Gly Val Val Asp Ala
        210                 215                 220

Val Ser Gly Tyr Ala Asn Gly Asn Thr Glu Asn Pro Ser Tyr Glu Asp
225                 230                 235                 240

Val Ser Tyr Arg His Thr Gly His Ala Glu Thr Val Lys Val Thr Tyr
                    245                 250                 255

Asp Ala Asp Lys Leu Ser Leu Asp Ile Leu Gln Tyr Tyr Phe Arg
                260                 265                 270

Val Val Asp Pro Thr Ser Leu Asn Lys Gln Gly Asn Asp Thr Gly Thr
                275                 280                 285

Gln Tyr Arg Ser Gly Val Tyr Tyr Thr Asp Pro Ala Glu Lys Ala Val
        290                 295                 300

Ile Ala Ala Ala Leu Lys Arg Glu Gln Gln Lys Tyr Gln Leu Pro Leu
305                 310                 315                 320

Val Val Glu Asn Glu Pro Leu Lys Asn Phe Tyr Asp Ala Glu Glu Tyr
                    325                 330                 335

His Gln Asp Tyr Leu Ile Lys Asn Pro Asn Gly Tyr Cys His Ile Asp
                340                 345                 350

Ile Arg Lys Ala Asp Glu Pro Leu Pro Gly Lys Thr Lys Ala Ala Pro
                355                 360                 365

Gln Gly Lys Gly Phe Asp Ala Ala Thr Tyr Lys Lys Pro Ser Asp Ala
        370                 375                 380

Glu Leu Lys Arg Thr Leu Thr Glu Gln Tyr Gln Val Thr Gln Asn
385                 390                 395                 400

Ser Ala Thr Glu Tyr Ala Phe Ser His Glu Tyr Asp His Leu Phe Lys
                    405                 410                 415

Pro Gly Ile Tyr Val Asp Val Val Ser Gly Glu Pro Leu Phe Ser Ser
                420                 425                 430

Ala Asp Lys Tyr Asp Ser Gly Cys Gly Trp Pro Ser Phe Thr Arg Pro
                435                 440                 445

Ile Asp Ala Lys Ser Val Thr Glu His Asp Asp Phe Ser Phe Asn Met
        450                 455                 460

Arg Arg Thr Glu Val Arg Ser Arg Ala Ala Asp Ser His Leu Gly His
465                 470                 475                 480

Val Phe Pro Asp Gly Pro Arg Asp Lys Gly Leu Arg Tyr Cys Ile
                    485                 490                 495

Asn Gly Ala Ser Leu Lys Phe Ile Pro Leu Glu Gln Met Asp Ala Ala
                500                 505                 510

Gly Tyr Gly Ala Leu Lys Gly Glu Val Lys
        515                 520
```

<210> SEQ ID NO 12
<211> LENGTH: 522
<212> TYPE: PRT
<213> ORGANISM: Neisseria gonorrhoeae

<400> SEQUENCE: 12

```
Met Lys His Arg Thr Phe Phe Ser Leu Cys Ala Lys Phe Gly Cys Leu
1               5                   10                  15

Leu Ala Leu Gly Ala Cys Ser Pro Lys Ile Val Asp Ala Gly Ala Ala
            20                  25                  30

Thr Val Pro His Thr Leu Ser Thr Leu Lys Thr Ala Asp Asn Arg Pro
            35                  40                  45

Ala Ser Val Tyr Leu Lys Lys Asp Lys Pro Thr Leu Ile Lys Phe Trp
    50                  55                  60

Ala Ser Trp Cys Pro Leu Cys Leu Ser Glu Leu Gly Gln Thr Glu Lys
65                  70                  75                  80

Trp Ala Gln Asp Ala Lys Phe Ser Ser Ala Asn Leu Ile Thr Val Ala
                85                  90                  95

Ser Pro Gly Phe Leu His Glu Lys Lys Asp Gly Asp Phe Gln Lys Trp
                100                 105                 110

Tyr Ala Gly Leu Asn Tyr Pro Lys Leu Pro Val Val Thr Asp Asn Gly
            115                 120                 125

Gly Thr Ile Ala Gln Ser Leu Asn Ile Ser Val Tyr Pro Ser Trp Ala
    130                 135                 140

Leu Ile Gly Lys Asp Ser Asp Val Gln Arg Ile Val Lys Gly Ser Ile
145                 150                 155                 160

Asn Glu Ala Gln Ala Leu Ala Leu Ile Arg Asp Pro Asn Ala Asp Leu
                165                 170                 175

Gly Ser Leu Lys His Ser Phe Tyr Lys Pro Asp Thr Gln Lys Lys Asp
            180                 185                 190

Ser Lys Ile Met Asn Thr Arg Thr Ile Tyr Leu Ala Gly Gly Cys Phe
    195                 200                 205

Trp Gly Leu Glu Ala Tyr Phe Gln Arg Ile Asp Gly Val Val Asp Ala
    210                 215                 220

Val Ser Gly Tyr Ala Asn Gly Asn Thr Lys Asn Pro Ser Tyr Glu Asp
225                 230                 235                 240

Val Ser Tyr Arg His Thr Gly His Ala Glu Thr Val Lys Val Thr Tyr
            245                 250                 255

Asp Ala Asp Lys Leu Ser Leu Asp Asp Ile Leu Gln Tyr Phe Phe Arg
            260                 265                 270

Val Val Asp Pro Thr Ser Leu Asn Lys Gln Gly Asn Asp Thr Gly Thr
            275                 280                 285

Gln Tyr Arg Ser Gly Val Tyr Tyr Thr Asp Pro Ala Glu Lys Ala Val
    290                 295                 300

Ile Ala Ala Ala Leu Lys Arg Glu Gln Gln Lys Tyr Gln Leu Pro Leu
305                 310                 315                 320

Val Val Glu Asn Glu Pro Leu Lys Asn Phe Tyr Asp Ala Glu Glu Tyr
            325                 330                 335

His Gln Asp Tyr Leu Ile Lys Asn Pro Asn Gly Tyr Cys His Ile Asp
            340                 345                 350

Ile Arg Lys Ala Asp Glu Pro Leu Pro Gly Lys Thr Lys Thr Ala Pro
    355                 360                 365

Gln Gly Lys Gly Phe Asp Ala Ala Thr Tyr Lys Lys Pro Ser Asp Ala
    370                 375                 380

Glu Leu Lys Arg Thr Leu Thr Glu Glu Gln Tyr Gln Val Thr Gln Asn
385                 390                 395                 400

Ser Ala Thr Glu Tyr Ala Phe Ser His Glu Tyr Asp His Leu Phe Lys
            405                 410                 415

Pro Gly Ile Tyr Val Asp Val Val Ser Gly Glu Pro Leu Phe Ser Ser
```

```
              420              425              430
Ala Asp Lys Tyr Asp Ser Gly Cys Gly Trp Pro Ser Phe Thr Arg Pro
            435                  440                 445

Ile Asp Ala Lys Ser Val Thr Glu His Asp Asp Phe Ser Tyr Asn Met
            450                  455                 460

Arg Arg Thr Glu Val Arg Ser His Ala Ala Asp Ser His Leu Gly His
465                  470                 475                 480

Val Phe Pro Asp Gly Pro Arg Asp Lys Gly Gly Leu Arg Tyr Cys Ile
                485                 490                 495

Asn Gly Ala Ser Leu Lys Phe Ile Pro Leu Glu Gln Met Asp Ala Ala
                500                 505                 510

Gly Tyr Gly Ala Leu Lys Gly Lys Val Lys
                515                 520

<210> SEQ ID NO 13
<211> LENGTH: 1569
<212> TYPE: DNA
<213> ORGANISM: Neisseria gonorrhoeae

<400> SEQUENCE: 13
```

| | | | | | |
|---|---|---|---|---|---|
| atgaaacacc | gtactttctt | ttcccttttgc | gccaagttcg | gctgcctgct | tgcgctgggc | 60 |
| gcttgttcgc | ccaaaatcgt | cgatgccggg | accgcgaccg | tgccgcacac | tttatccacg | 120 |
| ttaaaaaccg | cggacaaccg | ccccgccagt | gtttatttga | aaaagacaa | accgacgctg | 180 |
| attaaatttt | gggcgagctg | gtgtcctta | tgtttgtccg | aattgggaca | ggccgagaaa | 240 |
| tgggcgcaag | atgcaaaatt | cagctccgcc | aacctgatta | ccgtcgcctc | ccccggcttt | 300 |
| ttgcacgaga | aaaaagacgg | cgagtttcaa | aatggtatg | ccggtttgaa | ctaccccaag | 360 |
| ctgcccgtcg | ttaccgacaa | cggcggcacg | atcgcccaaa | acctgaatat | cagcgtttat | 420 |
| ccttcttggg | cgttaatcgg | taaagacggc | gacgtgcagc | gcatcgtcaa | aggcagcatc | 480 |
| aacgaagcgc | aggcattggc | gttaatccgc | aaccccgaatg | ccgatttggg | cagtttgaaa | 540 |
| cattcgttct | acaaacccga | cactcagaaa | aaggattcag | caatcatgaa | cacgcgcacc | 600 |
| atctacctcg | ccggcggctg | cttctggggc | ttggaagcct | atttccaacg | catcgacggc | 660 |
| gtggttgacg | cggtatccgg | ctacgccaac | ggcaacacgg | aaaacccgag | ctacgaagac | 720 |
| gtgtcctacc | gccatacggg | ccatgccgag | accgtcaaag | tgacctacga | tgccgacaaa | 780 |
| ctcagcctgg | acgacatcct | gcaatattat | ttccgcgtcg | ttgatccgac | cagcctcaac | 840 |
| aaacagggta | cgacaccgg | cacgcaatac | cgcagcggcg | tgtactacac | cgaccccgcc | 900 |
| gaaaagccg | tcatcgccgc | cgccctcaaa | cgcgagcagc | aaaaatacca | actgccccctc | 960 |
| gttgttgaaa | cgaaccgct | gaaaaacttc | tacgacgccg | aggaatacca | tcaggactac | 1020 |
| ctgattaaaa | accccaacgg | ctactgccac | atcgacatcc | gcaaagccga | cgaaccgctg | 1080 |
| ccgggcaaaa | ccaaagccgc | accgcaaggc | aaaggcttcg | acgcggcaac | gtataaaaaa | 1140 |
| ccgagtgacg | ccgaactcaa | acgcaccctg | accgaagagc | aataccaagt | gacccaaaac | 1200 |
| agcgcgaccg | aatacgcctt | cagccacgaa | tacgaccatt | tgttcaaacc | cggcatttat | 1260 |
| gtggacgttg | tcagcggcga | accctgttc | agctccgccg | acaaatatga | ttccggctgc | 1320 |
| ggctggccga | gcttcacgcg | cccgattgat | gcaaaatccg | ttaccgaaca | cgatgatttc | 1380 |
| agcttcaata | tgcgccgcac | cgaagtcaga | agccgcgccg | ccgattcgca | cttgggacac | 1440 |
| gtcttccccg | acgccccccg | cgacaaaggc | ggactgcgct | actgcatcaa | cggcgcgagc | 1500 |
| ttgaaattca | tccccgctgga | acaaatggac | gcggcaggct | acggcgcgtt | gaagggcaaa | 1560 |

-continued

```
gtgaaataa                                                           1569
```

<210> SEQ ID NO 14
<211> LENGTH: 1476
<212> TYPE: DNA
<213> ORGANISM: Neisseria gonorrhoeae

<400> SEQUENCE: 14

```
gcgaccgtgc cgcacacttt atccacgtta aaaccgcgg acaaccgccc cgccagtgtt     60
tatttgaaaa aagacaaacc gacgctgatt aaattttggg cgagctggtg tcctttatgt    120
ttgtccgaat tgggacaggc cgagaaatgg gcgcaagatg caaaattcag ctccgccaac    180
ctgattaccg tcgcctcccc cggcttttg cacgagaaaa aagacggcga gtttcaaaaa     240
tggtatgccg gtttgaacta ccccaagctg cccgtcgtta ccgacaacgg cggcacgatc    300
gcccaaaacc tgaatatcag cgtttatcct tcttgggcgt taatcggtaa agacggcgac    360
gtgcagcgca tcgtcaaagg cagcatcaac gaagcgcagg cattggcgtt aatccgcaac    420
ccgaatgccg atttgggcag tttgaaacat tcgttctaca acccgacac tcagaaaaag    480
gattcagcaa tcatgaacac gcgcaccatc tacctcgccg gcggctgctt ctggggcttg    540
gaagcctatt tccaacgcat cgacggcgtg gttgacgcgg tatccggcta cgccaacggc    600
aacacggaaa acccgagcta cgaagacgtg tcctaccgcc atacgggcca tgccgagacc    660
gtcaaagtga cctacgatgc cgacaaactc agcctggacg acatcctgca atattatttc    720
cgcgtcgttg atccgaccag cctcaacaaa cagggtaacg acaccggcac gcaataccgc    780
agcggcgtgt actacaccga ccccgccgaa aaagccgtca tcgccgccgc cctcaaacgc    840
gagcagcaaa ataccaact gccctcgtt gttgaaaacg aaccgctgaa aaacttctac       900
gacgccgagg aataccatca ggactacctg attaaaaacc ccaacggcta ctgccacatc    960
gacatccgca aagccgacga accgctgccg ggcaaaacca agccgcacc gcaaggcaaa    1020
ggcttcgacg cggcaacgta taaaaaaccg agtgacgccg aactcaaacg caccctgacc    1080
gaagagcaat accaagtgac ccaaaacagc gcgaccgaat acgccttcag ccacgaatac    1140
gaccatttgt tcaaacccgg catttatgtg gacgttgtca gcggcgaacc cctgttcagc    1200
tccgccgaca aatatgattc cggctgcggc tggccgagct tcacgcgccc gattgatgca    1260
aaatccgtta ccgaacacga tgatttcagc ttcaatatgc ccgcaccga agtcagaagc    1320
cgcgccgccg attcgcactt gggacacgtc ttccccgacg gccccgcga caaaggcgga    1380
ctgcgctact gcatcaacgg cgcgagcttg aaattcatcc gctggaaca atggacgcg    1440
gcaggctacg gcgcgttgaa gggcaaagtg aaataa                             1476
```

<210> SEQ ID NO 15
<211> LENGTH: 515
<212> TYPE: PRT
<213> ORGANISM: Artificial Sequence
<220> FEATURE:
<223> OTHER INFORMATION: MsrA/B/His/linker

<400> SEQUENCE: 15

```
Met Gly Ser Ser His His His His His His Ser Gly Leu Val Pro
 1               5                  10                  15

Arg Gly Ser His Met Lys Gly Thr Ala Thr Val Pro His Thr Leu Ser
                20                  25                  30

Thr Leu Lys Thr Ala Asp Asn Arg Pro Ala Ser Val Tyr Leu Lys Lys
            35                  40                  45
```

```
Asp Lys Pro Thr Leu Ile Lys Phe Trp Ala Ser Trp Cys Pro Leu Cys
     50                  55                  60

Leu Ser Glu Leu Gly Gln Ala Glu Lys Trp Ala Gln Asp Ala Lys Phe
 65                  70                  75                  80

Ser Ser Ala Asn Leu Ile Thr Val Ala Ser Pro Gly Phe Leu His Glu
                 85                  90                  95

Lys Lys Asp Gly Glu Phe Gln Lys Trp Tyr Ala Gly Leu Asn Tyr Pro
            100                 105                 110

Lys Leu Pro Val Val Thr Asp Asn Gly Gly Thr Ile Ala Gln Asn Leu
            115                 120                 125

Asn Ile Ser Val Tyr Pro Ser Trp Ala Leu Ile Gly Lys Asp Gly Asp
            130                 135                 140

Val Gln Arg Ile Val Lys Gly Ser Ile Asn Glu Ala Gln Ala Leu Ala
145                 150                 155                 160

Leu Ile Arg Asn Pro Asn Ala Asp Leu Gly Ser Leu Lys His Ser Phe
                165                 170                 175

Tyr Lys Pro Asp Thr Gln Lys Lys Asp Ser Ala Ile Met Asn Thr Arg
            180                 185                 190

Thr Ile Tyr Leu Ala Gly Gly Cys Phe Trp Gly Leu Glu Ala Tyr Phe
            195                 200                 205

Gln Arg Ile Asp Gly Val Val Asp Ala Val Ser Gly Tyr Ala Asn Gly
210                 215                 220

Asn Thr Glu Asn Pro Ser Tyr Glu Asp Val Ser Tyr Arg His Thr Gly
225                 230                 235                 240

His Ala Glu Thr Val Lys Val Thr Tyr Asp Ala Asp Lys Leu Ser Leu
                245                 250                 255

Asp Asp Ile Leu Gln Tyr Tyr Phe Arg Val Val Asp Pro Thr Ser Leu
            260                 265                 270

Asn Lys Gln Gly Asn Asp Thr Gly Thr Gln Tyr Arg Ser Gly Val Tyr
            275                 280                 285

Tyr Thr Asp Pro Ala Glu Lys Ala Val Ile Ala Ala Ala Leu Lys Arg
            290                 295                 300

Glu Gln Gln Lys Tyr Gln Leu Pro Leu Val Val Glu Asn Glu Pro Leu
305                 310                 315                 320

Lys Asn Phe Tyr Asp Ala Glu Glu Tyr His Gln Asp Tyr Leu Ile Lys
            325                 330                 335

Asn Pro Asn Gly Tyr Cys His Ile Asp Ile Arg Lys Ala Asp Glu Pro
            340                 345                 350

Leu Pro Gly Lys Thr Lys Ala Ala Pro Gln Gly Lys Gly Phe Asp Ala
            355                 360                 365

Ala Thr Tyr Lys Lys Pro Ser Asp Ala Glu Leu Lys Arg Thr Leu Thr
            370                 375                 380

Glu Glu Gln Tyr Gln Val Thr Gln Asn Ser Ala Thr Glu Tyr Ala Phe
385                 390                 395                 400

Ser His Glu Tyr Asp His Leu Phe Lys Pro Gly Ile Tyr Val Asp Val
                405                 410                 415

Val Ser Gly Glu Pro Leu Phe Ser Ser Ala Asp Lys Tyr Asp Ser Gly
            420                 425                 430

Cys Gly Trp Pro Ser Phe Thr Arg Pro Ile Asp Ala Lys Ser Val Thr
            435                 440                 445

Glu His Asp Asp Phe Ser Phe Asn Met Arg Arg Thr Glu Val Arg Ser
            450                 455                 460
```

```
Arg Ala Ala Asp Ser His Leu Gly His Val Phe Pro Asp Gly Pro Arg
465                 470                 475                 480

Asp Lys Gly Gly Leu Arg Tyr Cys Ile Asn Gly Ala Ser Leu Lys Phe
            485                 490                 495

Ile Pro Leu Glu Gln Met Asp Ala Ala Gly Tyr Gly Ala Leu Lys Gly
            500                 505                 510

Lys Val Lys
        515

<210> SEQ ID NO 16
<211> LENGTH: 1548
<212> TYPE: DNA
<213> ORGANISM: Artificial Sequence
<220> FEATURE:
<223> OTHER INFORMATION: MsrA/B/His/linker

<400> SEQUENCE: 16
atgggcagca gccatcatca tcatcatcac agcagcggcc tggtgccgcg cggcagccat      60
atgaaaggga ccgcgaccgt gccgcacact ttatccacgt taaaaaccgc ggacaaccgc     120
cccgccagtg tttatttgaa aaaagacaaa ccgacgctga ttaaattttg ggcgagctgg     180
tgtcctttat gtttgtccga attgggacag gccgagaaat gggcgcaaga tgcaaaattc     240
agctccgcca acctgattac cgtcgcctcc cccggctttt tgcacgagaa aaaagacggc     300
gagtttcaaa atggtatgc cggtttgaac taccccaagc tgcccgtcgt taccgacaac     360
ggcggcacga tcgcccaaaa cctgaatatc agcgtttatc cttcttgggc gttaatcggt     420
aaagacggcg acgtgcagcg catcgtcaaa ggcagcatca cgaagcgca ggcattggcg      480 ttaatccgca acccgaatgc cgatttgggc agtttgaaac attcgttcta caaacccgac     540
actcagaaaa aggattcagc aatcatgaac acgcgcacca tctacctcgc cggcggctgc     600
ttctggggct tggaagccta tttccaacgc atcgacggcg tggttgacgc ggtatccggc     660
tacgccaacg gcaacacgga aaacccgagc tacgaagacg tgtcctaccg ccatacgggc     720
catgccgaga ccgtcaaagt gacctacgat gccgacaaac tcagcctgga cgacatcctg     780
caatattatt tccgcgtcgt tgatccgacc agcctcaaca acagggtaa cgacaccggc      840 acgcaatacc gcagcggcgt gtactacacc gaccccgccg aaaaagccgt catcgccgcc     900
gccctcaaac gcgagcagca aaataccaa ctgcccctcg ttgttgaaaa cgaaccgctg      960
aaaaacttct acgacgccga ggaataccat caggactacc tgattaaaaa ccccaacggc    1020
tactgccaca tcgacatccg caaagccgac gaaccgctgc cgggcaaaac caaagccgca    1080
ccgcaaggca aaggcttcga cgcggcaacg tataaaaaac cgagtgacgc cgaactcaaa    1140
cgcaccctga ccgaagagca ataccaagtg acccaaaaca cgcgcaccga atacgccttc    1200
agccacgaat acgaccattt gttcaaaccc ggcatttatg tggacgttgt cagcggcgaa    1260
cccctgttca gctccgccga caatatgat tccggctgcg gctggccgag cttcacgcgc    1320
ccgattgatg caaaatccgt taccgaacac gatgatttca gcttcaatat gcgccgcacc    1380
gaagtcagaa gccgcgccgc cgattcgcac ttgggacacg tcttccccga cggccccgc    1440 gacaaaggcg gactgcgcta ctgcatcaac ggcgcgagct tgaaattcat cccgctggaa    1500
caaatggacg cggcaggcta cggcgcgttg aagggcaaag tgaaataa                 1548

<210> SEQ ID NO 17
<211> LENGTH: 35
<212> TYPE: DNA
<213> ORGANISM: Artificial Sequence
```

```
<220> FEATURE:
<223> OTHER INFORMATION: Primer 1291msrFor

<400> SEQUENCE: 17
gccgtctgaa atgaaacacc gtactttctt ttccc                                35

<210> SEQ ID NO 18
<211> LENGTH: 35
<212> TYPE: DNA
<213> ORGANISM: Artificial Sequence
<220> FEATURE:
<223> OTHER INFORMATION: Primer 1291msrRev

<400> SEQUENCE: 18
ttcagacggc ttatttcact ttgcccttca acgcg                                35

<210> SEQ ID NO 19
<211> LENGTH: 10
<212> TYPE: DNA
<213> ORGANISM: Neisseria gonorrhoeae

<400> SEQUENCE: 19
gccgtctgaa                                                            10

<210> SEQ ID NO 20
<211> LENGTH: 35
<212> TYPE: DNA
<213> ORGANISM: Artificial Sequence
<220> FEATURE:
<223> OTHER INFORMATION: Primer msrexp_NdeIF

<400> SEQUENCE: 20
aaaatccata tgaaagggac cgcgaccgtg ccgca                                35

<210> SEQ ID NO 21
<211> LENGTH: 31
<212> TYPE: DNA
<213> ORGANISM: Artificial Sequence
<220> FEATURE:
<223> OTHER INFORMATION: Primer msrexp_XhoIR

<400> SEQUENCE: 21
ccctgactcg agttatttca ctttgcccct t c                                  31

<210> SEQ ID NO 22
<211> LENGTH: 27
<212> TYPE: DNA
<213> ORGANISM: Artificial Sequence
<220> FEATURE:
<223> OTHER INFORMATION: Primer 15bmsrAFor_NdeI

<400> SEQUENCE: 22
ttgggccata tgaaacattc gttctac                                         27

<210> SEQ ID NO 23
<211> LENGTH: 32
<212> TYPE: DNA
<213> ORGANISM: Artificial Sequence
<220> FEATURE:
<223> OTHER INFORMATION: Primer 15bmsrARev_XhoI

<400> SEQUENCE: 23
ggctttctcg agttagcccg gcagcggttc gt                                   32

<210> SEQ ID NO 24
```

```
<210> SEQ ID NO 24
<211> LENGTH: 31
<212> TYPE: DNA
<213> ORGANISM: Artificial Sequence
<220> FEATURE:
<223> OTHER INFORMATION: Primer 15bmsrBFor_NdeI

<400> SEQUENCE: 24
ggcaaacata tgaaagcggc aacgtataaa a                              31

<210> SEQ ID NO 25
<211> LENGTH: 33
<212> TYPE: DNA
<213> ORGANISM: Artificial Sequence
<220> FEATURE:
<223> OTHER INFORMATION: Primer 15bmsrBRev_XhoI

<400> SEQUENCE: 25
tgcggcctcg agttatttca ctttgccctt caa                            33

<210> SEQ ID NO 26
<211> LENGTH: 615
<212> TYPE: DNA
<213> ORGANISM: Artificial Sequence
<220> FEATURE:
<223> OTHER INFORMATION: MsrA/His/linker

<400> SEQUENCE: 26
atgggcagca gccatcatca tcatcatcac agcagcggcc tggtgccgcg cggcagccat     60
atgaaacatt cgttctacaa acccgacact cagaaaaagg attcagcaat catgaacacg    120
cgcaccatct acctcgccgg cggctgcttc tggggcttgg aagcctattt ccaacgcatc    180
gacggcgtgg ttgacgcggt atccggctac gccaacggca acacggaaaa cccgagctac    240
gaagacgtgt cctaccgcca tacgggccat gccgagaccg tcaaagtgac ctacgatgcc    300
gacaaactca gcctggacga catcctgcaa tattatttcc gcgtcgttga tccgaccagc    360
ctcaacaaac agggtaacga caccggcacg caataccgca gcggcgtgta ctacaccgac    420
cccgccgaaa agccgtcat cgccgccgcc ctcaaacgcg agcagcaaaa ataccaactg    480
cccctcgttg ttgaaaacga accgctgaaa aacttctacg acgccgagga ataccatcag    540
gactacctga ttaaaaaccc caacggctac tgccacatcg acatccgcaa agccgacgaa    600
ccgctgccgg gctaa                                                    615

<210> SEQ ID NO 27
<211> LENGTH: 204
<212> TYPE: PRT
<213> ORGANISM: Artificial Sequence
<220> FEATURE:
<223> OTHER INFORMATION: MsrA/His/linker

<400> SEQUENCE: 27

Met Gly Ser Ser His His His His His His Ser Ser Gly Leu Val Pro
1               5                   10                  15

Arg Gly Ser His Met Lys His Ser Phe Tyr Lys Pro Asp Thr Gln Lys
            20                  25                  30

Lys Asp Ser Ala Ile Met Asn Thr Arg Thr Ile Tyr Leu Ala Gly Gly
        35                  40                  45

Cys Phe Trp Gly Leu Glu Ala Tyr Phe Gln Arg Ile Asp Gly Val Val
    50                  55                  60

Asp Ala Val Ser Gly Tyr Ala Asn Gly Asn Thr Glu Asn Pro Ser Tyr
65                  70                  75                  80
```

Glu Asp Val Ser Tyr Arg His Thr Gly His Ala Glu Thr Val Lys Val
            85                  90                  95

Thr Tyr Asp Ala Asp Lys Leu Ser Leu Asp Asp Ile Leu Gln Tyr Tyr
        100                 105                 110

Phe Arg Val Val Asp Pro Thr Ser Leu Asn Lys Gln Gly Asn Asp Thr
        115                 120                 125

Gly Thr Gln Tyr Arg Ser Gly Val Tyr Tyr Thr Asp Pro Ala Glu Lys
        130                 135                 140

Ala Val Ile Ala Ala Leu Lys Arg Glu Gln Gln Lys Tyr Gln Leu
145                 150                 155                 160

Pro Leu Val Val Glu Asn Glu Pro Leu Lys Asn Phe Tyr Asp Ala Glu
        165                 170                 175

Glu Tyr His Gln Asp Tyr Leu Ile Lys Asn Pro Asn Gly Tyr Cys His
        180                 185                 190

Ile Asp Ile Arg Lys Ala Asp Glu Pro Leu Pro Gly
        195                 200

<210> SEQ ID NO 28
<211> LENGTH: 187
<212> TYPE: PRT
<213> ORGANISM: Artificial Sequence
<220> FEATURE:
<223> OTHER INFORMATION: Recombinant MsrA

<400> SEQUENCE: 28

Gly Ser His Met Lys His Ser Phe Tyr Lys Pro Asp Thr Gln Lys Lys
1               5                   10                  15

Asp Ser Ala Ile Met Asn Thr Arg Thr Ile Tyr Leu Ala Gly Gly Cys
            20                  25                  30

Phe Trp Gly Leu Glu Ala Tyr Phe Gln Arg Ile Asp Gly Val Val Asp
        35                  40                  45

Ala Val Ser Gly Tyr Ala Asn Gly Asn Thr Glu Asn Pro Ser Tyr Glu
    50                  55                  60

Asp Val Ser Tyr Arg His Thr Gly His Ala Glu Thr Val Lys Val Thr
65                  70                  75                  80

Tyr Asp Ala Asp Lys Leu Ser Leu Asp Asp Ile Leu Gln Tyr Tyr Phe
                85                  90                  95

Arg Val Val Asp Pro Thr Ser Leu Asn Lys Gln Gly Asn Asp Thr Gly
            100                 105                 110

Thr Gln Tyr Arg Ser Gly Val Tyr Tyr Thr Asp Pro Ala Glu Lys Ala
        115                 120                 125

Val Ile Ala Ala Leu Lys Arg Glu Gln Gln Lys Tyr Gln Leu Pro
    130                 135                 140

Leu Val Val Glu Asn Glu Pro Leu Lys Asn Phe Tyr Asp Ala Glu Glu
145                 150                 155                 160

Tyr His Gln Asp Tyr Leu Ile Lys Asn Pro Asn Gly Tyr Cys His Ile
                165                 170                 175

Asp Ile Arg Lys Ala Asp Glu Pro Leu Pro Gly
            180                 185

<210> SEQ ID NO 29
<211> LENGTH: 513
<212> TYPE: DNA
<213> ORGANISM: Artificial Sequence
<220> FEATURE:
<223> OTHER INFORMATION: MsrB/His tag/linker

<400> SEQUENCE: 29

```
atgggcagca gccatcatca tcatcatcac agcagcggcc tggtgccgcg cggcagccat    60
atgaaagcgg caacgtataa aaaaccgagt gacgccgaac tcaaacgcac cctgaccgaa   120
gagcaatacc aagtgaccca aaacagcgcg accgaatacg ccttcagcca cgaatacgac   180
catttgttca aacccggcat ttatgtggac gttgtcagcg gcgaacccct gttcagctcc   240
gccgacaaat atgattccgg ctgcggctgg ccgagcttca cgcgcccgat tgatgcaaaa   300
tccgttaccg aacacgatga tttcagcttc aatatgcgcc gcaccgaagt cagaagccgc   360
gccgccgatt cgcacttggg acacgtcttc cccgacggcc ccgcgacaa aggcggactg   420
cgctactgca tcaacggcgc gagcttgaaa ttcatcccgc tggaacaaat ggacgcggca   480
ggctacggcg cgttgaaggg caaagtgaaa taa                                 513
```

<210> SEQ ID NO 30
<211> LENGTH: 170
<212> TYPE: PRT
<213> ORGANISM: Artificial Sequence
<220> FEATURE:
<223> OTHER INFORMATION: MsrB/His tag/linker

<400> SEQUENCE: 30

```
Met Gly Ser Ser His His His His His His Ser Ser Gly Leu Val Pro
1               5                   10                  15
Arg Gly Ser His Met Lys Ala Ala Thr Tyr Lys Lys Pro Ser Asp Ala
            20                  25                  30
Glu Leu Lys Arg Thr Leu Thr Glu Glu Gln Tyr Gln Val Thr Gln Asn
        35                  40                  45
Ser Ala Thr Glu Tyr Ala Phe Ser His Glu Tyr Asp His Leu Phe Lys
    50                  55                  60
Pro Gly Ile Tyr Val Asp Val Val Ser Gly Glu Pro Leu Phe Ser Ser
65                  70                  75                  80
Ala Asp Lys Tyr Asp Ser Gly Cys Gly Trp Pro Ser Phe Thr Arg Pro
                85                  90                  95
Ile Asp Ala Lys Ser Val Thr Glu His Asp Asp Phe Ser Phe Asn Met
            100                 105                 110
Arg Arg Thr Glu Val Arg Ser Arg Ala Ala Asp Ser His Leu Gly His
        115                 120                 125
Val Phe Pro Asp Gly Pro Arg Asp Lys Gly Gly Leu Arg Tyr Cys Ile
    130                 135                 140
Asn Gly Ala Ser Leu Lys Phe Ile Pro Leu Glu Gln Met Asp Ala Ala
145                 150                 155                 160
Gly Tyr Gly Ala Leu Lys Gly Lys Val Lys
                165                 170
```

<210> SEQ ID NO 31
<211> LENGTH: 153
<212> TYPE: PRT
<213> ORGANISM: Artificial Sequence
<220> FEATURE:
<223> OTHER INFORMATION: Recombinant MsrB

<400> SEQUENCE: 31

```
Gly Ser His Met Lys Ala Ala Thr Tyr Lys Lys Pro Ser Asp Ala Glu
1               5                   10                  15
Leu Lys Arg Thr Leu Thr Glu Glu Gln Tyr Gln Val Thr Gln Asn Ser
            20                  25                  30
Ala Thr Glu Tyr Ala Phe Ser His Glu Tyr Asp His Leu Phe Lys Pro
```

```
                35                  40                  45
Gly Ile Tyr Val Asp Val Val Ser Gly Glu Pro Leu Phe Ser Ser Ala
         50                  55                  60

Asp Lys Tyr Asp Ser Gly Cys Gly Trp Pro Ser Phe Thr Arg Pro Ile
 65                  70                  75                  80

Asp Ala Lys Ser Val Thr Glu His Asp Asp Phe Ser Phe Asn Met Arg
                 85                  90                  95

Arg Thr Glu Val Arg Ser Arg Ala Ala Asp Ser His Leu Gly His Val
            100                 105                 110

Phe Pro Asp Gly Pro Arg Asp Lys Gly Gly Leu Arg Tyr Cys Ile Asn
        115                 120                 125

Gly Ala Ser Leu Lys Phe Ile Pro Leu Glu Gln Met Asp Ala Ala Gly
    130                 135                 140

Tyr Gly Ala Leu Lys Gly Lys Val Lys
145                 150
```

<210> SEQ ID NO 32
<211> LENGTH: 100
<212> TYPE: DNA
<213> ORGANISM: Neisseria meningitidis

<400> SEQUENCE: 32
cagacatgga atcgccgaaa acgtcggcgg taaatgcaaa gctaagcggc ttggaaagcc    60
cggccggctt aaatttctta accaaaaaag gaatacagca                         100

<210> SEQ ID NO 33
<211> LENGTH: 28
<212> TYPE: DNA
<213> ORGANISM: Artificial Sequence
<220> FEATURE:
<223> OTHER INFORMATION: Primer PmeI_For

<400> SEQUENCE: 33
gtttaaacat gaaacaccgt actttctt                                       28

<210> SEQ ID NO 34
<211> LENGTH: 24
<212> TYPE: DNA
<213> ORGANISM: Artificial Sequence
<220> FEATURE:
<223> OTHER INFORMATION: Primer PmeI_Rev

<400> SEQUENCE: 34 aaactttga tgtttcctgt gtgg                                            24

<210> SEQ ID NO 35
<211> LENGTH: 35
<212> TYPE: DNA
<213> ORGANISM: Artificial Sequence
<220> FEATURE:
<223> OTHER INFORMATION: Primer pCTS32_porBPromoter_AflIIFor

<400> SEQUENCE: 35
agtttcctta agcagacatg gaatcgccga aaacg                               35

<210> SEQ ID NO 36
<211> LENGTH: 33
<212> TYPE: DNA
<213> ORGANISM: Artificial Sequence
<220> FEATURE:
<223> OTHER INFORMATION: Primer pCTS32_porBPromoter_PmeIR

<400> SEQUENCE: 36
ttcattgttt aaactgctgt attccttttt tgg                               33

<210> SEQ ID NO 37
<211> LENGTH: 32
<212> TYPE: DNA
<213> ORGANISM: Artificial Sequence
<220> FEATURE:
<223> OTHER INFORMATION: Primer pCTS32_Msr_AflIIFor

<400> SEQUENCE: 37
ctcgagctta agccggcgtt tcctgttttt tc                               32

<210> SEQ ID NO 38
<211> LENGTH: 35
<212> TYPE: DNA
<213> ORGANISM: Artificial Sequence
<220> FEATURE:
<223> OTHER INFORMATION: Primer pCTS32_Msr_SmaIRev

<400> SEQUENCE: 38
tgcggccccg ggttatttca ctttgccctt caacg                            35

<210> SEQ ID NO 39
<211> LENGTH: 498
<212> TYPE: PRT
<213> ORGANISM: Artificial Sequence
<220> FEATURE:
<223> OTHER INFORMATION: Recombinant MsrA/B

<400> SEQUENCE: 39

```
Gly Ser His Met Lys Gly Thr Ala Thr Val Pro His Thr Leu Ser Thr
1               5                   10                  15

Leu Lys Thr Ala Asp Asn Arg Pro Ala Ser Val Tyr Leu Lys Lys Asp
            20                  25                  30

Lys Pro Thr Leu Ile Lys Phe Trp Ala Ser Trp Cys Pro Leu Cys Leu
        35                  40                  45

Ser Glu Leu Gly Gln Ala Glu Lys Trp Ala Gln Asp Ala Lys Phe Ser
    50                  55                  60

Ser Ala Asn Leu Ile Thr Val Ala Ser Pro Gly Phe Leu His Glu Lys
65                  70                  75                  80

Lys Asp Gly Glu Phe Gln Lys Trp Tyr Ala Gly Leu Asn Tyr Pro Lys
                85                  90                  95

Leu Pro Val Val Thr Asp Asn Gly Gly Thr Ile Ala Gln Asn Leu Asn
            100                 105                 110

Ile Ser Val Tyr Pro Ser Trp Ala Leu Ile Gly Lys Asp Gly Asp Val
        115                 120                 125

Gln Arg Ile Val Lys Gly Ser Ile Asn Glu Ala Gln Ala Leu Ala Leu
    130                 135                 140

Ile Arg Asn Pro Asn Ala Asp Leu Gly Ser Leu Lys His Ser Phe Tyr
145                 150                 155                 160

Lys Pro Asp Thr Gln Lys Lys Asp Ser Ala Ile Met Asn Thr Arg Thr
                165                 170                 175

Ile Tyr Leu Ala Gly Gly Cys Phe Trp Gly Leu Glu Ala Tyr Phe Gln
            180                 185                 190

Arg Ile Asp Gly Val Val Asp Ala Val Ser Gly Tyr Ala Asn Gly Asn
        195                 200                 205

Thr Glu Asn Pro Ser Tyr Glu Asp Val Ser Tyr Arg His Thr Gly His
    210                 215                 220
```

```
Ala Glu Thr Val Lys Val Thr Tyr Asp Ala Asp Lys Leu Ser Leu Asp
225                 230                 235                 240

Asp Ile Leu Gln Tyr Tyr Phe Arg Val Val Asp Pro Thr Ser Leu Asn
            245                 250                 255

Lys Gln Gly Asn Asp Thr Gly Thr Gln Tyr Arg Ser Gly Val Tyr Tyr
            260                 265                 270

Thr Asp Pro Ala Glu Lys Ala Val Ile Ala Ala Leu Lys Arg Glu
        275                 280                 285

Gln Gln Lys Tyr Gln Leu Pro Leu Val Val Glu Asn Glu Pro Leu Lys
        290                 295                 300

Asn Phe Tyr Asp Ala Glu Glu Tyr His Gln Asp Tyr Leu Ile Lys Asn
305                 310                 315                 320

Pro Asn Gly Tyr Cys His Ile Asp Ile Arg Lys Ala Asp Glu Pro Leu
                325                 330                 335

Pro Gly Lys Thr Lys Ala Ala Pro Gln Gly Lys Gly Phe Asp Ala Ala
            340                 345                 350

Thr Tyr Lys Lys Pro Ser Asp Ala Glu Leu Lys Arg Thr Leu Thr Glu
        355                 360                 365

Glu Gln Tyr Gln Val Thr Gln Asn Ser Ala Thr Glu Tyr Ala Phe Ser
370                 375                 380

His Glu Tyr Asp His Leu Phe Lys Pro Gly Ile Tyr Val Asp Val Val
385                 390                 395                 400

Ser Gly Glu Pro Leu Phe Ser Ser Ala Asp Lys Tyr Asp Ser Gly Cys
                405                 410                 415

Gly Trp Pro Ser Phe Thr Arg Pro Ile Asp Ala Lys Ser Val Thr Glu
            420                 425                 430

His Asp Asp Phe Ser Phe Asn Met Arg Arg Thr Glu Val Arg Ser Arg
            435                 440                 445

Ala Ala Asp Ser His Leu Gly His Val Phe Pro Asp Gly Pro Arg Asp
450                 455                 460

Lys Gly Gly Leu Arg Tyr Cys Ile Asn Gly Ala Ser Leu Lys Phe Ile
465                 470                 475                 480

Pro Leu Glu Gln Met Asp Ala Ala Gly Tyr Gly Ala Leu Lys Gly Lys
                485                 490                 495

Val Lys

<210> SEQ ID NO 40
<211> LENGTH: 506
<212> TYPE: PRT
<213> ORGANISM: Artificial Sequence
<220> FEATURE:
<223> OTHER INFORMATION: Residues 17-522 of SEQ ID NO: 1

<400> SEQUENCE: 40

Leu Ala Leu Gly Ala Cys Ser Pro Lys Ile Val Asp Ala Gly Thr Ala
1               5                   10                  15

Thr Val Pro His Thr Leu Ser Thr Leu Lys Thr Ala Asp Asn Arg Pro
                20                  25                  30

Ala Ser Val Tyr Leu Lys Lys Asp Lys Pro Thr Leu Ile Lys Phe Trp
            35                  40                  45

Ala Ser Trp Cys Pro Leu Cys Leu Ser Glu Leu Gly Gln Ala Glu Lys
        50                  55                  60

Trp Ala Gln Asp Ala Lys Phe Ser Ser Ala Asn Leu Ile Thr Val Ala
65                  70                  75                  80
```

-continued

Ser Pro Gly Phe Leu His Glu Lys Lys Asp Gly Glu Phe Gln Lys Trp
             85                  90                  95

Tyr Ala Gly Leu Asn Tyr Pro Lys Leu Pro Val Val Thr Asp Asn Gly
            100                 105                 110

Gly Thr Ile Ala Gln Asn Leu Asn Ile Ser Val Tyr Pro Ser Trp Ala
            115                 120                 125

Leu Ile Gly Lys Asp Gly Asp Val Gln Arg Ile Val Lys Gly Ser Ile
            130                 135                 140

Asn Glu Ala Gln Ala Leu Ala Leu Ile Arg Asn Pro Asn Ala Asp Leu
145                 150                 155                 160

Gly Ser Leu Lys His Ser Phe Tyr Lys Pro Asp Thr Gln Lys Lys Asp
                165                 170                 175

Ser Ala Ile Met Asn Thr Arg Thr Ile Tyr Leu Ala Gly Gly Cys Phe
                180                 185                 190

Trp Gly Leu Glu Ala Tyr Phe Gln Arg Ile Asp Gly Val Val Asp Ala
                195                 200                 205

Val Ser Gly Tyr Ala Asn Gly Asn Thr Glu Asn Pro Ser Tyr Glu Asp
210                 215                 220

Val Ser Tyr Arg His Thr Gly His Ala Glu Thr Val Lys Val Thr Tyr
225                 230                 235                 240

Asp Ala Asp Lys Leu Ser Leu Asp Asp Ile Leu Gln Tyr Tyr Phe Arg
                245                 250                 255

Val Val Asp Pro Thr Ser Leu Asn Lys Gln Gly Asn Asp Thr Gly Thr
                260                 265                 270

Gln Tyr Arg Ser Gly Val Tyr Tyr Thr Asp Pro Ala Glu Lys Ala Val
                275                 280                 285

Ile Ala Ala Ala Leu Lys Arg Glu Gln Gln Lys Tyr Gln Leu Pro Leu
                290                 295                 300

Val Val Glu Asn Glu Pro Leu Lys Asn Phe Tyr Asp Ala Glu Glu Tyr
305                 310                 315                 320

His Gln Asp Tyr Leu Ile Lys Asn Pro Asn Gly Tyr Cys His Ile Asp
                325                 330                 335

Ile Arg Lys Ala Asp Glu Pro Leu Pro Gly Lys Thr Lys Ala Ala Pro
                340                 345                 350

Gln Gly Lys Gly Phe Asp Ala Ala Thr Tyr Lys Lys Pro Ser Asp Ala
                355                 360                 365

Glu Leu Lys Arg Thr Leu Thr Glu Glu Gln Tyr Gln Val Thr Gln Asn
370                 375                 380

Ser Ala Thr Glu Tyr Ala Phe Ser His Glu Tyr Asp His Leu Phe Lys
385                 390                 395                 400

Pro Gly Ile Tyr Val Asp Val Val Ser Gly Glu Pro Leu Phe Ser Ser
                405                 410                 415

Ala Asp Lys Tyr Asp Ser Gly Cys Gly Trp Pro Ser Phe Thr Arg Pro
                420                 425                 430

Ile Asp Ala Lys Ser Val Thr Glu His Asp Asp Phe Ser Phe Asn Met
                435                 440                 445

Arg Arg Thr Glu Val Arg Ser Arg Ala Ala Asp Ser His Leu Gly His
450                 455                 460

Val Phe Pro Asp Gly Pro Arg Asp Lys Gly Gly Leu Arg Tyr Cys Ile
465                 470                 475                 480

```
Asn Gly Ala Ser Leu Lys Phe Ile Pro Leu Glu Gln Met Asp Ala Ala
            485                 490                 495

Gly Tyr Gly Ala Leu Lys Gly Lys Val Lys
            500             505
```

COMPOSITIONS, METHODS AND USES FOR ELICITING AN IMMUNE RESPONSE

PRIORITY AND CROSS REFERENCE TO RELATED APPLICATIONS

This application is the U.S. National Stage Application under 35 U.S.C. § 371 of International Application No. PCT/AU2019/051418, filed Dec. 20, 2019, designating the U.S. and published in English as WO 2020/124159 A1 on Jun. 25, 2020, which claims the benefit of Australian Patent Application No. AU 2018904887, filed Dec. 21, 2018. Any and all applications for which a foreign or a domestic priority is claimed is/are identified in the Application Data Sheet filed herewith and is/are hereby incorporated by reference in their entirety under 37 C.F.R. § 1.57.

SEQUENCE LISTING IN ELECTRONIC FORMAT

The present application is being filed along with an Electronic Sequence Listing as an ASCII text file via EFS-Web. The Electronic Sequence Listing is provided as a file entitled DAVI563003APCSEQLIST.txt, created and last saved on Jun. 18, 2021, which is 65,007 bytes in size, which is replaced by a Replacement Electronic Sequence Listing submitted herewith as a file entitled DAVI563003A- PCRE-PLACEMENTSEQLIST.txt, which is 69,472 bytes in size and was created on Sep. 23, 2024, which is replaced by a Replacement Electronic Sequence Listing submitted herewith as a file entitled DAVI563003APC2NDREPLACE-MENTSEQLIST.txt, which is 69,488 bytes in size and was created on Apr. 2, 2025. The information in the Electronic Sequence Listing is incorporated herein by reference in its entirety.

RELATED APPLICATIONS

This application claims priority to Australian Provisional Application No. 2018904887 entitled "Compositions, methods and uses for eliciting an immune response" filed 21 Dec. 2018, the contents of which are incorporated herein by reference in their entirety.

FIELD OF THE INVENTION

This invention relates generally to polynucleotides, polypeptides, compositions, methods and uses for eliciting an immune response to *Neisseria*, methods for immunizing a subject against a *Neisseria* infection, and methods for preventing and/or treating a *Neisseria* infection in a subject. More particularly, the invention relates to antigenic *Neisseria* polypeptides and encoding polynucleotides, and related uses and methods, including use for preparing compositions and medicaments for eliciting an immune response to *Neisseria*, for immunizing a subject against a *Neisseria* infection, and for preventing and/or treating a *Neisseria* infection in a subject. The invention also relates to methods for producing therapeutic anti-*Neisseria* antigen-binding molecules, and therapeutic uses of those antigen-binding molecules.

BACKGROUND OF THE INVENTION

*Neisseria gonorrhoeae* is a Gram-negative, obligate human pathogen that infects human mucosal surfaces and causes the sexually transmitted infection gonorrhoea. It is estimated that there are more than 106 million cases of gonorrhoea worldwide each year. Symptomatic gonococcal infection typically presents as urethritis in males and cervicitis in females, although infection of the rectum, pharynx and eye also occur in both sexes. Furthermore, asymptomatic infections are common and can occur in up to 80% of infected females and 40% of infected males. If left untreated, gonorrhoea can lead to severe sequelae, such as pelvic inflammatory disease, adverse pregnancy outcomes, neonatal complications, and infertility, and can also increase the risk of acquiring and transmitting HIV (reviewed in Edwards et al., 2016, Crit Rev Microbiol 42(6), 928-941).

The recent emergence of multidrug resistant strains of *N. gonorrhoeae* has generated a major public health challenge. Combination therapy of azithromycin and ceftriaxone is now the last line of defense for treating *gonorrhoeae*, however, isolates with high-level resistance to the expanded-spectrum cephalosporins, ceftriaxone and cefixime have been identified globally, highlighting the requirement for new therapeutic approaches or for a vaccine. Various potential vaccine targets have been described, however there are several challenges to developing a gonococcal vaccine, including, for example, the lack of protective immunity following infection, as well as the high level of phase and antigenic variation of *N. gonorrhoeae* surface antigens (reviewed in Edwards et al., 2016, Crit Rev Microbiol 42(6), 928-941 and Rice et al., 2017, Annu Rev Microbiol 71, 665-686). Ideally, vaccine antigens should be conserved, immunogenic, and be able to induce functional antibodies that are able to mediate bactericidal or opsonophagocytic killing, and/or that are able to block an important function of *N. gonorrhoeae* (Edwards et al., 2016, Crit Rev Microbiol 42(6), 928-941). Notably though, effective vaccines do not necessarily need to completely protect individuals from infection. Vaccines with partial or moderate efficacy (e.g. 50% or even 20% efficacy) are likely to reduce transmission of *N. gonorrhoeae* and have a substantive impact on gonococcal prevalence and disease sequelae (Craig et al. 2015, Vaccine. 33(36):4520-4525).

SUMMARY OF THE INVENTION

The present invention is predicated in part on the surprising finding that contrary to the generally held view that methionine sulfoxide reductases are located intracellularly in Gram-negative bacteria, the methionine sulfoxide reductase (MsrA/B) of *Neisseria gonorrhoeae* is exposed on the surface of these bacteria. Moreover, MsrA/B from *N. gonorrhoeae* is present, highly conserved and expressed in all *N. gonorrhoeae* strains investigated in the present studies and is immunogenic. Of note, the present inventors found that MsrA/B can be used to elicit antibodies to *N. gonorrhoeae*, which can kill *N. gonorrhoeae* via both serum bactericidal activity and opsonophagocytic activity. In addition, the elicited antibodies can inhibit the activity of MsrA/B by inhibiting binding to its substrate. The inventors also determined that MsrA/B of *Neisseria meningitidis*, which has 98% sequence identity to MsrA/B of *N. gonorrhoeae*, is also surface-exposed. Accordingly, as determined for the first time herein, MsrA/B is a *Neisseria* vaccine candidate and can be used to elicit an immune response (including a protective immune response) to *Neisseria*, and in particular *N. gonorrhoeae* and *N. meningitidis*. MsrA/B can therefore also be used to prepare vaccine compositions to immunize a subject against *Neisseria*, and in particular *N. gonorrhoeae* and *N. meningitidis*.

Accordingly, in one aspect, the disclosure provides a composition, comprising: a) a recombinant MsrA/B polypeptide or a recombinant polynucleotide encoding the MsrA/B polypeptide, and an adjuvant; or b) a viral vector comprising a polynucleotide encoding the MsrA/B polypeptide; wherein the MsrA/B polypeptide comprises an amino acid sequence set forth in any one of SEQ ID NOs: 1-12, 15, 27, 28, 30, 31 and 39 or a sequence having at least 95%, 96%, 97%, 98% or 99% identity to the sequence set forth in any one of SEQ ID NOs:1-12, 15, 27, 28, 30, 31 and 39, or is an antigenic fragment of a polypeptide comprising an amino acid sequence set forth in any one of SEQ ID NOs:11-12, 15, 27, 28, 30, 31 and 39 or a sequence having at least 95%, 96%, 97%, 98% or 99% identity to the sequence set forth in any one of SEQ ID NOs: 1-12, 15, 27, 28, 30, 31 and 39.

In some embodiments, the antigenic fragment comprises at least or about 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 340, 350, 360, 370, 380, 390, 400, 410, 420, 430, 440, 450, 460, 470, 480, 490, 500 or 510 amino acid residues.

In particular embodiments, the antigenic fragment lacks all or a portion of the putative signal sequence set forth in amino acids corresponding to amino acids 1-31 of SEQ ID NO:1; is N-terminally truncated compared to a full-length MsrA/B polypeptide by at least or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids; comprises all or a portion of the MsrA domain; comprises all or a portion of amino acids corresponding to amino acids 181-362 or 199-354 of SEQ ID NO: 1; comprises all or a portion of the MsrB domain; comprises all or a portion of amino acids corresponding to amino acids 375-522 or 383-506 of SEQ ID NO: 1; comprises all or a portion of the thioredoxin domain; and/or comprises all or a portion of amino acids corresponding to amino acids 17-174 of SEQ ID NO: 1. In further embodiments, the MsrA/B polypeptide is linked to a T helper cell epitope and/or a carrier protein, such as tetanus toxoid, diphtheria toxoid or CRM-197.

The adjuvant in the composition may be, for example, an aluminium salt, a water-in-oil emulsion, an oil-in-water emulsion (e.g. one that comprises squalene), 3-<9-desacyl-4'-monophosphoryl lipid A (MPL), an adjuvant comprising MPL, a toll like receptor (TLR) agonist (e.g. a TLR1, TLR2, TLR3, TLR4, TLR5, TLR7, TLR8, TLR9 and/or TLR10 agonist), a saponin-based adjuvant (e.g. one that comprises saponins or saponin derivatives from *Quillaja saponaria, Panax ginseng Panax notoginseng, Panax quinquefolium, Platycodon grandiflorum, Polygala senega, Polygala tenuifolia, Quillaja brasiliensis, Astragalus membranaceus* or *Achyranthes bidentate*; and/or one that is an iscom or iscom matrix), a liposome, a virosome, a virus-like particle (VLP), an outer membrane vesicle (OMV; e.g. a *N. meningitidis, N. gonorrhoeae, E. coli* or *P. aeruginosa* OMV), a cytokine, a chemokine and a growth factor.

In some examples, the composition may further comprise an additional antigen, such as a *N. gonorrhoeae* antigen (e.g. PilC, PilQ, Opa, AniA, TdfJ, PorB, Lst, TbpB, TbpA, OmpA, OpcA, MetQ, MtrE or the 2C7 epitope or epitope mimetic), or a *N. meningitidis* antigen (e.g. NadA, fHbp, NHBA, GNA1030, GNA2091, HmbR, NspA, Nhha, App, Omp85, TbpA, TbpB, Cu,Zn-superoxide dismutase or a capsular polysaccharides or oligosaccharides from menin-gococcal serogroup A, C, W135 or Y). In particular examples, the composition comprises 2, 3, 4, 5 or more additional antigens.

In one embodiment, the viral vector in the composition is selected from a retrovirus (e.g., lentivirus), adenovirus, adeno-associated virus (AAV), herpes virus (e.g., Cytomegalovirus (CMV)), alphavirus, astrovirus, coronavirus, orthomyxovirus, papovavirus, paramyxovirus (e.g., Sendai virus), parvovirus, picornavirus, poxvirus (e.g., vaccinia virus), and togavirus vector.

The composition may further comprise a pharmaceutically-acceptable carrier.

In a further aspect, the present disclosure provides a method for eliciting an immune response to *N. gonorrhoeae* and/or *N. meningitidis* in a subject, comprising administering to the subject a recombinant MsrA/B polypeptide or a recombinant polynucleotide encoding the MsrA/B polypeptide; wherein the MsrA/B polypeptide comprises an amino acid sequence set forth in any one of SEQ ID NOs:1-12, 15, 27, 28, 30, 31 and 39 or a sequence having at least 95%, 96%, 97%, 98% or 99% identity to the sequence set forth in any one of SEQ ID NOs:1-12, 15, 27, 28, 30, 31 and 39 or is an antigenic fragment of a polypeptide comprising an amino acid sequence set forth in any one of SEQ ID NOs:1-12, 15, 27, 28, 30, 31 and 39 or a sequence having at least 95%, 96%, 97%, 98% or 99% identity to the sequence set forth in any one of SEQ ID NOs:1-12, 15, 27, 28, 30, 31 and 39; and administration results in the generation of a protective immune response to *N. gonorrhoeae* and/or *N. meningitidis*.

In another aspect, provided is a method for immunising a subject against *N. gonorrhoeae* and/or *N. meningitidis*, comprising administering to the subject a recombinant MsrA/B polypeptide or a recombinant polynucleotide encoding the MsrA/B polypeptide; wherein the MsrA/B polypeptide comprises an amino acid sequence set forth in any one of SEQ ID NOs: 1-12, 15, 27, 28, 30, 31 and 39 or a sequence having at least 95%, 96%, 97%, 98% or 99% identity to the sequence set forth in any one of SEQ ID NOs:1-12, 15, 27, 28, 30, 31 and 39 or is an antigenic fragment of a polypeptide comprising an amino acid sequence set forth in any one of SEQ ID NOs: 1-12, 15, 27, 28, 30, 31 and 39 or a sequence having at least 95%, 96%, 97%, 98% or 99% identity to the sequence set forth in any one of SEQ ID NOs: 1-12, 15, 27, 28, 30, 31 and 39; and administration results in the generation of a protective immune response to *N. gonorrhoeae* and/or *N. meningitidis*.

A further aspect of the present disclosure provides a method for inhibiting the development or progression of a *N. gonorrhoeae* and/or *N. meningitidis* infection in a subject, comprising administering to the subject a recombinant MsrA/B polypeptide or a recombinant polynucleotide encoding the MsrA/B polypeptide; wherein the MsrA/B polypeptide comprises an amino acid sequence set forth in any one of SEQ ID NOs: 1-12, 15, 27, 28, 30, 31 and 39 or a sequence having at least 95%, 96%, 97%, 98% or 99% identity to the sequence set forth in any one of SEQ ID NOs: 1-12, 15, 27, 28, 30, 31 and 39 or is an antigenic fragment of a polypeptide comprising an amino acid sequence set forth in any one of SEQ ID NOs:1-12, 15, 27 and 29 or a sequence having at least 95%, 96%, 97%, 98% or 99% identity to the sequence set forth in any one of SEQ ID NOs: 1-12, 15, 27, 28, 30, 31 and 39; and administration results in the generation of a protective immune response to *N. gonorrhoeae* and/or *N. meningitidis*.

In some embodiments of the methods, administration elicits a protective humoral response to *N. gonorrhoeae* and/or *N. meningitidis*. The protective humoral immune response may comprise, for example, anti-MsrA/B antibodies that are bactericidal, opsonophagocytic and/or inhibit a function of MsrA/B. In particular examples, the protective humoral immune response comprises anti-MsrA/B IgG1, IgG2a, IgG2b, IgG3, IgM and/or IgA antibodies.

In particular embodiments of the methods, the antigenic fragment comprises at least or about 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 340, 350, 360, 370, 380, 390, 400, 410, 420, 430, 440, 450, 460, 470, 480, 490, 500 or 510 amino acid residues. In some examples, the antigenic fragment lacks all or a portion of the putative signal sequence set forth in amino acids corresponding to amino acids 1-31 of SEQ ID NO: 1; is N-terminally truncated compared to a full-length MsrA/B polypeptide by at least or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids; comprises all or a portion of the MsrA domain; comprises all or a portion of amino acids corresponding to amino acids 181-362 or 199-354 of SEQ ID NO:1; comprises all or a portion of the MsrB domain; comprises all or a portion of amino acids corresponding to amino acids 375-522 or 383-506 of SEQ ID NO: 1; comprises all or a portion of the thioredoxin domain; and/or comprises all or a portion of amino acids corresponding to amino acids 17-174 of SEQ ID NO: 1. In further embodiments, the MsrA/B polypeptide is linked to a T helper cell epitope and/or a carrier protein, such as tetanus toxoid, diphtheria toxoid or CRM-197.

In some embodiments, the methods further comprise administering an adjuvant. The adjuvant in the composition may be, for example, an aluminium salt, a water-in-oil emulsion, an oil-in-water emulsion (e.g. one that comprises squalene), 3-<9-desacyl-4'-monophosphoryl lipid A (MPL), an adjuvant comprising MPL, a toll like receptor (TLR) agonist (e.g. a TLR1, TLR2, TLR3, TLR4, TLR5, TLR7, TLR8, TLR9 and/or TLR10 agonist), a saponin-based adjuvant (e.g. one that comprises saponins or saponin derivatives from *Quillaja saponaria, Panax ginseng Panax notoginseng, Panax quinquefolium, Platycodon grandiflorum, Polygala senega, Polygala tenuifolia, Quillaja brasiliensis, Astragalus membranaceus* or *Achyranthes bidentate*; and/or one that is an iscom or iscom matrix), a liposome, a virosome, a virus-like particle (VLP), an outer membrane vesicle (OMV; e.g. a *N. meningitidis, N. gonorrhoeae, E. coli* or *P. aeruginosa* OMV), a cytokine, a chemokine and a growth factor.

In one example, the methods further includes administering an addition antigen, such as a *N. gonorrhoeae* antigen (e.g. PilC, PilQ, Opa, AniA, TdfJ, PorB, Lst, TbpB, TbpA, OmpA, OpcA, MetQ, MtrE or the 2C7 epitope or epitope mimetic), or a *N. meningitidis* antigen (e.g. NadA, fHbp, NHBA, GNA1030, GNA2091, HmbR, NspA, Nhha, App, Omp85, TbpA, TbpB, Cu,Zn-superoxide dismutase or a capsular polysaccharides or oligosaccharides from meningococcal serogroup A, C, W135 or Y). In particular examples, 2, 3, 4, 5 or more additional antigens are administered.

In some examples of the methods, the polynucleotide encoding the MsrA/B polypeptide is comprised within a viral vector, e.g. a retrovirus (e.g., lentivirus), adenovirus, adeno-associated virus (AAV), herpes virus (e.g., Cytomegalovirus (CMV)), alphavirus, astrovirus, coronavirus, orthomyxovirus, papovavirus, paramyxovirus (e.g., Sendai virus), parvovirus, picornavirus, poxvirus (e.g., vaccinia virus), or togavirus vector.

In one example, administration is via a subcutaneous, intraperitoneal, intravenous, intramuscular, intradermal, intranasal or oral route.

Also provided is a method for treating a *N. gonorrhoeae* and/or *N. meningitidis* infection in a subject, comprising administering to the subject an antigen-binding molecule specific for a MsrA/B polypeptide; wherein the MsrA/B polypeptide comprises an amino acid sequence set forth in any one of SEQ ID NOs:1-12, 15, 27, 28, 30, 31 and 39 or a sequence having at least 95%, 96%, 97%, 98% or 99% identity to the sequence set forth in any one of SEQ ID NOs: 1-12, 15, 27, 28, 30, 31 and 39, or is an antigenic fragment of a polypeptide comprising an amino acid sequence set forth in any one of SEQ ID NOs:1-12, 15, 27, 28, 30, 31 and 39 or a sequence having at least 95%, 96%, 97%, 98% or 99% identity to the sequence set forth in any one of SEQ ID NOs:1-12, 15, 27, 28, 30, 31 and 39.

In some embodiments, the antigen-binding molecule is an IgG1, IgG2a, IgG2b, IgG3 or IgA antibody. In further embodiments, the antigen-binding molecule is a single-chain Fv (scFv), Fab, Fab', F(ab')2, Fv, dsFv, diabody, Fd, or Fd' fragment. The antibodies may be, for example, bactericidal, opsonophagocytic and/or inhibitory of a function of MsrA/B.

Also provided is a use of a composition described above and herein for the preparation of a medicament for eliciting an immune response to *N. gonorrhoeae* and/or *N. meningitidis* in a subject, immunising a subject against *N. gonorrhoeae* and/or *N. meningitidis*, inhibiting the development or progression of a *N. gonorrhoeae* and/or *N. meningitidis* infection in a subject, and/or treating or preventing a *N. gonorrhoeae* and/or *N. meningitidis* infection in a subject.

A further aspect of the disclosure provides a use of a recombinant MsrA/B polypeptide or a recombinant polynucleotide encoding the MsrA/B polypeptide for the preparation of a medicament for eliciting an immune response to *N. gonorrhoeae* and/or *N. meningitidis* in a subject, immunising a subject against *N. gonorrhoeae* and/or *N. meningitidis*, inhibiting the development or progression of a *N. gonorrhoeae* and/or *N. meningitidis* infection in a subject, and/or for treating or preventing a *N. gonorrhoeae* and/or *N. meningitidis* infection in a subject; wherein the MsrA/B polypeptide comprises an amino acid sequence set forth in any one of SEQ ID NOs: 1-12, 15, 27, 28, 30, 31 and 39 or a sequence having at least 95%, 96%, 97%, 98% or 99% identity to the sequence set forth in any one of SEQ ID NOs:1-12, 15, 27, 28, 30, 31 and 39 or is an antigenic fragment of a polypeptide comprising an amino acid sequence set forth in any one of SEQ ID NOs:1-12, 15, 27, 28, 30, 31 and 39 or a sequence having at least 95%, 96%, 97%, 98% or 99% identity to the sequence set forth in any one of SEQ ID NOs: 1-12, 15, 27, 28, 30, 31 and 39.

DETAILED DESCRIPTION OF THE INVENTION

1. Definitions

Figure 1:
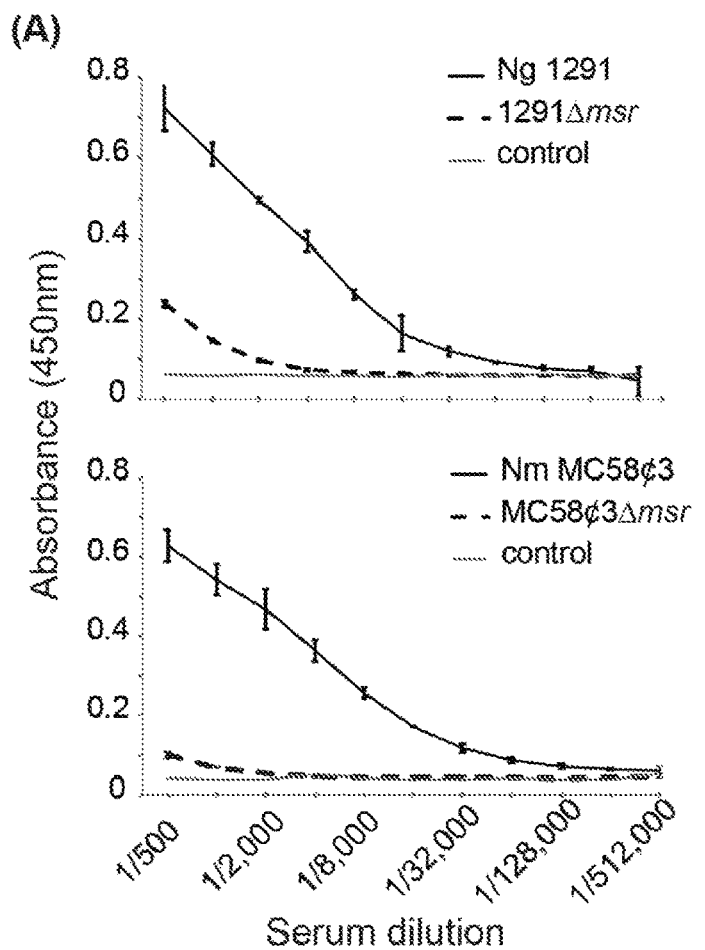
FIG. 1 is a graphical and photographic representation showing surface localization of MsrA/B. (A) Whole cell enzyme-linked immunosorbent assay (ELISA) of the wild type (WT) and msr::kan mutant (Δmsr) strains of *N. gonorrhoeae* 1291 and *N. meningitidis* MC58¢3, with anti-MsrA/B antibodies. The negative control containing secondary antibody only (control), is also shown. The graph shows the average absorbance at 450 nm from three independent replicates, +/− one standard deviation. (B) Western blot analysis of trypsin treated (20 μg, 10 μg) and untreated (0 μg) whole cell *N. gonorrhoeae* 1291 and *N. meningitidis* MC58¢3, probed with antibodies to MsrA/B, the meningococcal surface protein PorA, and the intracellular protein GNA2091. No significant differences were seen in CFUs/ml at t0 vs. 60 mins from samples taken at time 0 and 60 min (two-tailed unpaired Student's t-test p>1.5; data not shown), indicating that no cell lysis occurred during the assay.
Figure 1:
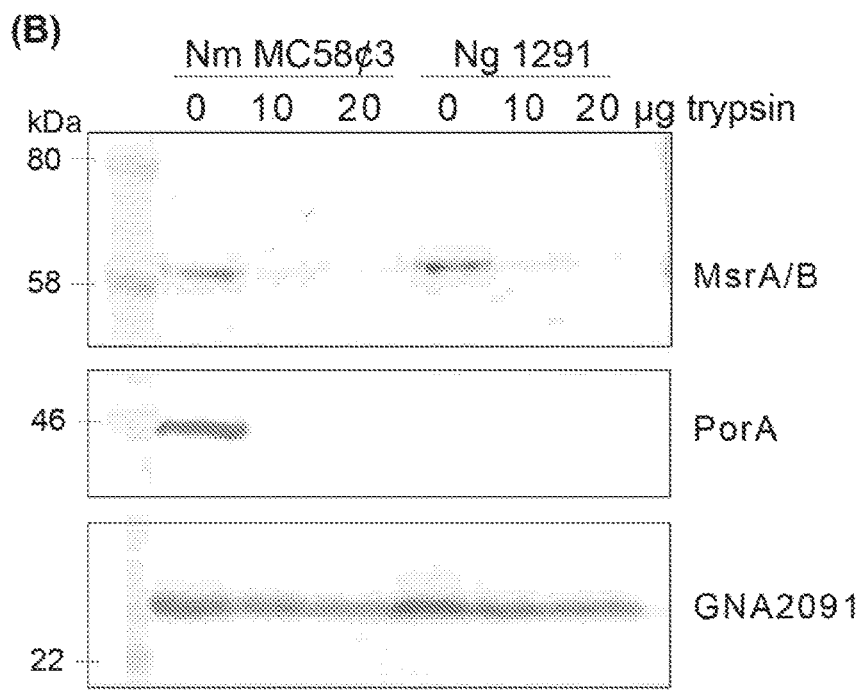

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The singular terms "a", "an" and "the" include plural referents unless context clearly indicates otherwise. It is further to be understood that all base sizes or amino acid sizes, and all molecular weight or molecular mass values, given for nucleic acids or polypeptides are approximate, and are provided for description.

As used herein, "and/or" refers to and encompasses any and all possible combinations of one or more of the associated listed items, as well as the lack of combinations when interpreted in the alternative (or).

The term "antibody", as used herein, means any antigen-binding molecule or molecular complex comprising at least one complementarity determining region (CDR) that binds specifically to or interacts with a particular antigen (e.g., MsrA/B). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (which may be abbreviated as HCVR or $V_H$) and a heavy chain constant region. The heavy chain constant region comprises three domains, $CH_1$, $CH_2$ and $CH_3$. Each light chain comprises a light chain variable region (which may be abbreviated as LCVR or $V_L$) and a light chain constant region. The light chain constant region comprises one domain ($C_{L1}$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of an antibody of the invention (or antigen-binding portion thereof) may be identical to the human germline sequences, or may be naturally or artificially modified. An amino acid consensus sequence may be defined based on a side-by-side analysis of two or more CDRs.

An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called α, δ, ε, γ, and μ, respectively. The subunit structures and three-dimensional configurations of different classes of immunoglobulins are well known.

As used herein, the term "antigen" and its grammatically equivalents expressions (e.g., "antigenic") refer to a compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, and proteins, although for the purposes herein, reference to an antigen is typically with reference to MsrA/B.

The terms "antigen-binding fragment" refers to a part of an antigen-binding molecule that participates in antigen-binding. These terms include any naturally occurring, enzymatically obtainable, synthetic, or genetically engineered polypeptide or glycoprotein that specifically binds an antigen to form a complex. For example, antigen-binding fragments of an antibody may be derived from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, one-armed antibodies, diabodies, triabodies, tetrabodies, minibodies, nanobodies (e.g., monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$—$V_H$, $V_H$—$V_L$ or $V_L$—$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$—$CH_1$; (ii) $V_H$—$CH_2$; (iii) $V_H$—$CH_3$; (iv) $V_H$—$CH_1$—$CH_2$; (v) $V_H$—$CH_1$—$CH_2$—$CH_3$; (vi) $V_H$—$CH_2$—$CH_3$; (vii) $V_H$—$C_L$; (viii) $V_L$—$CH_1$; (ix) $V_L$—$CH_2$, (X) $V_L$—$CH_3$; (xi) $V_L$—$CH_1$—$CH_2$; (xii) $V_L$—$CH_1$—$CH_2$—$CH_3$; (xiii) $V_L$—$CH_2$—$CH_3$; and (xiv) $V_L$—$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)). A multispecific antigen-binding molecule will typically comprise at least two different variable domains, wherein each variable domain is capable of specifically binding to a separate antigen or to a different epitope on the same antigen. Any multispecific antigen-binding molecule format may be adapted for use in the context of an antigen-binding fragment of an antibody of the present disclosure using routine techniques available in the art.

By "antigen-binding molecule" is meant a molecule that has binding affinity for a target antigen. It will be understood that this term extends to immunoglobulins, immunoglobulin fragments and non-immunoglobulin derived protein frameworks that exhibit antigen-binding activity. Representative antigen-binding molecules that are useful in the practice of the present invention include antibodies and their antigen-binding fragments. The term "antigen-binding molecule" includes antibodies and antigen-binding fragments of antibodies.

As used herein the term "antigenic fragment" refers to a fragment of a polypeptide, such as a MsrA/B polypeptide, that is antigenic, i.e., capable of specifically interacting with and being bound by the products of specific humoral or cellular immunity, such as an antibody molecule or T-cell receptor. As would be appreciated, such fragments need not themselves be immunogenic, i.e., capable of eliciting an immune response when administered to a subject alone, but can be immunogenic when administered in conjunction with an appropriate adjuvant or carrier. Antigenic fragments typically comprise at least or about 30, 40, 50, 60, 70, 80, 90, 100, 110, 120, 130, 140, 150, 160, 170, 180, 190, 200 or more amino acids.

The term "bactericidal" refers to the ability of an agent, such as an antibody, to kill bacteria. In relation to bactericidal activity of an antibody, the activity may be complement-dependent or complement-independent. Bactericidal activity of an antibody can be assessed using well-known methods in the art. For example, the serum bactericidal antibody (SBA) assay may be used to assess bactericidal activity of an antibody. In the SBA assay, antibodies (e.g., isolated or in serum) are incubated with target bacteria (e.g., *N. gonorrhoeae* and/or *N. meningitidis*) in the presence of complement (preferably human complement, although baby rabbit complement is often used instead) and killing of the bacteria is assessed at various dilutions of the sera to determine SBA activity.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene or for the final mRNA product of a gene.

Throughout this specification, unless the context requires otherwise, the words "comprise," "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

A "conservative amino acid substitution" is one in which the amino acid residue is replaced with an amino acid residue having a similar side chain. Families of amino acid residues having similar side chains have been defined in the art, which can be generally sub-classified as follows:

TABLE 1

AMINO ACID SUB-CLASSIFICATION

| Sub-classes | Amino acids |
| --- | --- |
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional polypeptide can readily be determined by assaying its activity. Conservative substitutions are shown in Table 2 under the heading of exemplary and preferred substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. After the substitutions are introduced, the variants are screened for biological activity.

TABLE 2

EXEMPLARY AND PREFERRED AMINO ACID SUBSTITUTIONS

| Original Residue | Exemplary Substitutions | Preferred Substitutions |
| --- | --- | --- |
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

As used herein, corresponding amino acid residues (or positions) refer to residues (or positions) that occur at aligned loci within the primary amino acid sequence of a protein. Related or variant polypeptides are aligned by any method known to those of skill in the art. Such methods typically maximize matches, and include methods such as using manual alignments and by using the numerous alignment programs available (for example, BLASTP) and others known to those of skill in the art. By aligning the sequences of polypeptides, one skilled in the art can identify corresponding residues, using conserved and identical amino acid residues as guides. For example, by aligning the sequences of the MsrA/B polypeptide set forth in SEQ ID NO: 1 with another MsrA/B polypeptide, such as one set forth in SEQ ID NO: 8, one of skill in the art can identify corresponding residues using conserved and identical amino acid residues as guides, e.g., Thr31 of SEQ ID NO:1 corresponds to Ala31 of SEQ ID NO: 9.

The terms "decrease", "reduce" or "inhibit" and their grammatical equivalents are all used herein generally to mean a decrease by a statistically significant amount. However, for avoidance of doubt, the terms "decrease", "reduce" or "inhibit" and their grammatical equivalents mean a decrease by at least 10% as compared to a reference level, for example a decrease by at least about 20%, or at least about 30%, or at least about 40%, or at least about 50%, or at least about 60%, or at least about 70%, or at least about 80%, or at least about 90%, where the decrease is less than 100%. In one embodiment, the decrease includes a 100% decrease (e.g., absent level as compared to a reference sample), or any decrease between 10-100% as compared to a reference level.

As used herein, the terms "encode", "encoding" and the like refer to the capacity of a nucleic acid to provide for another nucleic acid or a polypeptide. For example, a nucleic acid sequence is said to "encode" a polypeptide if it can be transcribed and/or translated to produce the polypeptide or if it can be processed into a form that can be transcribed and/or translated to produce the polypeptide. Such a nucleic acid sequence may include a coding sequence or both a coding sequence and a non-coding sequence. Thus, the terms "encode", "encoding" and the like include a RNA product resulting from transcription of a DNA molecule, a protein resulting from translation of a RNA molecule, a protein resulting from transcription of a DNA molecule to form a RNA product and the subsequent translation of the RNA product, or a protein resulting from transcription of a DNA molecule to provide a RNA product, processing of the RNA product to provide a processed RNA product (e.g., mRNA) and the subsequent translation of the processed RNA product.

The term "expression" with respect to a gene sequence refers to transcription of the gene to produce a RNA transcript (e.g., mRNA) and, as appropriate, translation of a resulting mRNA transcript to a protein. Thus, as will be clear from the context, expression of a coding sequence results from transcription and translation of the coding sequence.

The phrase "immunize a subject against" and grammatical variations of, with respect to a Neisseria infection, means to elicit in that subject an immune response that protects (i.e., a "protective immune response"), either partially or completely, the subject from an infection and/or disease caused by Neisseria, and/or inhibits the development and/or progression of an infection and/or disease caused by Neisseria (e.g., N. gonorrhoeae and/or N. meningitidis). Thus, for the purposes of the present disclosure, immunizing a subject against N. gonorrhoeae and/or N. meningitidis means to elicit a protective immune response to N. gonorrhoeae and/or N. meningitidis by administration of a composition, MsrA/B polypeptide or MsrA/B polynucleotide of the disclosure. The term "protective immune response" therefore refers to an immune response that prevents or inhibits, either partially or completely, the development and/or progression of an infection and/or disease caused by Neisseria (e.g., N. gonorrhoeae and/or N. meningitidis). The protective immune response typically comprises a protective humoral immune response, although may also comprise a protective cell-mediated immune response. Protection against Neisseria can be measured epidemiologically e.g., in a clinical trial, but it is convenient to use an indirect measure to confirm that a protective immune response has been generated (such as by a composition, MsrA/B polypeptide or MsrA/B polynucleotide of the disclosure). Protective humoral immune responses can comprise bactericidal antibodies and/or opsonophagocytic antibodies. In some embodiments, a protective humoral immune response is assessed using a SBA assay. In the SBA assay, sera from subjects are incubated with target bacteria (e.g., N. gonorrhoeae and/or N. meningitidis) in the presence of complement (preferably human complement, although baby rabbit complement is often used instead) and killing of the bacteria is assessed at various dilutions of the sera to determine SBA activity. Results observed in the SBA assay can be reinforced by carrying out a competitive SBA assay to provide further indirect evidence of the generation of a protective immune response. In the competitive SBA assay, sera are pre-incubated with the antigen (e.g., the MsrA/B polypeptide) and subsequently incubated with target bacteria in the presence of human complement. Killing of the bacteria is then assessed, and will be reduced or abolished if bactericidal antibodies in the subject's sera bind to the antigens of interest during the pre-incubation phase and are therefore not available to bind to surface antigen on the bacteria. A protective humoral response can also be assessed by performing an opsonophagocytic assay (OPA; also referred to as opsonophagocytic killing assay or OPK assay). In these assays, sera from subjects are incubated with target bacteria (e.g., N. gonorrhoeae and/or N. meningitidis) in the presence of complement (e.g., human complement or baby rabbit complement) and an effector cell, such a phagocytic HL-60 cell (i.e., HL-60 cells that have been differentiated into granulocytes; see e.g., Romero-Steiner et al., 1997, Clin Diagn Lab Immunol. 1997; 4:415-422), fresh polymorphonuclear leukocytes (PMLs) or polymorphonuclear neutrophils (PMN). A viable count of the bacteria is performed before and after the assay so as to determine opsonophagocytic activity.

The term "interaction", including its grammatical equivalents, when referring to an interaction between two molecules, refers to the physical contact of the molecules with one another. Generally, such an interaction results in an activity (which produces a biological effect) of one or both of said molecules. The physical contact typically requires binding or association of the molecules with one another and may involve the formation of an induced magnetic field or paramagnetic field, covalent bond formation, ionic interaction (such as, for example, as occurs in an ionic lattice), a hydrogen bond, or alternatively, a van der Waals interaction such as, for example, a dipole-dipole interaction, dipole-induced dipole interaction, induced dipole-induced dipole interaction, or a repulsive interaction, or any combination of the above forces of attraction.

The term "MsrA/B polypeptide" as used herein refers to a polypeptide comprising an amino acid sequence corresponding to a naturally-occurring N. gonorrhoeae or N. meningitidis MsrA/B polypeptide and variants thereof. This term encompasses, without limitation, full-length MsrA/B polypeptides such as those set forth in SEQ ID NOs:1 and 9-12, and antigenic fragments thereof, including fragments comprising, consisting of or consisting essentially of the MsrA region (set forth, for example, in SEQ ID NO:2 or 3), the MsrB region (set forth, for example, in SEQ ID NO:4 or 5), and/or the thioredoxin domain (set forth, for example, in SEQ ID NO:6). In particular embodiments, MsrA/B polypeptides of the disclosure are antigenic fragments that lack all or a portion of the N-terminal signal peptide, such as a MsrA/B polypeptide set forth in SEQ ID NO:7 or 8. The term "MsrA/B polypeptide" also encompasses, without limitation, polypeptides having an amino acid sequence that shares at least 90%, 91%, 92%, 93%, 94%, 95%, 96%, 97%, 98%, or 99% sequence identity with the sequence set forth in any one of SEQ ID NOs: 1-12 or an antigenic fragment thereof. The term "MsrA/B polypeptide" is also intended to encompass MsrA/B polypeptides that have been chemically modified relative to a naturally-occurring MsrA/B polypeptide. As used herein, a "MsrA/B polynucleotide" refers to a polynucleotide that encodes a MrsA/B polypeptide. In particular embodiments, the MsrA/B polynucleotide and polypeptide are recombinant or synthetic polynucleotides and polypeptides, i.e. have been produced by recombinant technology or by in vitro chemical synthesis.

By "obtained", and grammatical equivalents thereof, is meant to come into possession. Samples so obtained include, for example, nucleic acid extracts or polypeptide extracts isolated or derived from a particular source. For instance, the extract may be isolated directly from a biological fluid or tissue of a subject.

The term "operably connected" or "operably linked" as used herein refers to a juxtaposition wherein the components so described are in a relationship permitting them to function in their intended manner. For example, a regulatory sequence (e.g., a promoter) "operably linked" to a nucleotide sequence of interest (e.g., a coding and/or non-coding sequence) refers to positioning and/or orientation of the control sequence relative to the nucleotide sequence of interest to permit expression of that sequence under conditions compatible with the control sequence. The control sequences need not be contiguous with the nucleotide sequence of interest, so long as they function to direct its expression. Thus, for example, intervening non-coding sequences (e.g., untranslated, yet transcribed, sequences) can be present between a promoter and a coding sequence, and the promoter sequence can still be considered "operably linked" to the coding sequence.

The term "opsonophagocytic" refers to the ability of an antibody or other antigen-binding molecule to bind to an antigen, including an antigen on a bacterium (e.g., MsrA/B on *N. gonorrhoeae* or *N. meningitidis*), and induce or facilitate phagocytosis of the antigen (or bacterium) by an effector cell (e.g., a macrophage). Opsonophagocytic activity of an antibody can be assessed, for example, using an OPA assay, as described above.

As used here, the term "pharmaceutically acceptable" refers to those compounds, agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject agent from one organ, or portion of the body, to another organ, or portion of the body. Each carrier must be "acceptable" in the sense of being compatible with the other ingredients of the formulation and not injurious to the patient.

The term "polynucleotide" is used herein interchangeably with "nucleic acid" to indicate a polymer of nucleosides. Typically, a polynucleotide of this invention is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However, the term encompasses molecules comprising nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and complements of each single-stranded molecule) are provided. "Polynucleotide sequence" as used herein can refer to the polynucleotide material itself and/or to the sequence information (e.g., the succession of letters used as abbreviations for bases) that biochemically characterizes a specific nucleic acid. A polynucleotide sequence presented herein is presented in a 5' to 3' direction unless otherwise indicated.

The terms "polypeptide" as used herein refers to a polymer of amino acids. The terms "protein" and "polypeptide" are used interchangeably herein. A peptide is a relatively short polypeptide, typically between about 2 and 60 amino acids in length. Polypeptides used herein typically contain amino acids such as the 20 L-amino acids that are most commonly found in proteins. However, other amino acids and/or amino acid analogs known in the art can be used. One or more of the amino acids in a polypeptide may be modified, for example, by the addition of a chemical entity such as a carbohydrate group, a phosphate group, a fatty acid group, a linker for conjugation, functionalization, etc. A polypeptide that has a non-polypeptide moiety covalently or noncovalently associated therewith is still considered a "polypeptide". Exemplary modifications include glycosylation and palmitoylation. Polypeptides may be purified from natural sources, produced using recombinant DNA technology, synthesized through chemical means such as conventional solid phase peptide synthesis, etc. The term "polypeptide sequence" or "amino acid sequence" as used herein can refer to the polypeptide material itself and/or to the sequence information (e.g., the succession of letters or three letter codes used as abbreviations for amino acid names) that biochemically characterizes a polypeptide. A polypeptide sequence presented herein is presented in an N-terminal to C-terminal direction unless otherwise indicated.

The term "promoter" is used herein in its ordinary sense to refer to a nucleotide region comprising a sequence capable of initiating transcription of a downstream (3'-direction) gene. An "enhancer" is used herein in its ordinary sense to refer to a nucleotide region comprising a sequence capable of increasing the level of transcription of a gene from a promoter as compared to expression of the gene from the promoter when the enhancer is not present.

"Regulatory sequences", "regulatory elements" and the like refer to nucleotide sequences located upstream (5' non-coding sequences), within, or downstream (3' non-coding sequences) of a coding sequence, and which influence the transcription, RNA processing or stability, or translation of the associated coding sequence, either directly or indirectly. Regulatory elements include enhancers, promoters, translation leader sequences, Rep recognition element, intergenic regions and polyadenylation signal sequences. They include natural and synthetic sequences as well as sequences which may be a combination of synthetic and natural sequences.

The term "recombinant polynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably linked to the nucleotide sequence.

By "recombinant polypeptide" is meant a polypeptide made using recombinant techniques, i.e., through the expression of a recombinant polynucleotide.

The term "sample" as used herein includes any biological specimen that may be extracted, untreated, treated, diluted or concentrated from a subject. Samples may include, without limitation, biological fluids such as whole blood, serum, red blood cells, white blood cells, plasma, saliva, urine, stool (i.e., feces), tears, sweat, sebum, nipple aspirate, ductal lavage, tumor exudates, synovial fluid, ascitic fluid, peritoneal fluid, amniotic fluid, cerebrospinal fluid, lymph, fine needle aspirate, amniotic fluid, any other bodily fluid, cell lysates, cellular secretion products, inflammation fluid, semen and vaginal secretions. Samples may include tissue samples and biopsies, tissue homogenates and the like. Samples can include paraffin-embedded and frozen tissue. The term "sample" also includes untreated or pretreated (or pre-processed) samples. In some embodiments, the sample is an untreated biological sample. In further embodiments, the term "sample" encompasses specimens that have been treated or processed, such as by subsequent culture to grow bacteria.

The term "sequence identity" as used herein refers to the extent that sequences are identical on a nucleotide-by-nucleotide basis or an amino acid-by-amino acid basis over a window of comparison, such as 30, 40, 50, 60, 70, 80, 90, 100, 110, 120, 130, 140, 150, 160, 170, 180, 190, 200 or more nucleotides or amino acids. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

"Similarity" refers to the percentage number of amino acids that are identical or constitute conservative substitutions as defined in Tables 1 and 2 supra. Similarity may be determined using sequence comparison programs such as GAP (Deveraux et al., 1984, *Nucleic Acids Research* 12: 387-395). In this way, sequences of a similar or substantially different length to those cited herein might be compared by insertion of gaps into the alignment, such gaps being determined, for example, by the comparison algorithm used by GAP.

Terms used to describe sequence relationships between two or more polynucleotides or polypeptides include "reference sequence", "comparison window", "sequence identity," "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, WI, USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology", John Wiley & Sons Inc, 1994-1998, Chapter 15.

As used herein, "specifically bind" or "specific for" with respect to an antibody or antigen-binding fragment thereof refers to the ability of the antibody or antigen-binding fragment to form one or more noncovalent bonds with a cognate antigen, by noncovalent interactions between the antibody combining site(s) of the antibody and the antigen (e.g., an MsrA/B polypeptide). The antigen can be an isolated antigen such as an isolated protein or presented on the surface of a cell, such as bacteria. Typically, an antibody that specifically binds to a polypeptide or cell herein is one that binds with an affinity constant ($K_a$) of about or at least $10^7$-$10^{-8}$ M-1 (or a dissociation constant ($K_d$) of or about $10^{-7}$ M (100 nM) or $10^{-8}$ M (10 nM) or less). Affinity constants can be determined by standard kinetic methodology for antibody reactions, for example, immunoassays (e.g., ELISA), or surface plasmon resonance (SPR). Instrumentation and methods for real time detection and monitoring of binding rates are known and are commercially available (e.g., Biacore 2000, Biacore AB, Upsala, Sweden and GE Healthcare Life Sciences).

"Stringent conditions" or "high stringency conditions", as defined herein, can be identified by those that: (1) employ low ionic strength and high temperature for washing, for example 0.015 M sodium chloride/0.0015 M sodium citrate/0.1% sodium dodecyl sulfate at 50.degree. C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/mL), 0.1% SDS, and 10% dextran sulfate at 42° C., with a 10 minute wash at 42° C. in 0.2×SSC (sodium chloride/sodium citrate) followed by a 10 minute high-stringency wash consisting of 0.1×SSC containing EDTA at 55° C.

The term "subject" as used herein refers to an animal, in particular a mammal and more particularly a primate including a lower primate and even more particularly, a human who can benefit from the present disclosure. A subject regardless of whether a human or non-human animal or embryo may be referred to as an individual, subject, animal, patient, host or recipient. For convenience, an "animal" specifically includes livestock animals such as cattle, horses, sheep, pigs, camelids, goats and donkeys, as well as domestic animals, such as dogs and cats. With respect to horses, these include horses used in the racing industry as well as those used recreationally or in the livestock industry. Examples of laboratory test animals include mice, rats, rabbits, guinea pigs and hamsters. Rabbits and rodent animals, such as rats and mice, provide a convenient test system or animal model as do primates and lower primates. In some embodiments, the subject is human.

The term "synthetic polynucleotide" as used herein refers to a polynucleotide formed in vitro by chemical synthesis. In some instances, the polynucleotides are produced by first generating oligonucleotides spanning the desired sequence, such as with solid-phase phosphoramidite chemistry, then "assembling" the oligonucleotides, such as using DNA ligase or polymerase cycling assembly (PCA), to generate the synthetic polynucleotide.

By "synthetic polypeptide" is meant a polypeptide made using in vitro chemical synthesis, such as solid-phase peptide synthesis (SPPS).

As used herein, the terms "treatment", "treating", and the like, refer to obtaining a desired pharmacologic and/or physiologic effect. For the purposes of the present disclosure, where treatment is with respect to an infection and/or disease caused by N. gonorrhoeae and/or N. meningitidis, the effect may be prophylactic in terms of completely or partially preventing an infection and/or disease caused by N. gonorrhoeae and/or N. meningitidis, and/or may be therapeutic in terms of a partial or complete cure of an established infection or disease caused by N. gonorrhoeae and/or N. meningitidis.

By "vector" is meant a polynucleotide molecule, suitably a DNA molecule derived, for example, from a plasmid, bacteriophage, yeast or virus, into which a polynucleotide can be inserted or cloned. A vector may contain one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain any means for assuring self-replication. Alternatively, the vector can be one which, when introduced into the host cell, is integrated into the genome and replicated together with the chromosome(s) into which it has been integrated.

The terms "wild-type", "native" and "naturally-occurring" are used interchangeably herein to refer to a gene or gene product that has the characteristics (e.g. sequence) of that gene or gene product when isolated from a naturally-occurring source.

TABLE 3

BRIEF DESCRIPTION OF THE SEQUENCES

| SEQ ID NO: | Description |
|---|---|
| 1 | Full length MsrA/B from N. gonorrhoeae strain 1291 |
| 2 | MsrA domain (corresponding to aa 181-362 of SEQ ID NO: 1) |
| 3 | MsrA domain (corresponding to aa 199-354 of SEQ ID NO: 1) |
| 4 | MsrB domain (corresponding to aa 375-522 of SEQ ID NO: 1) |
| 5 | MsrB domain (corresponding to aa 383-506 of SEQ ID NO: 1) |
| 6 | Thioredoxin domain (corresponding to aa 17-174 of SEQ ID NO: 1) |
| 7 | MsrA/B fragment lacking the signal sequence (corresponding to aa 32-522 of SEQ ID NO: 1) |
| 8 | MsrA/B fragment lacking the signal sequence (corresponding to aa 30-522 of SEQ ID NO: 1) |
| 9 | Full length MsrA/B from N. gonorrhoeae strain PID322 |
| 10 | Full length MsrA/B from N. gonorrhoeae strain WHO_K |
| 11 | Full length MsrA/B from N. gonorrhoeae strain MS-11 |
| 12 | Full length MsrA/B from N. meningitidis strain MC58 |

TABLE 3-continued

BRIEF DESCRIPTION OF THE SEQUENCES

| SEQ ID NO: | Description |
|---|---|
| 13 | Nucleic acid sequence encoding MsrA/B from N. gonorrhoeae strain 1291 (SEQ ID NO: 1) |
| 14 | Nucleic acid sequence encoding MsrA/B fragment lacking the signal sequence (SEQ ID NO: 7) |
| 15 | Recombinant MsrA/B comprising His tag and linker |
| 16 | Nucleic acid sequence encoding recombinant MsrA/B (SEQ ID NO: 15) |
| 17 | Primer 1291msrFor |
| 18 | Primer 1291msrRev |
| 19 | Neisseria uptake sequence |
| 20 | Primer msrexp_NdeIF |
| 21 | Primer msrexp_XhoIR |
| 22 | Primer 15bmsrAFor_NdeI |
| 23 | Primer 15bmsrARev_XhoI |
| 24 | Primer 15bmsrBFor_NdeI |
| 25 | Primer 15bmsrBRev_XhoI |
| 26 | Nucleic acid sequence encoding MsrA with His tag and linker |
| 27 | Recombinant MsrA with His tag and linker |
| 28 | Recombinant MsrA without His tag |
| 29 | Nucleic acid sequence encoding MsrB with His tag and linker |
| 30 | Recombinant MsrB with His tag and linker |
| 31 | Recombinant MsrB without His tag |
| 32 | 100bp upstream of porB |
| 33 | Primer PmeI_For |
| 34 | Primer PmeI_Rev |
| 35 | Primer pCTS32_porBPromoter_AflIIFor |
| 36 | Primer pCTS32_porBPromoter_PmeIR |
| 37 | Primer pCTS32_Msr_AflIIFor |
| 38 | Primer pCTS32_Msr_SmaIRev |
| 39 | Recombinant MsrA/B without His tag |

Each embodiment described herein is to be applied mutatis mutandis to each and every embodiment unless specifically stated otherwise.

2. MsrA/B

The gonococcal methionine sulfoxide reductase MsrA/B plays an important role in protecting N. gonorrhoeae from oxidative damage (Skaar et al, 2002, Proc Natl Acad Sci USA 99(15), 10108-10113), by catalyzing the reduction of methionine sulfoxide residues Met(O) back to methionine (Met) (Lowther et al., 2002, Nat Struct Biol 9(5), 348-352; and Brot et al., 2006, J Biol Chem 281(43), 32668-32675). Mechanisms for coping with oxidative stress are crucial for the survival of human pathogens such as N. gonorrhoeae, which are routinely exposed to oxidative killing by the host and that are frequently isolated within polymorphonuclear leukocytes (PMNs). Methionine residues in proteins can easily be oxidized by the presence of reactive oxygen species, affecting protein structure and function. The enzyme methionine sulfoxide reductase (Msr) can repair oxidized methionine by catalyzing the reduction of methionine sulfoxide residues (Met(O)) back to methionine (Met) in the cytoplasmic methionine pool and in damaged proteins (Weissbach et al. 2005, Biochim Biophys Acta 1703(2), 203-212). Pathogenic bacteria like Escherichia coli, Helicobacter pylori, Pseudomonas aeruginosa, Streptococcus pneumoniae and Staphylococcus aureus all contain Msr enzymes that protect against oxidative damage.

The majority of bacterial methionine sulfoxide reductase systems consist of separate cytoplasmic MsrA and MsrB proteins, which are specific for the Met-S(O) and Met-R(O) epimers, respectively. During the catalytic process, firstly a sulfenic intermediate is produced with concurrent release of the repaired Met and, secondly, a recycling step occurs where oxidized MsrA and/or MsrB are reduced to their active form via a thioredoxin/thioredoxin reductase system (Ezraty et al., 2005, Biochim Biophys Acta 1703(2), 221-

229). However, in *N. gonorrhoeae* and the closely related *N. meningitidis*, the MsrA, MsrB and thioredoxin enzymatic functions are present in a single protein, MsrA/B, that is located in the outer membrane (Skaar et al., 2002, Proc Natl Acad Sci USA 99(15), 10108-10113).

MsrA/B of *N. gonorrhoeae* and *N. meningitidis* was presumed to be facing the periplasmic space. However, as determined by the present inventors for the first time, the gonococcal and meningococcal MsrA/B protein is surface exposed. This is in stark contrast to other examples of Gram-negative methionine sulfoxide reductases, where the enzyme exists in the cytoplasm and utilises the cytoplasmic thiol pool regenerated by thioredoxin reductase.

MsrA/B from *N. gonorrhoeae* and *N. meningitidis* is highly conserved and typically 522 amino acids in length, with a putative signal peptide at the N terminus. An exemplary full length MsrA/B polypeptide from *N. gonorrhoeae* strain 1291 is set forth in SEQ ID NO:1. The precise amino acid residues that constitute each region or domain in the polypeptide have not been settled on, but it has been reported that the putative signal sequence or peptide is contained within or spans amino acid residues corresponding to residues 1-31 of SEQ ID NO:1; the thioredoxin domain is contained within or comprises amino acid residues corresponding to residues 17-174 of SEQ ID NO: 1; the MsrA domain is contained within or comprises amino acid residues corresponding to residues 181-362 or 199-354 of SEQ ID NO: 1; and the MsrB domain is contained within or comprises amino acid residues corresponding to residues 375-522 or 383-506 of SEQ ID NO:1 (Lowther et al., 2002, Nat Struct Biol 9(5), 348-352; and Uniprot Acc. No. P14930). By alignment with the *N. meningitidis* MsrA/B polypeptide, catalytic residues include those at positions corresponding to positions 64, 67, 68, 71, 238, 250, 285, 290, 348, 349, 440, 442, 477, 480, 493, 495 and 497.

Full length MsrA/B polypeptide from *N. gonorrhoeae* strain 1291 (putative signal sequence in bold):

(SEQ ID NO: 1)
MKHRTFFSLCAKFGCLLALGACSPKIVDAGTATVPHTLSTLKTADNRPAS

VYLKKDKPTLIKFWASWCPLCLSELGQAEKWAQDAKFSSANLITVASPGF

LHEKKDGEFQKWYAGLNYPKLPVVTDNGGTIAQNLNISVYPSWALIGKDG

DVQRIVKGSINEAQALALIRNPNADLGSLKHSFYKPDTQKKDSAIMNTRT

IYLAGGCFWGLEAYFQRIDGVVDAVSGYANGNTENPSYEDVSYRHTGHAE

TVKVTYDADKLSLDDILQYYFRVVDPTSLNKQGNDTGTQYRSGVYYTDPA

EKAVIAAALKREQQKYQLPLVVENEPLKNFYDAEEYHQDYLIKNPNGYCH

IDIRKADEPLPGKTKAAPQGKGFDAATYKKPSDAELKRTLTEEQYQVTQN

SATEYAFSHEYDHLFKPGIYVDVVSGEPLFSSADKYDSGCGWPSFTRPID

AKSVTEHDDFSFNMRRTEVRSRAADSHLGHVFPDGPRDKGGLRYCINGAS

LKFIPLEQMDAAGYGALKGKVK

3. MsrA/B Polypeptides and Polynucleotides

As demonstrated herein for the first time, MsrA/B is highly conserved and surface exposed in *N. gonorrhoeae* and the related *N. meningitidis*. Moreover, antibodies specific for MsrA/B mediate bactericidal and opsonophagocytic killing of *N. gonorrhoeae* and are able to inhibit binding of MsrA/B to its substrate, methionine sulfoxide (Met(O)). Accordingly, provided are MsrA/B polypeptides and polynucleotides, which can be used as described herein in compositions, methods and uses for eliciting an immune response to *N. gonorrhoeae* and *N. meningitidis* in a subject, for immunizing a subject against *N. gonorrhoeae* and *N. meningitidis*, and for the prevention and treatment of an infection and/or disease caused by *N. gonorrhoeae* and *N. meningitidis*.

3.1 Exemplary MsrA/B Polypeptides

MsrA/B polypeptides of the present disclosure include full length MsrA/B polypeptides (e.g., the full length MsrA/B from *N. gonorrhoeae* 1291 set forth in SEQ ID NO:1 or full length MsrA/B polypeptide from other *N. gonorrhoeae* or *N. meningitidis* strains, such as the MsrA/B from *N. gonorrhoeae* PID322 (SEQ ID NO:9), *N. gonorrhoeae* WHO_K (SEQ ID NO:10), *N. gonorrhoeae* MS-11 (SEQ ID NO:11) and *N. meningitidis* MC58 (SEQ ID NO:12), antigenic fragments thereof, and variants thereof, such as variants comprising at least or about 90%, 91%, 92%, 93%, 94%, 95%, 96%, 97%, 98%, or 99% sequence identity thereto.

Antigenic fragments include, for example, those having at least or about 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 340, 350, 360, 370, 380, 390, 400, 410, 420, 430, 440, 450, 460, 470, 480, 490, 500 or 510 amino acid residues of a full length MsrA/B polypeptide. As would be appreciated, antigenic fragments must include at least one B cell and/or T cell epitope. Typically, the antigenic fragments include at least one B cell epitope, and preferably 2 or more B cell epitopes, such as 2, 3, 4, 5 or more B cell epitopes, optionally with at least one T helper cell epitope, such as 1, 2, 3, 4 or more T helper cell epitopes.

The antigenic fragments may be truncated at the N-terminus and/or C-terminus, such as by at least or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more amino acids at the N-terminus and/or C-terminus compared to a full length MsrA/B polypeptide. Alternatively, or in addition, the antigenic fragments may lack one or more amino acid residues that are not at the N- or C-terminus compared to a full length MsrA/B polypeptide (i.e., are "internal"), such as at least or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more amino acid residues. These may be contiguous or non-contiguous.

Exemplary MsrA/B polypeptides that are antigenic fragments of a full length MsrA/B polypeptide include those lacking all or a portion of the signal sequence, i.e., truncated at the N-terminus. In particular examples, the MsrA/B polypeptide lacks at least or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids from the N-terminus of a full length MsrA/B. Thus, for example, MsrA/B polypeptides of the present disclosure may comprise amino acids corresponding to amino acids 5-522, 6-522, 7-522, 8-522, 9-522, 10-522, 11-522, 12-522, 13-522, 14-522, 15-522, 16-522, 17-522, 18-522, 19-522, 20-522, 21-522, 22-522, 23-522, 24-522, 25-522, 26-522, 27-522, 28-522, 29-522, 30-522, 31-522, 32-522, 33-522, 34-522, 35-522, 36-522, 37-522, 38-522, 39-522, 40-522, 41-522, 42-522, 43-522, 44-522, 45-522, 46-522, 47-522, 48-522, 49-522, or 50-522 of SEQ ID NO: 1. One such exemplary MsrA/B polypeptide is a polypeptide comprising amino acids corresponding to amino acids 32-522 of SEQ ID NO:1, i.e., lacking all of the putative signal peptide spanning amino acids 1-31. An example of such a polypeptide is that set forth in SEQ ID NO:7. In another non-limiting example, the MsrA/B polypeptide lacks a portion of the signal sequence and comprises amino acids corresponding to amino acids 30-522 of SEQ ID NO: 1. An example of such a polypeptide is that set forth in SEQ ID NO:8.

N-terminally truncated MsrA/B polypeptide (corresponding to aa 32-522 of SEQ ID NO:1):

(SEQ ID NO: 7)
ATVPHTLSTLKTADNRPASVYLKKDKPTLIKFWASWCPLCLSELGQAEKW

AQDAKFSSANLITVASPGFLHEKKDGEFQKWYAGLNYPKLPVVTDNGGTI

AQNLNISVYPSWALIGKDGDVQRIVKGSINEAQALALIRNPNADLGSLKH

SFYKPDTQKKDSAIMNTRTIYLAGGCFWGLEAYFQRIDGVVDAVSGYANG

NTENPSYEDVSYRHTGHAETVKVTYDADKLSLDDILQYYFRVVDPTSLNK

QGNDTGTQYRSGVYYTDPAEKAVIAAALKREQQKYQLPLVVENEPLKNFY

DAEEYHQDYLIKNPNGYCHIDIRKADEPLPGKTKAAPQGKGFDAATYKKP

SDAELKRTLTEEQYQVTQNSATEYAFSHEYDHLFKPGIYVDVVSGEPLFS

SADKYDSGCGWPSFTRPIDAKSVTEHDDFSFNMRRTEVRSRAADSHLGHV

FPDGPRDKGGLRYCINGASLKFIPLEQMDAAGYGALKGKVK

N-terminally truncated MsrA/B polypeptide (corresponding to aa 30-522 of SEQ ID NO:1):

(SEQ ID NO: 8)
GTATVPHTLSTLKTADNRPASVYLKKDKPTLIKFWASWCPLCLSELGQAE

KWAQDAKFSSANLITVASPGFLHEKKDGEFQKWYAGLNYPKLPVVTDNGG

TIAQNLNISVYPSWALIGKDGDVQRIVKGSINEAQALALIRNPNADLGSL

KHSFYKPDTQKKDSAIMNTRTIYLAGGCFWGLEAYFQRIDGVVDAVSGYA

NGNTENPSYEDVSYRHTGHAETVKVTYDADKLSLDDILQYYFRVVDPTSL

NKQGNDTGTQYRSGVYYTDPAEKAVIAAALKREQQKYQLPLVVENEPLKN

FYDAEEYHQDYLIKNPNGYCHIDIRKADEPLPGKTKAAPQGKGFDAATYK

KPSDAELKRTLTEEQYQVTQNSATEYAFSHEYDHLFKPGIYVDVVSGEPL

FSSADKYDSGCGWPSFTRPIDAKSVTEHDDFSFNMRRTEVRSRAADSHLG

HVFPDGPRDKGGLRYCINGASLKFIPLEQMDAAGYGALKGKVK

Exemplary MsrA/B polypeptides that are antigenic fragments of a full length MsrA/B polypeptide also include those comprising all or a portion of the MsrA domain, e.g., all or a portion of amino acid residues corresponding to residues 181-362 or 199-354 of SEQ ID NO: 1. Non-limiting examples of such polypeptides are those that comprise amino acids corresponding to about amino acid 225-325, 224-326, 223-327, 222-328, 221-329, 220-330, 219-331, 218-332, 217-333, 216-334, 215-335, 214-336, 213-337, 212-338, 211-339, 210-340, 209-341, 208-342, 207-343, 206-344, 205-345, 204-346, 203-347, 202-348, 201-349, 200-350, 199-351, 198-352, 197-353, 196-354, 195-355, 194-356, 193-357, 192-358, 191-359, 190-360, 189-361, 188-362, 187-363, 186-364, 185-365, 184-366, 183-367, 182-368, 181-369, 180-370, 179-381, 178-372, 177-373, 176-374 or 175-375 of SEQ ID NO: 1. Examples of such polypeptides are those comprising the sequence set forth in SEQ ID NO:2, which corresponds to amino acids 181-362 of SEQ ID NO:1; and SEQ ID NO:3, which corresponds to amino acids 199-354 of SEQ ID NO:1. MsrA/B polypeptide comprising the MsrA domain (corresponding to aa 181-362 of SEQ ID NO: 1):

(SEQ ID NO: 2)
HSFYKPDTQKKDSAIMNTRTIYLAGGCFWGLEAYFQRIDGVVDAVSGYAN

GNTENPSYEDVSYRHTGHAETVKVTYDADKLSLDDILQYYFRVVDPTSLN

KQGNDTGTQYRSGVYYTDPAEKAVIAAALKREQQKYQLPLVVENEPLKNF

YDAEEYHQDYLIKNPNGYCHIDIRKADEPLPG

MsrA/B polypeptide comprising the MsrA domain (corresponding to aa 199-354 of SEQ ID NO: 1):

(SEQ ID NO: 3)
RTIYLAGGCFWGLEAYFQRIDGVVDAVSGYANGNTENPSYEDVSYRHTGH

AETVKVTYDADKLSLDDILQYYFRVVDPTSLNKQGNDTGTQYRSGVYYTD

PAEKAVIAAALKREQQKYQLPLVVENEPLKNFYDAEEYHQDYLIKNPNGY

CHIDIR

Exemplary MsrA/B polypeptides that are antigenic fragments of a full length MsrA/B polypeptide further include those comprising all or a portion of the MsrB domain, e.g., all or a portion of amino acid residues corresponding to residues 375-522 or 383-506 of SEQ ID NO: 1. Non-limiting examples of such polypeptides are those that comprise amino acids corresponding to about amino acid 395-495, 394-496, 393-497, 392-498, 391-499, 390-500, 389-501, 388-502, 387-503, 386-504, 385-505, 384-506, 383-507, 382-508, 381-509, 380-510, 379-511, 378-512, 377-513, 376-514, 375-515, 374-516, 373-517, 372-518, 371-519, 370-520, 369-521, or 368-522 of SEQ ID NO: 1. Examples of such polypeptides are those comprising the sequence set forth in SEQ ID NO:4, which corresponds to amino acids 375-522 of SEQ ID NO: 1; and SEQ ID NO:5, which corresponds to amino acids 383-506 of SEQ ID NO:1.

MsrA/B polypeptide comprising the MsrB domain (corresponding to aa 375-522 of SEQ ID NO: 1):

(SEQ ID NO: 4)
AATYKKPSDAELKRTLTEEQYQVTQNSATEYAFSHEYDHLFKPGIYVDVV

SGEPLFSSADKYDSGCGWPSFTRPIDAKSVTEHDDFSFNMRRTEVRSRAA

DSHLGHVFPDGPRDKGGLRYCINGASLKFIPLEQMDAAGYGALKGKVK

MsrA/B polypeptide comprising the MsrB domain (corresponding to aa 383-506 of SEQ ID NO: 1):

(SEQ ID NO: 5)
DAELKRTLTEEQYQVTQNSATEYAFSHEYDHLFKPGIYVDVVSGEPLFSS

ADKYDSGCGWPSFTRPIDAKSVTEHDDFSFNMRRTEVRSRAADSHLGHVF

PDGPRDKGGLRYCINGASLKFIPL

Additional exemplary polypeptides include those that comprise all or a portion of the thioredoxin domain, e.g., all or a portion of amino acid residues corresponding to residues 17-174 of SEQ ID NO: 1. Non-limiting examples of such polypeptides are those that comprise amino acids corresponding to about amino acid 40-150, 39-151, 38-152, 37-153, 36-154, 35-155, 34-156, 33-157, 32-158, 31-159, 30-160, 29-161, 28-162, 27-163, 26-164, 25-165, 24-166, 23-167, 22-168, 21-169, 20-170, 19-171, 18-172, 17-173, 16-174, 15-175, 14-176, 13-177, 12-178, 11-179 or 10-180 of SEQ ID NO: 1. An example of such a polypeptide is that comprising the sequence set forth in SEQ ID NO:6, which corresponds to amino acids 17-174 of SEQ ID NO: 1.

MsrA/B polypeptide comprising the thioredoxin domain (corresponding to aa 17-174 of SEQ ID NO:1):

(SEQ ID NO: 6)
LALGACSPKIVDAGTATVPHTLSTLKTADNRPASVYLKKDKPTLIKFWAS

WCPLCLSELGQAEKWAQDAKFSSANLITVASPGFLHEKKDGEFQKWYAGL

NYPKLPVVTDNGGTIAQNLNISVYPSWALIGKDGDVQRIVKGSINEAQAL

ALIRNPNA 3.2 Additional Moeities

The MsrA/B polypeptides described above and herein can also comprise or be linked to one or more moieties, such as one or more other antigenic polypeptides, one or more T helper cell epitopes, one or more other immunostimulatory molecules, one or more targeting agents, one or more polymers, one or more proteins, one or more multimerisation domains, one or more detectable labels, one or more affinity tags or any combination thereof. The polypeptides can be linked to the one or more other moieties by any method known in the art, including any chemical or recombinant method resulting in the formation of covalent and/or non-covalent bonds between the polypeptide and the one or more other moieties.

To assist in eliciting a humoral immune response to the MsrA/B polypeptide when the polypeptide is administered to a subject, the polypeptides can be linked to one or more T helper cell epitopes or a polypeptide comprising one or more T helper cell epitopes. This may be particularly desired where the MsrA/B polypeptide is an antigenic fragment of a full length MsrA/B polypeptide and comprises one or more B cell epitopes and no, or relatively weak, T helper cell epitopes. Any T helper cell epitope can be linked to the MsrA/B polypeptides provided the T helper epitope is recognized by T helper cells in the subject to which the polypeptide will be administered. Promiscuous or universal T helper cell epitopes that are recognized in the context of different MHC backgrounds (i.e., in a genetically diverse population) are well known in the art and can be linked to the peptides provided herein (see e.g., Diethelm-Okita et al., 2000, J. Inf. Dis. 181:1001-1009; Greenstein et al., 1992, J Immunol 148(12):3970-3977). Known T helper cell epitopes can be identified using publicly accessible databases such as the Immune Epitope Database and Analysis Resource (iedb.org) and new T helper cell epitopes can be identified using methods well known in the art (see e.g., Pira et al., 2010, J Biomed Biotechnol). It is well within the ability of a skilled person to identify and select an appropriate T helper cell epitope for the desired purpose.

T helper cell epitopes that can be linked to the polypeptides provided herein include, but are not limited to, those derived from microorganism proteins, such as viral proteins and bacterial proteins, as well as artificial or synthetic T helper cell epitopes (see e.g., U.S. Pat. No. 6,713,301). In some examples, the T helper cell epitopes are from potent immunogens such as tetanus toxin, diptheria toxin, poliovirus, pertussis toxin, the measles virus F protein, HIV gp120 and HIV Gag proteins, and the hepatitis B virus surface antigen (HbsAg). In some instances, the T helper cell epitopes are provided within the context of a larger protein. Thus, the MsrA/B polypeptides of the present disclosure can be linked to a protein or polypeptide comprising a T helper cell epitope. Exemplary proteins are carrier proteins, such as tetanus toxoid, diphtheria toxoid, cross-reacting material 197 (CRM-197).

The MsrA/B polypeptides of the present invention may also be linked or fused to an affinity tag to, for example, facilitate purification. Exemplary affinity tags include, but are not limited to, chitin binding protein (CBP), maltose binding protein (MBP), glutathione-S-transferase (GST), FLAG, His, c-myc and HA tags. For example, MsrA/B polypeptides may comprise a His tag, such as a 6-His tag, which can facilitate purification of the polypeptide using a metal ion affinity column or resin. In further examples, amino acids constituting a cleavage site, such as a thrombin, enterokinase or Factor Xa cleavage site, are present between the affinity tag and the MsrA/B polypeptide so as to enable cleavage of the affinity tag from the MsrA/B polypeptide following purification. Detectable molecules, including, but not limited to, fluorescent or chemiluminescent molecules, or biotin or streptavidin, also can be linked to the polypeptides.

The one or more other moieties linked to the provided MsrA/B polypeptides can be linked by any method known in the art, including chemical methods and recombinant methods. Proteins (e.g., carrier proteins such as tetanus toxoid, diphtheria toxoid or CRM-197) can be conjugated to the polypeptides using standard chemical coupling techniques such as m-maleimidobenzoyl-N-hydroxysuccinimide ester (MBS), glutaraldehyde, 1-Ethyl-3-(3-dimethylaminopropyl)carbodiimide (EDC), or bisdiazobenzidine (BDB) coupling. In other examples, the polypeptides are linked to other peptides (such as those including a T cell epitope) or proteins by peptide synthesis methods or recombinant methods. For example, a polypeptide can be linked to a T cell epitope by sequentially synthesizing the polypeptide then the T cell epitope as a single polypeptide using standard methods (e.g., Fmoc solid phase synthesis). In other examples, nucleic acid encoding the MsrA/B polypeptide can be operatively linked to nucleic acid encoding the T cell epitope (or any other protein) and the entire nucleic acid molecule expressed, such as using a bacterial expression system, to produce a single polypeptide containing the polypeptide and the T cell epitope. Accordingly, linkage can be by covalent and/or non-covalent bonds, depending on the method of linkage employed.

In some examples, a peptide linker or spacer is used to link or fuse the MsrA/B polypeptides and the one or more other moieties. Peptide linkers typically are from about 1 amino acid in length to about 10 amino acids in length, although can be longer. Non-limiting examples of peptide linkers that can be used herein include linkers having the sequence K, KK, KKK, GPGPG, G, GG, GGG, GGGG, GGA, GA, GD, GSGGGG, GSGGGGS, GSHMK, GS, RS, RR, KKK, KKAA, VE, and AAY. Thus, exemplary MsrA/B polypeptides also include those set forth in SEQ ID NOs:15, 27, 28, 30, 31 and 39, which include a His tag, thrombin cleavage site and/or linker.

3.3 Exemplary MsrA/B Polynucleotides

Also provided are polynucleotides encoding the MsrA/B polypeptides described above and herein, such as any one of the polypeptides set forth in SEQ ID NOs:1-12, 15, 27 and 29, antigenic fragments thereof or polypeptides having at least or about 90%, 91%, 92%, 93%, 94%, 95%, 96%, 97%, 98% or 99% sequence identity thereto. Non-limiting examples of such polynucleotides include those set forth in SEQ ID NOs:13, 14, 16, 26 and 28 and polynucleotides having at least or about 85%, 86%, 87%, 88%, 89%, 90%, 91%, 92%, 93%, 94%, 95%, 96%, 97%, 98% or 99% sequence identity thereto. For example, the nucleic acid sequence of an exemplary polynucleotide encoding the full length MsrA/B polypeptide of SEQ ID NO:1 is set forth in SEQ ID NO: 13, and the nucleic acid sequence of an exemplary polynucleotide encoding an N-terminally truncated MsrA/B polypeptide lacking the putative signal sequence (i.e., comprising nucleotides 94-1569 of SEQ ID NO: 13) is set forth in SEQ ID NO: 14. MsrA/B polynucleotides of the present disclosure also include those that hybridize to a polynucleotide set forth in SEQ ID NO:13 or 14 under high stringency conditions.

An exemplary polynucleotide encoding the full length MsrA/B polypeptide of SEQ ID NO:1, where the nucleotides in bold (nucleotides 1-93) encode the putative signal sequence:

(SEQ ID NO: 13)
ATGAAACACCGTACTTTCTTTTCCCTTTGCGCCAAGTTCGGCTGCCTGCT

TGCGCTGGGCGCTTGTTCGCCCAAAATCGTCGATGCCGGGACCGCGACCG

TGCCGCACACTTTATCCACGTTAAAAACCGCGGACAACCGCCCCGCCAGT

GTTTATTTGAAAAAGACAAACCGACGCTGATTAAATTTTGGGCGAGCTG

GTGTCCTTTATGTTTGTCCGAATTGGGACAGGCCGAGAAATGGGCGCAAG

ATGCAAAATTCAGCTCCGCCAACCTGATTACCGTCGCCTCCCCCGGCTTT

TTGCACGAGAAAAAGACGGCGAGTTTCAAAAATGGTATGCCGGTTTGAA

CTACCCCAAGCTGCCCGTCGTTACCGACAACGGCGGCACGATCGCCCAAA

ACCTGAATATCAGCGTTTATCCTTCTTGGGCGTTAATCGGTAAAGACGGC

GACGTGCAGCGCATCGTCAAAGGCAGCATCAACGAAGCGCAGGCATTGGC

GTTAATCCGCAACCCGAATGCCGATTTGGGCAGTTTGAAACATTCGTTCT

ACAAACCCGACACTCAGAAAAAGGATTCAGCAATCATGAACACGCGCACC

ATCTACCTCGCCGGCGGCTGCTTCTGGGGCTTGGAAGCCTATTTCCAACG

CATCGACGGCGTGGTTGACGCGGTATCCGGCTACGCCAACGGCAACACGG

AAAACCCGAGCTACGAAGACGTGTCCTACCGCCATACGGGCCATGCCGAG

ACCGTCAAAGTGACCTACGATGCCGACAAACTCAGCCTGGACGACATCCT

GCAATATTATTTCCGCGTCGTTGATCCGACCAGCCTCAACAAACAGGGTA

ACGACACCGGCACGCAATACCGCAGCGGCGTGTACTACACCGACCCCGCC

GAAAAAGCCGTCATCGCCGCCGCCCTCAAACGCGAGCAGCAAAAATACCA

ACTGCCCCTCGTTGTTGAAAACGAACCGCTGAAAAACTTCTACGACGCCG

AGGAATACCATCAGGACTACCTGATTAAAAACCCCAACGGCTACTGCCAC

ATCGACATCCGCAAAGCCGACGAACCGCTGCCGGGCAAAACCAAAGCCGC

ACCGCAAGGCAAAGGCTTCGACGCGGCAACGTATAAAAAACCGAGTGACG

CCGAACTCAAACGCACCCTGACCGAAGAGCAATACCAAGTGACCCAAAAC

AGCGCGACCGAATACGCCTTCAGCCACGAATACGACCATTTGTTCAAACC

CGGCATTTATGTGGACGTTGTCAGCGGCGAACCCCTGTTCAGCTCCGCCG

ACAAATATGATTCCGGCTGCGGCTGGCCGAGCTTCACGCGCCCGATTGAT

GCAAAATCCGTTACCGAACACGATGATTTCAGCTTCAATATGCGCCGCAC

CGAAGTCAGAAGCCGCGCCGCCGATTCGCACTTGGGACACGTCTTCCCCG

ACGGCCCCGCGACAAAGGCGGACTGCGCTACTGCATCAACGGCGCGAGC

TTGAAATTCATCCCGCTGGAACAAATGGACGCGGCAGGCTACGGCGCGTT

GAAGGGCAAAGTGAAATAA.

An exemplary polynucleotide encoding N-terminally truncated MsrA/B polypeptide of SEQ ID NO:7, i.e., lacking the putative signal sequence:

(SEQ ID NO: 14)
GCGACCGTGCCGCACACTTTATCCACGTTAAAAACCGCGGACAACCGC

CCCGCCAGTGTTTATTTGAAAAAGACAAACCGACGCTGATTAAATTTTG

GGCGAGCTGGTGTCCTTTATGTTTGTCCGAATTGGGACAGGCCGAGAAAT

GGGCGCAAGATGCAAAATTCAGCTCCGCCAACCTGATTACCGTCGCCTCC

CCCGGCTTTTTGCACGAGAAAAAGACGGCGAGTTTCAAAAATGGTATGC

CGGTTTGAACTACCCCAAGCTGCCCGTCGTTACCGACAACGGCGGCACGA

TCGCCCAAAACCTGAATATCAGCGTTTATCCTTCTTGGGCGTTAATCGGT

AAAGACGGCGACGTGCAGCGCATCGTCAAAGGCAGCATCAACGAAGCGCA

GGCATTGGCGTTAATCCGCAACCCGAATGCCGATTTGGGCAGTTTGAAAC

ATTCGTTCTACAAACCCGACACTCAGAAAAAGGATTCAGCAATCATGAAC

ACGCGCACCATCTACCTCGCCGGCGGCTGCTTCTGGGGCTTGGAAGCCTA

TTTCCAACGCATCGACGGCGTGGTTGACGCGGTATCCGGCTACGCCAACG

GCAACACGGAAAACCCGAGCTACGAAGACGTGTCCTACCGCCATACGGGC

CATGCCGAGACCGTCAAAGTGACCTACGATGCCGACAAACTCAGCCTGGA

CGACATCCTGCAATATTATTTCCGCGTCGTTGATCCGACCAGCCTCAACA

AACAGGGTAACGACACCGGCACGCAATACCGCAGCGGCGTGTACTACACC

GACCCCGCCGAAAAAGCCGTCATCGCCGCCGCCCTCAAACGCGAGCAGCA

AAAATACCAACTGCCCCTCGTTGTTGAAAACGAACCGCTGAAAAACTTCT

ACGACGCCGAGGAATACCATCAGGACTACCTGATTAAAAACCCCAACGGC

TACTGCCACATCGACATCCGCAAAGCCGACGAACCGCTGCCGGGCAAAAC

CAAAGCCGCACCGCAAGGCAAAGGCTTCGACGCGGCAACGTATAAAAAAC

CGAGTGACGCCGAACTCAAACGCACCCTGACCGAAGAGCAATACCAAGTG

ACCCAAAACAGCGCGACCGAATACGCCTTCAGCCACGAATACGACCATTT

GTTCAAACCCGGCATTTATGTGGACGTTGTCAGCGGCGAACCCCTGTTCA

GCTCCGCCGACAAATATGATTCCGGCTGCGGCTGGCCGAGCTTCACGCGC

CCGATTGATGCAAAATCCGTTACCGAACACGATGATTTCAGCTTCAATAT

GCGCCGCACCGAAGTCAGAAGCCGCGCCGCCGATTCGCACTTGGGACACG

TCTTCCCCGACGGCCCCGCGACAAAGGCGGACTGCGCTACTGCATCAAC

GGCGCGAGCTTGAAATTCATCCCGCTGGAACAAATGGACGCGGCAGGCTA

CGGCGCGTTGAAGGGCAAAGTGAAATAA 3.4 Methods for Producing and Assessing the MsrA/B Polypeptides The MsrA/B polypeptides provided herein can be produced using any method known in the art, including peptide synthesis techniques and recombinant techniques in which a nucleic acid molecule encoding the MsrA/B polypeptide is used to express the MsrA/B polypeptide. Thus, provided herein are recombinant and/or synthetic MsrA/B polypeptides and MsrA/B polynucleotide.

In particular examples, the polypeptides are produced using recombinant methods well known in the art. Nucleic acid encoding the polypeptides can be obtained by any suitable method, including, but not limited to, PCR of *N. gonorrhoeae* or *N. meningitidis* genomic DNA or chemical synthesis of an polynucleotide that encodes a polypeptide of the present disclosure. It is well within the skill of a skilled artisan to design and/or produce a nucleic acid molecule that encodes a polypeptide described herein.

The polynucleotide encoding the MsrA/B polypeptide can be expressed in a variety of different expression systems, such as, for example, those used with bacteria, yeast, baculoviruses, mammalian cells and plants, each of which are well known in the art. A polynucleotide encoding the MsrA/B polypeptide can be cloned into an expression vector suitable for the expression system of choice, operably linked to regulatory sequences that facilitate expression of the heterologous nucleic acid molecule. Many expression vectors are available and known to those of skill in the art for the expression of polypeptides. The choice of expression vector is influenced by the choice of host expression system. Such selection is well within the level of skill of the skilled artisan. In general, expression vectors can include transcriptional promoters and optionally enhancers to which the MsrA/B polynucleotide is operably linked, translational signals, and transcriptional and translational termination signals. Expression vectors that are used for stable transformation typically have a selectable marker which allows selection and maintenance of the transformed cells.

In some examples, bacterial expression techniques, which are well known in the art, are used to express the MsrA/B polypeptides. Bacterial expression vectors for use in various systems, and in particular those that utilise *E. coli*, are well known and available commercially, and it is understood that those skilled in the art can readily select and use the appropriate bacterial expression system for production of MsrA/B polypeptides. Briefly, bacterial promoters useful for expression of heterologous sequences such as a MsrA/B polynucleotide include inducible and constitutive promoters. Promoters associated with bacterial genes encoding metabolic pathway enzymes may be particularly useful. Examples include promoter sequences derived from sugar metabolizing enzymes, such as galactose, lactose (lac), and maltose. Additional examples include promoter sequences derived from biosynthetic enzymes such as tryptophan (trp). Synthetic promoters are also widely utilized in bacterial expression systems, and include, for example, the hybrid trp-lac promoter comprised of both trp promoter and lac operon sequences regulated by the lac repressor. Bacterial promoters can also include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system. In addition to a functioning promoter sequence, an efficient ribosome binding site (e.g., the Shine-Dalgarno (SD) sequence in *E. coli*) is also useful for the expression of exogenous genes in prokaryotes. The bacterial expression vector used for expression of the MsrA/B polypeptide generally also contains transcription termination sequences.

The MsrA/B molecule may be expressed and retained intracellularly, or may be secreted from the cell. For example, the MsrA/B polynucleotide can be expressed as a chimeric or fusion protein containing an exogenous signal peptide that provides for secretion of the protein in bacteria. The signal sequence usually encodes a signal peptide comprised of hydrophobic amino acids which direct the secretion of the protein from the cell. The protein is either secreted into the growth media (Gram-positive bacteria) or into the periplasmic space, located between the inner and outer membrane of the cell (Gram-negative bacteria). Preferably there are processing sites, which can be cleaved either in vivo or in vitro encoded between the signal peptide fragment and the foreign gene. Suitable signal sequences include those derived from genes for secreted bacterial proteins, such as the *E. coli* outer membrane protein gene (ompA), the *E. coli* alkaline phosphatase signal sequence (phoA) and the alpha-amylase gene from various *Bacillus* strains.

Yeasts such as *Saccharomyces cerevisiae, Schizosaccharomyces pombe, Yarrowia lipolytica, Kluyveromyces lactis*, and *Pichia pastoris* are also useful expression hosts for MsrA/B polypeptides. Yeast can be transformed with episomal replicating vectors or by stable chromosomal integration by homologous recombination. Typically, inducible promoters, such as include GAL1, GAL7, and GAL5, are used to regulate gene expression. Yeast expression vectors often include a selectable marker such as LEU2, TRPI, HIS3, and URA3 for selection and maintenance of the transformed DNA.

In another example, insects and insect cells are used for expressing MsrA/B polypeptides. For example, the baculovirus expression system can be used in conjunction with the insect cells. Baculoviruses have a restrictive host range which improves the safety and reduces regulatory concerns of eukaryotic expression. Typically, expression vectors use a promoter such as the polyhedrin promoter of baculovirus for high level expression. Commonly used baculovirus systems include baculoviruses such as *Autographa californica* nuclear polyhedrosis virus (AcNPV), and the *Bombyx mori* nuclear polyhedrosis virus (BmNPV). Exemplary insect cell lines include such the Sf9 cell line derived from *Spodoptera frugiperda*, the A7S cell line derived from *Pseudaletia unipuncta* and the DpN1 cell line derived from *Danaus plexippus*. For high level expression, the nucleotide sequence of the molecule to be expressed is fused immediately downstream of the polyhedrin initiation codon of the virus.

Mammalian expression systems also can be used to express the MsrA/B polypeptides described herein. Expression constructs can be transferred to mammalian cells by viral infection, such as using adenovirus, or by direct DNA transfer such as using liposomes, calcium phosphate, DEAE-dextran and by physical means such as electroporation and microinjection. Expression vectors for mammalian cells typically include an mRNA cap site, a TATA box, a translational initiation sequence (Kozak consensus sequence) and polyadenylation elements. Such vectors often include transcriptional promoter-enhancers for high level expression, for example the SV40 promoter-enhancer, the human cytomegalovirus (CMV) promoter, and the long terminal repeat of Rous sarcoma virus (RSV). Exemplary cell lines available for mammalian expression include, but are not limited to, mouse, rat, human, monkey, and chicken and hamster cells, such as BHK, 293-F, CHO, Balb/3T3, HeLa, MT2, mouse NSO (non-secreting) and other myeloma cell lines, hybridoma and heterohybridoma cell lines, lymphocytes, fibroblasts, Sp2/0, COS, NIH3T3, HEK293, 293S, 293T, 2B8, and HKB cells.

The antigenic properties of the MsrA/B polypeptides can be assessed using a variety of methods known to those skilled in the art. For example, the ability of the polypeptides to induce an antibody response can be assessed by administering (such as by intravenous, intraperitoneal or intramuscular injection) the polypeptide to a subject (e.g., a non-human subject) one or more times. Typically, the polypeptides are formulated with or co-administered with a suitable adjuvant, such as one described below. The immune response, and in particular the antibody response, elicited can be assessed at various time points after immunization by sampling the blood of the subject and subjecting the sera to analysis using an appropriate assay, such as an ELISA or Western blot. For example, a multiwell plate can be coated with an MsrA/B polypeptide or *N. gonorrhoeae* or *N. meningitidis* preparations. Such methods can be used to determine the magnitude and specificity of an antibody response elicited by administration of the provided polypeptides. The ability of the polypeptides to be recognized by antibodies, including polyclonal or monoclonal antibodies directed to *N. gonorrhoeae* or *N. meningitidis*, can be assessed by standard methods, including, but not limited to, ELISA, Western blot, dot blot, surface plasmon resonance and rapid flow tests (e.g., lateral or vertical flow test).

4. Nucleic Acid Delivery Vehicles

The polynucleotides encoding a MsrA/B polypeptide described herein may be provided in a nucleic acid delivery vehicle. Such vehicles can be delivered to a subject for expression of the MsrA/B polypeptide in the subject. These vehicles can include viral or non-viral vectors, as well as mechanical and particulate delivery platforms.

Viral vectors for vaccine applications are well known in the art (for review, see, e.g., Ura et al., 2014 Vaccines 2(3):624-641; Choi and Chang, 2013, Clin Exp Vaccine Res. 2(2): 97-105; Humphreys and Sebastian, 2018, Immunology 153:1-9). Non-limiting examples of viral vectors that can be employed for delivery of polynucleotides encoding a MsrA/B polypeptide to a subject include retrovirus (including lentivirus), adenovirus, adeno-associated virus (AAV), herpes virus (e.g., Cytomegalovirus (CMV)), alphavirus, astrovirus, coronavirus, orthomyxovirus, papovavirus, paramyxovirus (e.g., Sendai virus), parvovirus, picornavirus, poxvirus (e.g., vaccinia virus), and togavirus vectors.

Retroviral vectors are well known in the art and the MsrA/B polynucleotide can be introduced into any retroviral vector, including B, C and D type retroviruses, xenotropic retroviruses (for example, NZB-X1, NZB-X2 and NZB9-1), polytropic retroviruses e.g., MCF and MCF-MLV, spumaviruses and lentiviruses. Exemplary retroviruses for the construction of retroviral vectors containing a MsrA/B polynucleotide include Avian Leukosis Virus, Bovine Leukemia Virus, Murine Leukemia Virus, Mink-Cell Focus-Inducing Virus, Murine Sarcoma Virus, Reticuloendotheliosis Virus and Rous Sarcoma Virus. In some examples, portions of the retroviral vector are derived from different retroviruses. For example, retrovector long terminal repeats (LTRs) may be derived from a Murine Sarcoma Virus, a tRNA binding site from a Rous Sarcoma Virus, a packaging signal from a Murine Leukemia Virus, and an origin of second strand synthesis from an Avian Leukosis Virus.

Recombinant retroviral vectors may be used to generate transduction competent retroviral vector particles by introducing them into appropriate packaging cell lines. Retrovirus vectors can be constructed for site-specific integration into host cell DNA by incorporation of a chimeric integrase enzyme into the retroviral particle (see WO1996/37626). Preferably, the recombinant viral vector is a replication defective recombinant virus. Packaging cell lines suitable for use with the above-described retrovirus vectors are well known in the art, are readily prepared (see e.g., WO1995/30763 and WO1992/05266), and can be used to create producer cell lines (also termed vector cell lines or "VCLs") for the production of recombinant vector particles. Preferably, the packaging cell lines are made from human parent cells (e.g., HT1080 cells) or mink parent cell lines, which eliminates inactivation in human serum.

Human adenoviral (e.g., Ad5) and adenovirus associated virus (AAV) vectors are also known and employable for the delivery of MsrA/B polynucleotides for expression in a subject. Adenovirus vectors are typically replication-incompetent and have been widely used in vaccination strategies for a number of infectious diseases, such as malaria, rabies, HIV, tuberculosis and influenza (for review, see e.g., Zhang and Zhou, 2016, Hum Vaccin Immunother. 2016 August; 12(8): 2064-2074). AAV vectors, and in particular AAV-2 based vectors with varying capsid polypeptides, have been widely utilised in gene therapy and vaccine applications in humans and can be applied in the present disclosure (for review, see e.g., Naso et al, 2017, BioDrugs 31(4):317-334). AAV vectors typically comprise two AAV inverted terminal repeats (ITRs) flanking the gene of interest (in this case, the MsrA/B polynucleotide), which is operably linked to a promoter. This recombinant AAV genome is packaged in an AAV capsid, which can have limited (specific) or broad cell tropism.

Suitable viral vectors also include, for example, herpes vectors (e.g., CMV vectors), alpha virus vectors (e.g., Venezuelan equine encephalitis virus (VEE), Sindbis virus (SIN), Semliki forest virus (SFV), and VEE-SIN chimeras; for review, see e.g., Lundstrom 2012, J Vacc Vaccination, 3:139), rhinovirus (see e.g., Tomusange et a. 2015, Virus Res 203:72-6), vaccinia virus (see e.g., Gilbert 2013, Vaccine 31(39): 4241-4246), measles virus (see e.g., Cantarella et al., 2009. Vaccine 27:3385-3390), and Chikungunya virus (see e.g., Brandler et al., 2013, Vaccine 31:3718-3725).

Delivery of the MsrA/B polynucleotides into cells is not limited to the above mentioned viral vectors. Other delivery methods and media may be employed such as, for example, micro- and nanoparticles, including poly(lactide-co-glycolide) (PLGA)-based particles, poly(ethylene imine) (PEI)-based particles, chitosan-based nanoparticles, cationic lipids and inorganic particles (for review, see e.g. Farris et al., 2016, 241:919-929). Liposomes, virus-like particles and the like (discussed in greater detail below) can also be employed. Further non-viral delivery suitable for use includes mechanical delivery systems, such as gene gun systems.

5. Therapeutic Antigen-Binding Molecules

The present disclosure also provides antigen-binding molecule, including polyclonal and monoclonal (mAb) antibodies and antigen binding fragments thereof, that specifically bind to a *N. gonorrhoeae* or *N. meningitidis* MsrA/B polypeptide. Typically, the antigen-binding molecules exhibit bactericidal and/or opsonophagocytic activity in vitro and/or in vivo. In some instances, the antigen-binding molecules may also inhibit the activity of a MsrA/B polypeptide, such as binding to Met(O), which can inhibit the ability of the MsrA/B polypeptide to catalyze the reduction of Met(O) to methionine. The antibodies of the present disclosure can therefore be used therapeutically, so as to treat *N. gonorrhoeae* or *N. meningitidis* infection in a subject.

Thus, provided herein are isolated antibodies, such as isolated polyclonal and monoclonal antibodies (including antigen-binding fragments thereof, such as single-chain Fv (scFv), Fab, Fab', F(ab')2, Fv, dsFv, diabody, Fd, and Fd' fragments) that specifically bind to the MsrA/B polypeptides described herein, including the MsrA/B polypeptides set forth in SEQ ID NOs:1-12, 15, 27 and 29, antigenic fragments thereof and variants thereof comprising at least or about 90%, 91%, 92%, 93%, 94%, 95% m 96%, 97%, 98%, 99% sequence identity. The antibodies may be of any isotype, including IgG (including IgG1, IgG2a, IgG2b, IgG3 and IgG4), IgM, IgA, IgD and IgE, and can be polyclonal or monoclonal, non-human (e.g., mouse, rat, rabbit, guinea pig) or human, or chimeric or humanized. Preferably, the antibodies are human or humanized. In particular embodiments, the antibodies are IgG antibodies, including for example, IgG1, IgG2a and/or IgG3 antibodies. In further embodiments, the antibodies are IgA antibodies.

Techniques for preparing antigen-binding molecules against polypeptides are well known in the art. For example, polyclonal antibodies directed against a MsrA/B polypeptide described herein can be generated by administering the polypeptide to a subject (such as a non-human subject, e.g., a mouse, rat or rabbit), optionally in combination with an adjuvant. The polyclonal antibodies produced following administration can then be isolated from the serum of the subject. In other examples, monoclonal antibodies specific for a MsrA/B polypeptide can be obtained by injecting a subject (e.g., a non-human subject) with the polypeptide (optionally in conjunction with an adjuvant), then removing the spleen to obtain B lymphocytes. Alternatively, B lymphocytes can be isolated from peripheral blood lymphocytes (PBL). The B lymphocytes from immunized subjects can then be fused with myeloma cells to produce hybridomas, which are cloned. Positive clones that produce antibodies to the MsrA/B polypeptide are selected using standard techniques (e.g., ELISpot), culturing the clones that produce antibodies to the antigen, and isolating the antibodies from the hybridoma cultures.

Monoclonal antibodies can be isolated and purified from hybridoma cultures by a variety of well-established techniques including, but not limited to, affinity chromatography with Protein-A SEPHAROSE®, size-exclusion chromatography, and ion-exchange chromatography. After the initial raising of antibodies to the MsrA/B polypeptide, the antibodies can be sequenced and subsequently prepared by recombinant techniques. Humanized forms of the antibodies can be prepared using standard and well-known techniques.

Monoclonal antibodies and antigen-binding fragments thereof can also be produced from an antibody library. For example, total RNA can be extracted from peripheral blood B lymphocytes of a subject, such as a healthy subject or a subject that has been or is infected with *N. gonorrhoeae* or *N. meningitidis*, and a cDNA library constructed by amplifying μ, γ and κ chain antibody repertoires. The cDNA library can then be used to make a display library, such as a phage display library in which antigen-binding fragments of antibodies, such as single chain Fv (scFv) fragments, are expressed on the surfaces of bacteriophages as fusion proteins with the bacteriophage coat protein. Typically, the libraries are combinatorial. Antibodies or fragments thereof that recognize and bind to a MsrA/B polypeptide can then be screened and selected. Alternatively, previously prepared antibody libraries, including previously prepared immune libraries, naïve libraries, semi-synthetic libraries, and synthetic libraries, can be used to screen for and select antibodies that specifically bind to MsrA/B polypeptides. Methods for the production and screening of antibody libraries so as to identify antibodies with the desired specificity are well known in the art and any such method can be used in conjunction with the present disclosure (for review, see e.g., Lerner, 2016, Nat Rev Immunol, 16(8):498-508; Lim and Chan, 2016, Curr Pharm Des., 22(43):6480-6489; and Chen and Sidhu, 2014, Methods Mol Biol. 1131:113-31).

The antigen-binding molecules of the present disclosure can be linked to one or more moieties, such as to facilitate detection, such as in pre-clinical studies. For example, antigen-binding molecules may be linked to a detectable label such a fluorescent, chemiluminescent, enzyme, biotin/streptavidin or metabolic labels. Non-limiting examples of labels that can be linked to the antibodies and antigen-binding fragments include biotin, streptavidin, alkaline phosphatase (AP), horseradish peroxidase (HRP), fluorescein isothiocyanate (FITC), rhodamine (tetramethyl rhodamine isothiocyanate, TRITC), green fluorescent protein (GFP), allophycocyanin, phycocyanin, phycoerythrin and phycoerythrocyanin. Antigen-binding molecules may be linked to one or more moieties using any method known in the art. For example, linkage may be through chemical conjugation using one of a variety of well known techniques, including but not limited to the use of NHS esters, heterobifunctional reagents, carbodiimides or sodium periodate.

The binding properties of the antigen-binding molecules of the present disclosure, such as the ability to bind to the MsrA/B polypeptides provided herein, or *N. gonorrhoeae* or *N. meningitidis*, can be characterized by established methodologies, for example, ELISA and Western blot. Any method known to one of skill in the art can be used to measure the binding properties of an antigen-binding molecule. In some examples, the binding properties are assessed by performing a saturation binding assay, for example, a saturation ELISA, whereby binding of the antibody to the polypeptide is assessed with increasing amounts of antibody. In such experiments, it is possible to assess whether the binding is dose-dependent and/or saturable. In addition, the binding affinity can be extrapolated from the 50% binding signal. Typically, apparent binding affinity is measured in terms of its association constant ($K_a$) or dissociation constant ($K_d$) and determined using Scatchard analysis. For example, binding affinity to a target polypeptide can be assessed in a competition binding assay in where increasing concentrations of unlabeled protein is added, such as by radioimmunoassay (RIA) or ELISA. The ability of the antibodies to bind to *N. gonorrhoeae* or *N. meningitidis* also can be assessed using methods well known in the art. For example, the binding of antigen-binding molecules to *N. gonorrhoeae* or *N. meningitidis* can be assessed by ELISA or Western blot, or visualized by microscopy using direct or indirect fluorescence.

The bactericidal and/or opsonophagocytic activity of the antigen-binding molecules can also be assessed using well known assays, in vitro and/or in vivo. For example, the antigen-binding molecules can be assessed in vitro such as described in the Examples below. Briefly, the survival of *N. gonorrhoeae* or *N. meningitidis* in the presence of an antigen-binding molecule of the present disclosure and a source of human complement (e.g., human serum) is assessed. In another example, the survival of *N. gonorrhoeae* or *N. meningitidis* in the presence of an antigen-binding molecule of the present disclosure, polymorphonuclear neutrophils (PMNs) and a source of human complement (e.g., human serum) is assessed. Non-human animal models of *N. gonorrhoeae* or *N. meningitidis* infection can also be used to assess the activity of the antigen-binding molecules. Such mouse models include, for example, the estradiol-treated female mouse model and various transgenic models (e.g., CAECAM1) for *N. gonorrhoeae* (see e.g., Jerse, 1999, Infect. Immun. 67, 5699-570; Packlam et al., 2010, Infect Immun., 78(1):433-440; and Rice et al., 2017, Annu Rev Microbiol., 71:665-686), and the iron dextran model and various transgenic models (e.g., CD46, CAECAM1, and human transferrin) for *N. meningitidis* (see e.g., Yi et al., 2003, Infect Immun. 71(4): 1849-1855; Weyand, 2017, Pathogens Dis, 75(3), ftx031).

6. Compositions

Also provided are compositions comprising a MsrA/B polypeptide, MsrA/B polynucleotide (optionally within a nucleic acid delivery vehicle), and/or an anti-MsrA/B antigen-binding molecule described above and herein. In some embodiments, the compositions are pharmaceutical compositions.

Where the compositions comprise a MsrA/B polypeptide or MsrA/B polynucleotide, the compositions are typically immunogenic compositions (or vaccine compositions). Such immunogenic compositions, when administered to a subject, elicit an immune response to the MsrA/B polypeptide present in the composition or encoded by the polynucleotide in the composition. Most typically, the immune response is a protective immune response that prevents, inhibits or ameliorates infection and/or disease by *N. gonorrhoeae* or *N. meningitidis*. Compositions for use in the present disclosure preferably have a vaccine efficacy against *N. gonorrhoeae* or *N. meningitidis* of at least 10% e.g., >20%, >30%, >40%, >50%, >60%, >70%, >80%, >85%, >90%, or more. A protective immune response typically comprises anti-MsrA/B antibodies, which may be bactericidal, opsonophagocytic and/or functional blocking (i.e. inhibit the function of a MsrA/B polypeptide, such as inhibit the ability of a MsrA/B polypeptide to catalyze the reduction of Met(O) to methionine). The antibodies may comprise IgG1, IgG2a, IgG2b, IgG3, IgM and/or IgA antibodies. In particular embodiments, the immunogenic compositions of the present disclosure elicit anti-MsrA/B IgG1, IgG2a, IgG3 and/or IgA antibodies.

Typically, the immunogenic (or vaccine) compositions of the present disclosure comprise an adjuvant, and suitable adjuvants will be known to persons skilled in the art. Non-limiting examples of suitable adjuvants include aluminium salts (e.g., aluminium hydroxide, aluminium phosphate and potassium aluminium sulfate (also referred to as Alum)), water-in-oil or oil-in-water emulsions (e.g., Montanide®, MF59® (an oil-in-water emulsion containing squalene) and AS03 (an oil-in-water emulsion containing squalene), 3-<9-desacyl-4'-monophosphoryl lipid A (MPL) and adjuvants containing MPL (e.g., AS01, AS02, AS04 and AS15; see for review Garcon and Di Pasquale, 2017, Hum Vaccin Immunother. 2017, 13(1): 19-33), toll like receptor (TLR) agonists (including TLR1, TLR2, TLR3, TLR4, TLR5, TLR7, TLR8, TLR9 and TLR10 agonists, including CpG; see for review Steinhagen et al., 2011, 29(17): 3341-3355), saponin-based adjuvants, liposomes, virosomes, virus-like particles (VLPs), outer membrane vesicles (OMVs), cytokines, chemokines and growth factors, such as, such as interleukins (e.g., IL-1, IL-2, IL-4, IL-5, IL-6, IL-7, IL-12, etc.), interferons (e.g., INF-γ), macrophage colony stimulating factor (M-CSF), and tumor necrosis factor (TNF). Combinations of two or more adjuvants within the same composition are also contemplated herein.

Saponin-based adjuvants include saponins or saponin derivatives from, for example, *Quillaja saponaria, Panax ginseng Panax notoginseng, Panax quinquefolium, Platycodon grandiflorum, Polygala senega, Polygala tenuifolia, Quillaja brasiliensis, Astragalus membranaceus* and *Achyranthes bidentata*. Exemplary saponin-based adjuvants include iscoms, iscom matrix, ISCOMATRIX™ adjuvant, Matrix M™ adjuvant, Matrix C™ adjuvant, Matrix Q™ adjuvant, AbISCO®-100 adjuvant, AbISCO®-300 adjuvant, ISCOPREP™, an ISCOPREP™ derivative, adjuvant containing ISCOPREP™ or an ISCOPREP™ derivative, QS-21, a QS-21 derivative, and an adjuvant containing QS-21 or a QS21 derivative.

TLR agonists include both natural agonists, such as PAMP (pathogen-associated molecular patterns) or DAMP (damage-associated molecular pattern) ligands, and synthetic agonists. TLR agonists for the purposes of the present disclosure are known in the art and include TLR1/2 agonists (e.g., triacylated lipopeptides, Pam3Cys), TLR2 agonists (e.g., peptidoglycan from Gram positive bacteria, bacterial lipoprotein, lipoteichoic acid, lipopolysaccharide (LPS), GPI-anchor proteins, Neisserial porins, phospholipomannan, CFA, MALP2, Pam2Cys, FSL-1 and Hib-OMPC), TLR3 agonists (e.g., single-stranded and double-stranded viral RNA, poly I:C, poly A:U), TLR4 agonists (e.g., GLA-SE (Glucopyranosyl Lipid A (GLA) formulated in a stable oil-in-water nano-emulsion (SE); Coler et al., PLoS ONE 6, e16333), LPS, RSV F-protein; mannan, glycoinositolphospholipids, RSV and MMTV envelope proteins, Hsp60, Hsp70, fibronectin domain A, surfactant protein A, hyaluronan, HMGB-1, AGP, MPLA, RC-529, MDF2β and CFA), TLR2/6 agonists (e.g., phenol-soluble modulin, diacylated lipopeptides, LTA, zymosan, MALP-2, Pam2Cys and FSL-1), TLR7 agonists (e.g., viral single-stranded RNA, human RNA, guanosine analogs, and imidazoquinolines (e.g., Imiquimod, Aldara®, R848, Resiquimod®) and loxoribine), TLR8 agonists (e.g., viral single-stranded RNA, human RNA, imidazoquinolines, loxoribine and ssPolyU), TLR9 agonists (dsDNA viruses, hemozoin, unmethylated CpG DNA, human DNA/chromatin, LL37-DNA and CpG-oligonucleotides) and TLR10 agonists. In particular examples, the nanoparticulate carriers include Pam2Cys.

Particulate carriers, which can be internalised by an antigen presenting cell (APC), and in particular a dendritic cell (DC), are also contemplated as adjuvants for the present disclosure. Exemplary particulate carriers include, but are not limited to, liposomes (including neutral, anionic or cationic liposomes; and ethosomes), virosomes, VLP, OMVs, archaeosomes, plasma membrane vesicles (PMVs), niosomes, lipid core peptides (LCPs), immunostimulating complexes (ISCOMs), polymer based nanoparticles (e.g., biodegradeable nanoparticles such as Poly(D,L-lactic-co-glycolic acid)(PLGA) nanoparticles, polypropylene sulphide nanoparticles and polyhydroxylated-nanoparticles). A wide variety of particulate carriers are well known in the art and have been extensively studied and described elsewhere (for review, see e.g., Joshi et al., 2012, J Cont Release 161:25-37; Altin 2012, Liposomes and other nanoparticles as cancer vaccines and immunotherapeutics. Chapter 8 In: *Innovations in Vaccinology: from design, through to delivery and testing*. S. Baschieri Ed, Springer; Gregory et al., 2013, Front Cell Infect Microbiol. 3: 13; and Zhao et al., 2014, 32(3):327-337). Thus, the present disclosure also provides a particulate carrier, such as any described above, comprising a MsrA/B polypeptide or MsrA/B polynucleotide.

In a particular example, the particulate carrier (i.e., the adjuvant) is an OMV. OMVs occur naturally in Gram negative bacteria, and are non-replicating spherical nanoparticles consisting of proteins, lipids (mostly LPS) and periplasmic contents. As a result of their particulate nature and composition, including a variety of pathogen-associated molecular patterns (PAMPs), OMVs are highly immunostimulatory, capable of engaging with both the innate and adaptive immune system. OMVs have themselves been used as standalone vaccines (e.g., *N. meningitidis* OMVs as a vaccine for *N. meningitidis*, with or without additional *N. meningitidis* antigens). However, they are also are potent adjuvants for use with exogenous antigens (for review, see e.g., Gerritzen et al. 2017, Biotech Adv. 35:565-574; and Tan et al., 2018, Front Microbiol, 9:783). Methods for preparing OMVs with the antigen of choice are well known in the art and described elsewhere (for review, see e.g., Gerritzen et al., supra). Briefly, antigens, such as a MsrA/B polypeptide of the present disclosure, can be formulated with the OMVs for surface exposure, non-surface exposure, attached to the OMV or not attached (i.e., simple admixture). The antigen and OMV can be produced by the Gram negative bacteria simultaneously such that the OMV is produced with the antigen loaded on to the surface or lumen of the OMV. Alternatively, the antigen can be attached to the OMV after production of the OMV, such as by covalent attachment using an affinity tag on the antigen that binds to a fusion protein in the OMV (see e.g., Alves et al., 2015, ACS Appl. Mater. Interfaces, 7(44): 24963-24972). Still further, the antigen can be loaded to the OMV lumen after the OMV had been produced, or can be simply admixed with the OMV after the OMV had been produced. Exemplary OMVs for use as an adjuvant with a MsrA/B polypeptide of the present disclosure include OMVs produced from any Gram negative bacteria, including, but not limited to, *N. meningitidis, N. gonorrhoeae, E. coli* and *P. aeruginosa*.

In other examples, the adjuvant comprises liposomes, which are lipid based bilayer vesicles. Versatility in particle size and in the physical parameters of the lipids has resulted in liposomes been widely used as carriers of drugs, peptides, proteins, and nucleic acid molecules for pharmaceutical, cosmetic, and biochemical purposes. Liposomes are composed primarily of vesicle-forming lipids, which may be natural, semi-synthetic or fully synthetic, and neutral, negatively or positively charged. Exemplary vesicle-forming lipids include the sphingolipids, ether lipids, sterols, phospholipids, particularly the phosphoglycerides, and the glycolipids, such as the cerebrosides and gangliosides. Lipids suitable for use in liposomes are known to persons of skill in the art and are cited in a variety of sources, such as 1998 McCutcheon's Detergents and Emulsifiers, 1998 McCutcheon's Functional Materials, both published by McCutcheon Publishing Co., New Jersey, and the Avanti Polar Lipids, Inc. Catalog. In particular examples, the liposomes comprise any one or more of 1,2-dioleoyl-sn-glycero-3-phosphocholine (DOPC), 1,2-dioleoyl-sn-glycero-3-phospho-(1'-rac-glycerol) (sodium salt) (DOPG), 1,2-dioleoyl-sn-glycero-3-phospho-L-serine (sodium salt) (DOPS), 1,2-dioleoyl-sn-glycero-3-phosphoethanolamine (DOPE), 1,2-dioleoyl-3-trimethylammonium-propane (chloride salt) (DOTAP), 1,2-dioleoyl-3-dimethylammonium-propane (DODAP), 1,2-distearoyl-sn-glycero-3-phosphoethanolamine-N-[methoxy (polyethylene glycol)-750](ammonium salt) (DSPE-PEG750), 1-palmitoyl-2-oleoyl-sn-glycero-3-phosphocholine (POPC), or 2-(4,4-Difluoro-5-Methyl-4-Bora-3a,4a-Diaza-s-Indacene-3-Dodecanoyl)-1-Hexadecanoyl-sn-Glycero-3-Phosphocholine (Bodipy). Methods of producing liposomes are well known to those skilled in the art, and have been described extensively elsewhere (for review, see e.g., Wagner and Vorauer-Uhl (2011) J Drug Delivery, Article ID 591325; Yu et al., (2009) Methods Enzymol. 465: 129-141, and Laouini et al., (2012) J Colloid Sci Biotech 1:147-168), 2012.). These methods include, for example, thin-film hydration, detergent dialysis, reverse-phase evaporation, ethanol injection, freeze-drying of a monophase solution, microfluidic hydrodynamic focusing, and supercritical fluid methods.

In particular embodiments, the adjuvant is one that promotes a humoral response to the MsrA/B polypeptide or promotes a predominantly humoral response to the MsrA/B polypeptide.

The immunogenic compositions of the present disclosure may also comprise one or more additional antigens (e.g., 1, 2, 3, 4, 5 or more additional antigens), including one or more *N. gonorrhoeae* antigens, one or more *N. meningitidis* antigens, or one or more antigens from another pathogen, including a bacterial, fungal or viral pathogen. The antigen may be, for example, a protein, polynucleotide encoding a protein, polysaccharide or oligosaccharide. In particular examples, the immunogenic compositions comprise one or more *N. gonorrhoeae* antigens, such as, for example, PilC, PilQ, Opa, AniA, TdfJ, PorB, Lst, TbpB, TbpA, OmpA, OpcA, MetQ, MtrE and/or the 2C7 epitope or epitope mimetic (for review, see e.g., Jerse, 2014, Vaccine 32(14): 1579-1587; Vincent and Jerse, 2018, Vaccine 18 April). The immunogenic compositions may also, or alternatively, comprise one or more *N. meningitidis* antigens, including but not limited to capsular polysaccharides or oligosaccharides from one or more of meningococcal serogroups A, C, W135 and/or Y, NadA, fHbp, NHBA, GNA1030, GNA2091, HmbR, NspA, NhA, App, Omp85, TbpA, TbpB, and/or Cu,Zn-superoxide dismutase.

The present disclosure also contemplates pharmaceutical compositions that comprise a MsrA/B polypeptide, a MsrA/B polynucleotide and/or an anti-MsrA/B antigen-binding molecule, formulated with one or more pharmaceutically-acceptable carriers. The pharmaceutical compositions may optionally comprise one or more other antigens or antibodies, compounds, drugs, ingredients and/or materials. Regardless of the route of administration selected, the pharmaceutical composition of the present disclosure is formulated into pharmaceutically-acceptable dosage forms by conventional methods known to those of skill in the art (see, e.g., Remington, The Science and Practice of Pharmacy (21$^{st}$ Edition, Lippincott Williams and Wilkins, Philadelphia, Pa.)).

A pharmaceutical composition of the present disclosure may be administered to a subject in any desired and effective manner. For example, the pharmaceutic compositions may be formulated for oral ingestion, or as an ointment or drop for local administration to the eyes, or for parenteral or other administration in any appropriate manner such as intraperitoneal, subcutaneous, topical, intradermal, inhalation, intrapulmonary, rectal, vaginal, sublingual, intramuscular, intravenous, intraatrial, intrathecal, or intralymphatic. Further, a pharmaceutical composition of the present disclosure may be administered in conjunction with one or more ancillary treatment, as described in detail below. A pharmaceutical composition of the present disclosure may be encapsulated or otherwise protected against gastric or other secretions, if desired.

The pharmaceutical compositions of the disclosure may comprise one or more active ingredients in admixture with one or more pharmaceutically-acceptable carriers and, optionally, one or more other compounds, drugs, ingredients and/or materials. Regardless of the route of administration selected, the bispecific antibodies of the present disclosure are formulated into pharmaceutically-acceptable dosage forms by conventional methods known to those of skill in the art (see, e.g., Remington, The Science and Practice of Pharmacy (21$^{st}$ Edition, Lippincott Williams and Wilkins, Philadelphia, Pa.)).

Pharmaceutically acceptable carriers are well known in the art (see, e.g., Remington, The Science and Practice of Pharmacy (21$^{st}$ Edition, Lippincott Williams and Wilkins, Philadelphia, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and triglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable carrier used in a pharmaceutical composition of the disclosure must be "acceptable" in the sense of being compatible with the other ingredients of the formulation and not injurious to the subject. Carriers suitable for a selected dosage form and intended route of administration are well known in the art, and acceptable carriers for a chosen dosage form and method of administration can be determined using ordinary skill in the art.

The pharmaceutical compositions of the disclosure optionally contain additional ingredients and/or materials commonly used in pharmaceutical compositions, including therapeutic antigen-binding molecule preparations. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monostearate, gelatin, and waxes; (18) opacifying agents; (19) adjuvants; (20) emulsifying and suspending agents; (21), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (22) propellants, such as chlorofluorohydrocarbons and volatile unsubstituted hydrocarbons, such as butane and propane; (23) antioxidants; (24) agents which render the formulation isotonic with the blood of the intended recipient, such as sugars and sodium chloride; (25) thickening agents; (26) coating materials, such as lecithin; and (27) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Pharmaceutical compositions of the present disclosure suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s) with one or more pharmaceutically-acceptable carriers and, optionally, one or more fillers, extenders, binders, humectants, disintegrating agents, solution retarding agents, absorption accelerators, wetting agents, absorbents, lubricants, and/or coloring agents. Solid compositions of a similar type may be employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Pharmaceutical compositions of the present disclosure for rectal or vaginal administration may be presented as a suppository, which may be prepared by mixing one or more active ingredient(s) with one or more suitable non-irritating carriers which are solid at room temperature, but liquid at body temperature and, therefore, will melt in the rectum or vaginal cavity and release the active compound. Pharmaceutical compositions of the present disclosure which are suitable for vaginal administration also include pessaries, tampons, creams, gels, pastes, foams or spray formulations containing such pharmaceutically-acceptable carriers as are known in the art to be appropriate.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

Pharmaceutical compositions of the present disclosure suitable for parenteral administrations comprise one or more agent(s)/compound(s)/antigen-binding molecules in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

Dosage forms for the topical or transdermal administration include powders, sprays, ointments, pastes, creams, lotions, gels, solutions, patches (including a microneedle patch), drops and inhalants. The active agent (e.g., therapeutic combination) may be mixed under sterile conditions with a suitable pharmaceutically-acceptable carrier. The ointments, pastes, creams and gels may contain excipients. Powders and sprays may contain excipients and propellants.

In some cases, in order to prolong the effect of a pharmaceutical composition, it is desirable to slow its absorption from subcutaneous or intramuscular injection. This may be accomplished by the inclusion of a liquid suspension of crystalline or amorphous material having poor water solubility.

The rate of absorption of individual components of the composition then depends upon their rates of dissolution which, in turn, may depend upon crystal size and crystalline form. Alternatively, delayed absorption of the active components of a parenterally-administered composition may be accomplished by dissolving or suspending the components in an oil vehicle. Injectable depot forms may be made by forming microencapsulated matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the active component in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

7. Prophylactic and Therapeutic Methods

Also disclosed herein is a method for eliciting an immune response (such as a protective immune response) to *N. gonorrhoeae* and/or *N. meningitidis* in a subject, comprising administering to the subject a composition comprising a MsrA/B polypeptide, and/or MsrA/B polynucleotide to the subject. Thus, the present disclosure extends to the use of the MsrA/B polypeptides and/or MsrA/B polynucleotides described herein for the preparation of a vaccine (or immunogenic) composition for eliciting an immune response (such as a protective immune response) to *N. gonorrhoeae* and/or *N. meningitidis*, for immunizing a subject against *N. gonorrhoeae* and/or *N. meningitidis* and/or preventing or treating an infection and/or disease caused by *N. gonorrhoeae* and/or *N. meningitidis* in a subject. Additionally, the disclosure encompasses methods for treating an infection and/or disease *N. gonorrhoeae* and/or *N. meningitidis* infection in a subject by administering a composition comprising an anti-MsrA/B antigen-binding molecule described herein.

As would be appreciated, given the high level of sequence identity between MsrA/B polypeptides from *N. gonorrhoeae* and *N. meningitidis*, cross-reactive and cross-protective immune responses can be elicited when administering the compositions of the present disclosure to a subject. Thus, for example, administration of a composition comprising MsrA/B polypeptides or polynucleotides from *N. gonorrhoeae* can result in the generation of an immune response against both *N. gonorrhoeae* and *N. meningitidis*, and protection against both *N. gonorrhoeae* and *N. meningitidis* infection. Similarly, administration of a composition comprising MsrA/B polypeptides or polynucleotides from *N. meningitidis* can result in the generation of an immune response against both *N. meningitidis* and *N. gonorrhoeae*, and protection against both *N. meningitidis* and *N. gonorrhoeae* infection and/or disease. Such cross-reactivity and cross-protection has been previously suggested with *Neisseria* vaccines (see e.g., Petousis-Harris et al., 2017, Lancet 390:1603-1610).

In some embodiments, the subject to whom the composition is administered is seronegative for *N. gonorrhoeae* and/or *N. meningitidis*. In other instances, the subject is seropositive for *N. gonorrhoeae* and/or *N. meningitidis*. Moreover, the subject may not be infected with *N. gonorrhoeae* and/or *N. meningitidis*. In such instances, the composition, such as a vaccine composition, is administered as a prophylactic composition. In other embodiments, the subject is infected with *N. gonorrhoeae* and/or *N. meningitidis*. In such instances, the composition, such as a vaccine composition or composition comprising an anti-MsrA/B antibody, is administered as a therapeutic composition.

The compositions, as described herein, are typically administered in an "effective amount"; that is, an amount effective to elicit an immune response or a therapeutic or prophylactic effect. Persons skilled in the art would be able, by routine experimentation, to determine an effective, non-toxic amount to include in a pharmaceutical composition or to be administered for the desired outcome. In general, the compositions, as disclosed herein, can be administered in a manner compatible with the route of administration and physical characteristics of the recipient (including health status) and in such a way that it elicits the desired effect(s) (i.e., therapeutically effective, immunogenic and/or protective). For example, the appropriate dosage of a composition may depend on a variety of factors including, but not limited to, a subject's physical characteristics (e.g., age, weight, sex), whether the composition is being used as single agent or as part of adjunct therapy, the progression (i.e., pathological state) of any underlying infection, and other factors that may be recognized by persons skilled in the art. Other illustrative examples of general considerations that may be considered when determining, for example, an appropriate dosage of the compositions are discussed by Gennaro (2000, "Remington: The Science and Practice of Pharmacy", 20th edition, Lippincott, Williams, & Wilkins; and Gilman et al., (Eds), (1990), "Goodman And Gilman's: The Pharmacological Bases of Therapeutics", Pergamon Press).

It is expected that the effective amount will fall in a relatively broad range that can be determined through methods known to persons skilled in the art, having regard to some of the considerations outlined above. Effective amounts can be determined empirically by those skilled in the art.

It will be apparent to persons skilled in the art that the optimal quantity and spacing of individual dosages, if required to induce the desired immune response, can be determined, for example, by the form, route and site of administration, and the nature of the particular subject to be treated, as is described elsewhere herein. Optimum conditions can be determined using conventional techniques known to persons skilled in the art.

Compositions of the invention will generally be administered directly to a subject, such as via parenteral injection (e.g., subcutaneously, intraperitoneally, intravenously, intramuscularly, or intradermally), or by any other suitable route, including intranasally, orally or via a pessary. In some embodiments, the compositions are administered intramuscularly. Injection may be via a needle (e.g., a hypodermic needle), but needle-free injection may also be used. A typical intramuscular dosage volume for human subjects is 0.5 ml, but may be 0.1, 0.2, 0.3, 0.4, 0.5, 0.6, 0.7, 0.8, 0.9, 1.0 mL or more, and may be dependent on the weight and/or age of the subject, amongst other factors. The volume of the dose may further vary depending on the concentration of the MsrA/B polypeptide, MsrA/B polynucleotide or anti-MsrA/B antibody in the composition.

In some instances, it may be desirable to have several or multiple administrations of the compositions. For example, the compositions may be administered 1, 2, 3, 4, 5, 6, 7, 8, 9, 10, or more times. The administrations may be from about one day intervals to about 52 week intervals, and in certain embodiments from about one to about four, one to eight, one to twelve, one to 24 or one to 36 week intervals. Periodic re-administration may be required to achieve a desirable result, such as a desired level of immune response.

The following examples are given merely to illustrate the present invention and not in any way to limit its scope.

EXAMPLES

Example 1

Materials and Methods

Bacterial Strains and Growth Conditions

*N. gonorrhoeae* 1291, 20 clinical isolates from mucosal and disseminated gonococcal infections (Power et al. 2007 Infect Immun 75(6), 3202-3204) and *N. meningitidis* MC58¢3 (Virji et al. 1995 Mol Microbiol 18(4), 741-754) strains were grown on GC agar (Oxoid) with 1% IsoVitaleX (Becton Dickinson) or Brain Heart Infusion (BHI, Oxoid) 1% agar with 10% Levinthal's Base medium at 37° C. with 5% $CO_2$, respectively, with either kanamycin (kan) (100 µg/ml) or tetracycline (5 µg/ml) as required.

Sequence Bioinformatics Analysis

Distribution of MsrA/B in gonococcal genomes, available at GenBank and at the *Meningitidis* Research Foundation (MRF) Meningococcus Genome Library (PubMLST) database, was investigated using BLAST search with MsrA/B from *N. gonorrhoeae* 1291 (GenBank Accession: protein—EEH61172.1; nucleotide—DS999919.1, Locus tag NGAG_00088).

Generation of Mutant Strains

The 1569 bp msr gene from *N. gonorrhoeae* 1291 was amplified with primers 1291msrFor (5'-GCCGTCTGAAATGAAACACCGTACTTTC1T1TCCC-3'; SEQ ID NO:17) and 1291msrRev (5'-TTCAGACGGCT-TATTTCACTTTGCCCTTCAACGCG-3'; SEQ ID NO:18) containing the Neisseria uptake sequence 5'-GCCGTCT-GAA-3' (SEQ ID NO: 19) and the resulting PCR product was cloned into pGem®-T Easy (Promega) to generate pGemTmsr. The Mutation Generation System™ (MGS) kit (Thermo Fisher) was used according to the manufacturer's instructions to insert a transposon containing a kanR3 gene into pGemTmsr. The location and orientation of the kanR3 in msr was determined by sequencing. The msr::kan construct was linearized and transformed into *N. gonorrhoeae* 1291 and *N. meningitidis* MC58¢3 by homologous recombination to generate 1291msr::kan and MC58¢3msr::kan mutant strains. To generate complemented strains the intact msr gene was introduced into either the 1291 msr::kan mutant using the complementation plasmid pCTS32 (Steichen et al., 2008 J Inf Dis 198(12), 1856-1861) or the MC58¢3 msr::kan mutant using pComPind (Ieva et al., 2005, J Bacteriol 187(10), 3421-3430).

MsrA/B Protein Expression

The msr gene was amplified from *N. gonorrhoeae* 1291 using primers msrexp_NdeIF (5'-AAAATCCATAT-GAAAGGGACCGCGACCGTGCCGCA-3'; SEQ ID NO:20) and msrexp_XhoIR (5'-CCCTGACTCGAGTTAT-TCACTTTGCCCTTC-3'; SEQ ID NO:21) and the resulting PCR product was cloned into pET15b to obtain a Msr expression construct pET15bmsr. The construct pET15bmsr was transformed into *E. coli* BL21 Star (DE3)pLysS host strain (Novagen) and MsrA/B was overexpressed and purified. Briefly, expression was induced by 0.1 mM IPTG at an optical density at 600 nm ($OD_{600}$) of 0.4 for 24 hr at room temperature. Cell cultures were harvested and the cell pellet was re-suspended in buffer A. Cells were lysed by sonication, centrifuged and the supernatant was applied to a column packed with TALON™ metal affinity resins (Clontech laboratories, Inc). Unbound proteins were washed away with 20 column volumes of buffer A, followed by 10 column volumes of buffer A with 20 mM imidazole. The MsrA/B protein was eluted in fractions of 1 ml of 200 mM imidazole. Fractions were collected and analyzed by 4-12% NuPAGE® Novex Bis-Tris Gels (Invitrogen) stained with Coomassie Blue, and by Western blot of anti-His polyclonal antisera.

The recombinantly expressed MsrA/B lacked amino acids 1-29 of the full length MsrA/B polypeptide, i.e., the majority of the putative signal sequence. Thus, the recombinantly expressed MsrA/B contained amino acids 30-522 of SEQ ID NO: 1. Fused to the N-terminus of the polypeptide was a 6-His tag and thrombin cleavage site, sequences provided by the pET15 vector. The amino acid sequence of the recombinantly expressed MsrA/B, and the encoding nucleic acid sequence, are shown below.

Amino acid sequence of recombinantly-expressed MsrA/B (N-terminal region containing the 6-His tag and thrombin cleavage site in bold):

(SEQ ID NO: 15)
MGSSHHHHHHSSGLVPRGSHMKGTATVPHTLSTLKTADNRPASVYLKKDK

PTLIKFWASWCPLCLSELGQAEKWAQDAKFSSANLITVASPGFLHEKKDG

EFQKWYAGLNYPKLPVVTDNGGTIAQNLNISVYPSWALIGKDGDVQRIVK

GSINEAQALALIRNPNADLGSLKHSFYKPDTQKKDSAIMNTRTIYLAGGC

FWGLEAYFQRIDGVVDAVSGYANGNTENPSYEDVSYRHTGHAETVKVTYD

ADKLSLDDILQYYFRVVDPTSLNKQGNDTGTQYRSGVYYTDPAEKAVIAA

ALKREQQKYQLPLVVENEPLKNFYDAEEYHQDYLIKNPNGYCHIDIRKAD

EPLPGKTKAAPQGKGFDAATYKKPSDAELKRTLTEEQYQVTQNSATEYAF

SHEYDHLFKPGIYVDVVSGEPLFSSADKYDSGCGWPSFTRPIDAKSVTEH

DDFSFNMRRTEVRSRAADSHLGHVFPDGPRDKGGLRYCINGASLKFIPLE

QMDAAGYGALKGKVK

Amino acid sequence of recombinantly-expressed MsrA/B with 6-His tag removed via thrombin cleavage (residual cleavage site and linker amino acids in bold):

(SEQ ID NO: 39)
GSHMKGTATVPHTLSTLKTADNRPASVYLKKDKPTLIKFWASWCPLCL

SELGQAEKWAQDAKFSSANLITVASPGFLHEKKDGEFQKWYAGLNYPKLP

VVTDNGGTIAQNLNISVYPSWALIGKDGDVQRIVKGSINEAQALALIRNP

NADLGSLKHSFYKPDTQKKDSAIMNTRTIYLAGGCFWGLEAYFQRIDGVV

DAVSGYANGNTENPSYEDVSYRHTGHAETVKVTYDADKLSLDDILQYYFR

VVDPTSLNKQGNDTGTQYRSGVYYTDPAEKAVIAAALKREQQKYQLPLVV

ENEPLKNFYDAEEYHQDYLIKNPNGYCHIDIRKADEPLPGKTKAAPQGKG

FDAATYKKPSDAELKRTLTEEQYQVTQNSATEYAFSHEYDHLFKPGIYVD

VVSGEPLFSSADKYDSGCGWPSFTRPIDAKSVTEHDDFSFNMRRTEVRSR

AADSHLGHVFPDGPRDKGGLRYCINGASLKFIPLEQMDAAGYGALKGKVK

Nucleic acid sequence encoding the recombinantly-expressed MsrA/B (N-terminal region containing the 6-His tag and thrombin cleavage site in bold):

(SEQ ID NO: 16)
ATGGGCAGCAGCCATCATCATCATCATCACAGCAGCGGCCTGGTGCCGCG

CGGCAGCCATATGAAAGGGACCGCGACCGTGCCGCACACTTTATCCACGT

TAAAAACCGCGGACAACCGCCCCGCCAGTGTTTATTTGAAAAAAGACAAA

CCGACGCTGATTAAATTTTGGGCGAGCTGGTGTCCTTTATGTTTGTCCGA

ATTGGGACAGGCCGAGAAATGGGCGCAAGATGCAAAATTCAGCTCCGCCA

ACCTGATTACCGTCGCCTCCCCCGGCTTTTTGCACGAGAAAAAGACGGC

GAGTTTCAAAAATGGTATGCCGGTTTGAACTACCCCAAGCTGCCCGTCGT

TACCGACAACGGCGGCACGATCGCCCAAAACCTGAATATCAGCGTTTATC

CTTCTTGGGCGTTAATCGGTAAAGACGGCGACGTGCAGCGCATCGTCAAA

GGCAGCATCAACGAAGCGCAGGCATTGGCGTTAATCCGCAACCCGAATGC

CGATTTGGGCAGTTTGAAACATTCGTTCTACAAACCCGACACTCAGAAAA

AGGATTCAGCAATCATGAACACGCGCACCATCTACCTCGCCGGCGGCTGC

TTCTGGGGCTTGGAAGCCTATTTCCAACGCATCGACGGCGTGGTTGACGC

GGTATCCGGCTACGCCAACGGCAACACGGAAAACCCGAGCTACGAAGACG

TGTCCTACCGCCATACGGGCCATGCCGAGACCGTCAAAGTGACCTACGAT

GCCGACAAACTCAGCCTGGACGACATCCTGCAATATTATTTCCGCGTCGT

TGATCCGACCAGCCTCAACAAACAGGGTAACGACACCGGCACGCAATACC

GCAGCGGCGTGTACTACACCGACCCCGCCGAAAAAGCCGTCATCGCCGCC

GCCCTCAAACGCGAGCAGCAAAAATACCAACTGCCCCTCGTTGTTGAAAA

CGAACCGCTGAAAAACTTCTACGACGCCGAGGAATACCATCAGGACTACC

TGATTAAAAACCCCAACGGCTACTGCCACATCGACATCCGCAAAGCCGAC

GAACCGCTGCCGGGCAAAACCAAAGCCGCACCGCAAGGCAAAGGCTTCGA

CGCGGCAACGTATAAAAAACCGAGTGACGCCGAACTCAAACGCACCCTGA

CCGAAGAGCAATACCAAGTGACCCAAAACAGCGCGACCGAATACGCCTTC

AGCCACGAATACGACCATTTGTTCAAACCCGGCATTTATGTGGACGTTGT

CAGCGGCGAACCCCTGTTCAGCTCCGCCGACAAATATGATTCCGGCTGCG

GCTGGCCGAGCTTCACGCGCCCGATTGATGCAAAATCCGTTACCGAACAC

GATGATTTCAGCTTCAATATGCGCCGCACCGAAGTCAGAAGCCGCGCCGC

CGATTCGCACTTGGGACACGTCTTCCCCGACGGCCCCCGCGACAAAGGCG

GACTGCGCTACTGCATCAACGGCGCGAGCTTGAAATTCATCCCGCTGGAA

CAAATGGACGCGGCAGGCTACGGCGCGTTGAAGGGCAAAGTGAAATAA

MsrA/B Mouse Antisera Production (Anti-MsrA/B)

Groups of 10 female BALB/c mice (6 weeks old) were immunized subcutaneously with 5 μg of recombinant MsrA/B with either Alhydrogel® (aluminium hydroxide, InvivoGen) or Freund's (FCA/FIA, Sigma-Aldrich) adjuvant on days 0, 21, and 28. Terminal bleeds were collected on day 42. For Freund's adjuvant, Freund's complete adjuvant (FCA) was used on day 0 and Freund's incomplete adjuvant (FIA) was used in the boosts of day 21 and 28. Pre-bleed of each mouse was collected 4 days before immunization. This study was carried out in accordance with the recommendations of the Australian Code for the Care and Use of Animals for Scientific Purposes, the Griffith University Animal Ethics Committee (AEC). The protocol was approved by the Griffith University AEC.

Cell Surface Trypsin Digestion

Overnight culture of 1291 and MC58¢3 were inoculated into appropriate media at an $OD_{600}$ of 0.05. After 2 hr growth in 37° C., cells were harvested, washed once and resuspended in PBS to an $OD_{600}$ of 2. Cell suspension (200 μl) were treated with trypsin (trypsin gold, Promega) for 60 mins at 37° C. Cell suspensions at time 0 and at 60 min were taken in triplicate for the determination of colony forming units (CFUs)/ml to confirm cell viability, and were analyzed by Western blot analysis with anti-MsrA/B. Control antibodies used were to surface exposed PorA (NIBSC-UK-EN63QFG) and cytoplasmic GNA2091 (Seib et al., 2010, Vaccine 28(12), 2416-2427; Bos et al., 2014, J Biol Chem 289(22), 15602-15610).

ELISA

For whole cell ELISA, bacteria were grown on BHI or GC plates for 16 hr. Cells were harvested and resuspended in PBS at an $OD_{600}$ of 0.2. Microtitre plate wells were filled with 50 μl of the bacterial suspension and dried at room temperature overnight in the laminar flow cabinet. The bacteria in the dried wells were then heat-killed for 1 hr in 56° C. For recombinant protein ELISA, wells of plates were coated with 100 ng of purified recombinant MsrA/B protein in 100 µl of coating buffer (0.5M carbonate/bicarbonate buffer, pH 9.6) for 1 hr at room temperature. All ELISAs were performed with mouse pre-immune or MsrA/B immunized sera, and secondary antibody as specified in the results (polyclonal anti-mouse Ig HRP (Dako) or IgG1, IgG2a, IgG2b, IgG3 or IgM HRP (Thermofisher Scientific)). The substrate TMB (3,3', 5,5;-tetramethylbenzidine) solution (Thermofisher Scientific) was used as per manufacture's instruction. Equal amount of 1 N hydrochloric acid was added to stop the reaction. Absorbance was read in a TECAN Model Infinite 200 Pro plate reader at 450 nm.

Serum Bactericidal Assay

N. gonorrhoeae 1291 (~1×10³ CFU) was incubated in serial dilutions of heat-inactivated (56° C., 60 min) anti-MsrA/B sera or pre-immune sera for 15 min at 37° C., after which normal human serum (pre-absorbed with N. gonorrhoeae as described previously (McQuillen et al. 1994, Methods Enzymol 236, 137-147) was added to final concentration of 10% (v/v) as a source of complement. The suspension was then incubated at 37° C., 5% C02 for 30 min and bacterial CFU determined by plating out serial dilutions. The bactericidal titre is the reciprocal of the lowest antibody dilution which induced more than 50% killing after 30 min. Statistical significance was calculated using one-way analysis of variance (ANOVA), Student's t-test and Wilcoxon Signed-Rank Test.

Whole blood from healthy volunteers was collected by venipuncture. For serum, blood was collected in Vacuette Z serum separator tubes (Greiner Bio-One), allowed to clot for 15 min at room temperature then centrifuged for 10 min at 2,000×g. This study was carried out in accordance with the recommendations of the National Statement on Ethical Conduct in Human Research, the Griffith University Human Research Ethics Committee, with written informed consent from all subjects. All subjects gave written informed consent in accordance with the Declaration of Helsinki. The protocol was approved by the Griffith University Human Research Ethics Committee.

Opsonophagocytic Killing Assay

Polymorphonuclear leukocytes (PMNs) were isolated from donor blood (collected in K3 EDTA tubes (Greiner Bio-One)) using Polymorphprep™ (Axis-Shield) as per manufacturer's instructions, and were resuspended in assay buffer (RPMI (Gibco) supplemented with 0.15 mM $CaCl_2$), 0.5 mM $MgCl_2$ and 0.5% (v/v) human serum albumin). N. gonorrhoeae 1291 (~1×10³ CFU) was incubated in serial-dilutions of heat-inactivated anti-MsrA/B sera or pre-immune mouse sera for 15 min at 37° C. PMNs (~1×10⁵ cells) and a complement source (10% v/v normal human serum pre-absorbed with N. gonorrhoeae) were then added, and incubated at 37° C. for 90 min. Gonococcal survival was determined after plating of serial dilutions on GC agar, and survival calculated as a percentage relative to no-antibody control. The opsonophagocytic titre is the reciprocal of the lowest antibody dilution which induced more than 50% killing after 90 min. Statistical significance was calculated using one-way analysis of variance (ANOVA), Student's t-test and Wilcoxon Signed-Rank Test.

Surface Plasmon Resonance (SPR)

SPR assays were performed using a Biacore T200 for affinity analysis and a Pall Pioneer FE for competition assays. Affinity assays were performed as previously described (Semchenko et al. 2017, Infect Immun 85(2) e00898-16). Briefly, MsrA/B was immobilized onto flow cell 2 of a Series S CM5 sensor chip using amine coupling kit (GE Life Sciences) at a flow rate of 5 µL/min for 10 minutes. Flow cell 1 was used as the reference cell and immobilized with ethanolamine only. Met(O) was run at a final concentration range of 0.16 to 100 nM using single cycle kinetics. Data was analyzed using the Biacore T200 evaluation software package. For competition analysis MsrA/B was immobilized onto flow cell 1 of a COOH5 Biosensor chip and flow cell 2 the blank immobilized surface using amine coupling using EDC-NHS reactions. Briefly, EDC-NHS mix was flowed at 10 µL/min for 10 min across flow cell 1 and 2. MsrA/B was then flowed across flow cell 1 at 5 µL/min for 20 min in sodium acetate pH 4.5 at a concentration of 25 µg/mL. Ethanolamine was then flowed at 10 µL/min for 10 min to block any remaining active NHS. Competition assays were performed using NextStep injections in the OneStep assay builder. Pre- and post-immune MsrA/B mouse sera were used as the first injection (A), and Met(O) as the second injection (B), with PBS used as a negative control. The competition injection was run for 60 sec with the A starting at a 1:100 dilution of serum at time zero and reducing across the injection time, with the B component increasing across the injection reaching 10 µM at 60 sec. Binding of Met(O) to MsrA/B was compared with and without serum, and with pre- and post-immune serum. Data was collected using the Pioneer Software package and analyzed using Qdat analysis software. The percentage blocking was calculated based on the relative RMax of the Met(O) injection with and without serum, and the serum with and without Met(O).

Example 2

Assessment of the Distribution and Conservation of MSRA/B

To investigate the distribution and conservation of MsrA/B in N. gonorrhoeae strains, a BLAST search was performed with MsrA/B from N. gonorrhoeae 1291 (SEQ ID NO: 1; GenBank Accession No. EEH61172.1) against available genomes. Analysis of N. gonorrhoeae genome strains in GenBank revealed that MsrA/B is highly conserved, being present in 100% of 468 strains, with 99-100% amino acid identity over the length of the 522 amino acid protein. There are 35 unique gonococcal MsrA/B sequences in the PubMLST database, with 97.5-100% identity between them. There are four main variants that are present in 98% of strains, represented by strains PID322 (54% of strains; SEQ ID NO:9), WHO_K (20%; SEQ ID NO:10), 1291 (19%; SEQ ID NO:1), and MS-11 (5%; SEQ ID NO:11). The N. gonorrhoeae 1291 MsrA/B sequence is 98% identical to MsrA/B of N. meningitidis MC58 (SEQ ID NO: 12).

Thus, MsrA/B is highly conserved in N. gonorrhoeae, with >97% amino acid identity in all strains investigated. Overall, only two sites had common variations: Thr31 substitution to Ala31 in ~75% of isolates, and Lys520 substitution to Glu520 in ~25% of isolates. Residue 31 is in the predicted signal peptide of MsrA/B. This is shown below in the sequences of strains 1291, PID322, WHO_K and MS-11, where the residues at positions 31 and 520 are in bold and underlined. None of the other variant amino acid residues are located in any known catalytic domains identified in N. meningitidis MsrA/B. The MsrA/B polypeptide from N. meningitidis MC58 shares about 98% sequence identity to the MsrA/B polypeptide from N. gonorrhoeae 1291.

N. gonorrhoeae strain 1291 (SEQ ID NO: 1):
MKHRTFFSLCAKFGCLLALGACSPKIVDAGTATVPHTLSTLKTADNRPAS

VYLKKDKPTLIKFWASWCPLCLSELGQAEKWAQDAKFSSANLITVASPGF

LHEKKDGEFQKWYAGLNYPKLPVVTDNGGTIAQNLNISVYPSWALIGKDG

DVQRIVKGSINEAQALALIRNPNADLGSLKHSFYKPDTQKKDSAIMNTRT

IYLAGGCFWGLEAYFQRIDGVVDAVSGYANGNTENPSYEDVSYRHTGHAE

TVKVTYDADKLSLDDILQYYFRVVDPTSLNKQGNDTGTQYRSGVYYTDPA

EKAVIAAALKREQQKYQLPLVVENEPLKNFYDAEEYHQDYLIKNPNGYCH

IDIRKADEPLPGKTKAAPQGKGFDAATYKKPSDAELKRTLTEEQYQVTQN

SATEYAFSHEYDHLFKPGIYVDVVSGEPLFSSADKYDSGCGWPSFTRPID

AKSVTEHDDFSFNMRRTEVRSRAADSHLGHVFPDGPRDKGGLRYCINGAS

LKFIPLEQMDAAGYGALKGKVK

N. gonorrhoeae strain PID322 (SEQ ID NO: 9):
MKHRTFFSLCAKFGCLLALGACSPKIVDAGAATVPHTLSTLKTADNRPAS

VYLKKDKPTLIKFWASWCPLCLSELGQAEKWAQDAKFSSANLITVASPGF

LHEKKDGEFQKWYAGLNYPKLPVVTDNGGTIAQNLNISVYPSWALIGKDG

DVQRIVKGSINEAQALALIRNPNADLGSLKHSFYKPDTQKKDSAIMNTRT

IYLAGGCFWGLEAYFQRIDGVVDAVSGYANGNTENPSYEDVSYRHTGHAE

TVKVTYDADKLSLDDILQYYFRVVDPTSLNKQGNDTGTQYRSGVYYTDPA

EKAVIAAALKREQQKYQLPLVVENEPLKNFYDAEEYHQDYLIKNPNGYCH

IDIRKADEPLPGKTKAAPQGKGFDAATYKKPSDAELKRTLTEEQYQVTQN

SATEYAFSHEYDHLFKPGIYVDVVSGEPLFSSADKYDSGCGWPSFTRPID

AKSVTEHDDFSFNMRRTEVRSRAADSHLGHVFPDGPRDKGGLRYCINGAS

LKFIPLEQMDAAGYGALKGKVK

N. gonorrhoeae strain WHO_K (SEQ ID NO: 10):
MKHRTFFSLCAKFGCLLALGACSPKIVDAGAATVPHTLSTLKTADNRPAS

VYLKKDKPTLIKFWASWCPLCLSELGQAEKWAQDAKFSSANLITVASPGF

LHEKKDGEFQKWYAGLNYPKLPVVTDNGGTIAQNLNISVYPSWALIGKDG

DVQRIVKGSINEAQALALIRNPNADLGSLKHSFYKPDTQKKDSAIMNTRT

IYLAGGCFWGLEAYFQRIDGVVDAVSGYANGNTENPSYEDVSYRHTGHAE

TVKVTYDADKLSLDDILQYFRVVDPTSLNKQGNDTGTQYRSGVYYTDPA

EKAVIAAALKREQQKYQLPLVVENEPLKNFYDAEEYHQDYLIKNPNGYCH

IDIRKADEPLPGKTKAAPQGKGFDAATYKKPSDAELKRTLTEEQYQVTQN

SATEYAFSHEYDHLFKPGIYVDVVSGEPLFSSADKYDSGCGWPSFTRPID

AKSVTEHDDFSFNMRRTEVRSRAADSHLGHVFPDGPRDKGGLRYCINGAS

LKFIPLEQMDAAGYGALKGEVK

N. gonorrhoeae strain MS-11 (SEQ ID NO: 11):
MKHRTFFSLCAKFGCLLALGACSPKIVDAGTATVPHTLSTLKTADNRPAS

VYLKKDKPTLIKFWASWCPLCLSELGQAEKWAQDAKFSSANLITVASPGF

LHEKKDGEFQKWYAGLNYPKLPVVTDNGGTIAQNLNISVYPSWALIGKDG

DVQRIVKGSINEAQALALIRNPNADLGSLKHSFYKPDTQKKDSAIMNTRT

IYLAGGCFWGLEAYFQRIDGVVDAVSGYANGNTENPSYEDVSYRHTGHAE

TVKVTYDADKLSLDDILQYYFRVVDPTSLNKQGNDTGTQYRSGVYYTDPA

EKAVIAAALKREQQKYQLPLVVENEPLKNFYDAEEYHQDYLIKNPNGYCH

IDIRKADEPLPGKTKAAPQGKGFDAATYKKPSDAELKRTLTEEQYQVTQN

SATEYAFSHEYDHLFKPGIYVDVVSGEPLFSSADKYDSGCGWPSFTRPID

AKSVTEHDDFSFNMRRTEVRSRAADSHLGHVFPDGPRDKGGLRYCINGAS

LKFIPLEQMDAAGYGALKGEVK

N. meningitidis strain MC58 (SEQ ID NO: 12):
MKHRTFFSLCAKFGCLLALGACSPKIVDAGAATVPHTLSTLKTADNRPAS

VYLKKDKPTLIKFWASWCPLCLSELGQTEKWAQDAKFSSANLITVASPGF

LHEKKDGDFQKWYAGLNYPKLPVVTDNGGTIAQSLNISVYPSWALIGKDS

DVQRIVKGSINEAQALALIRDPNADLGSLKHSFYKPDTQKKDSKIMNTRT

IYLAGGCFWGLEAYFQRIDGVVDAVSGYANGNTKNPSYEDVSYRHTGHAE

TVKVTYDADKLSLDDILQYFFRVVDPTSLNKQGNDTGTQYRSGVYYTDPA

EKAVIAAALKREQQKYQLPLVVENEPLKNFYDAEEYHQDYLIKNPNGYCH

IDIRKADEPLPGKTKTAPQGKGFDAATYKKPSDAELKRTLTEEQYQVTQN

SATEYAFSHEYDHLFKPGIYVDVVSGEPLFSSADKYDSGCGWPSFTRPID

AKSVTEHDDFSYNMRRTEVRSHAADSHLGHVFPDGPRDKGGLRYCINGAS

LKFIPLEQMDAAGYGALKGKVK

Example 3

Localization of MSRA/B

N. gonorrhoeae MsrA/B was proposed to be an outer membrane protein based on cell fractionation experiments (Skaar et al., 2002, Proc Natl Acad Sci USA 99(15), 10108-10113), however the orientation of MsrA/B in the outer membrane was not determined. Studies to further elucidate the localization of MsrA/B were therefore performed.

Topology prediction analysis using TMHMM (Krogh et al., 2001, J Mol Biol 305(3), 567-580) was performed, and indicated that that MsrA/B does not have any transmembrane domains and that the whole protein is located outside of the membrane (data not shown). To directly investigate if MsrA/B is surface exposed, whole cell ELISAs of N. gonorrhoeae 1291 and N. meningitidis MC58¢3 wild-type and msr::kan mutant strains were performed with mouse antisera raised against recombinant MsrA/B.

Whole cell ELISA indicated that anti-MsrA/B bound to the wild-type 1291 and MC58¢3 intact cells (titre of 256,000 and 512,000, respectively), but binding was significantly reduced to the mutant strains (titre of 8,000 and 1,000, respectively) (FIG. 1A). In addition, MsrA/B was completely susceptible to digestion when intact bacterial cells were treated with 10 or 20 μg of trypsin for 60 min, similar to the meningococcal surface protein PorA (FIG. 1B). The intracellular protein GNA2091 was not affected by trypsin treatment. This ELISA and Western blot data confirmed that MsrA/B is on the surface of both N. gonorrhoeae and N. meningitidis. Trypsin treatment did not affect cell viability, as there was no significant difference in CFU counts between pre- and post-trypsin treatment (data not shown).

Example 4

Immunogenicity of MSRA/B

Figure 2:
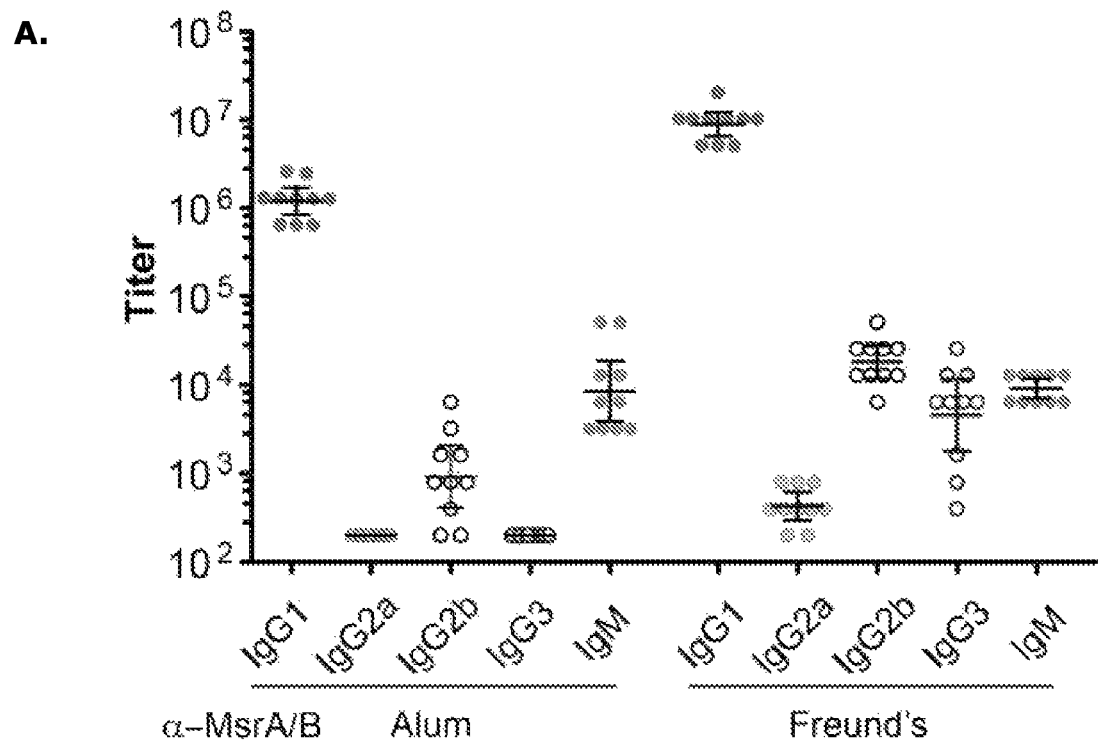
FIG. 2 is a graphical representation showing the immunogenicity of MsrA/B. The titres of the post-immune sera from each mouse immunized with either MsrA/B-Alum or MsrA/B-Freund's were determined by ELISA against (A) purified recombinant MsrA/B for IgG1, G2a, G2b, G3, IgM, or (B) whole cell *N. gonorrhoeae* 1291 wild type (WT), msr::kan mutant (Δmsr), and complemented (Δmsr_C) strains for IgG. The titre for each of 10 mice are shown with circles, and the geometric mean titre (GMT) and 95% Confidence interval are indicated bars. The titres of pre-immune sera against whole cell *N. gonorrhoeae* 1291 strains were ≤200. Mann-Whitney U test for α-MsrA/B-Alum vs α-MsrA/B-Freund's binding to WT (p=0.52); α-MsrA/B-Alum or α-MsrA/B-Freund's binding to WT vs Δmsr_C (p=0.0002).
Figure 2:
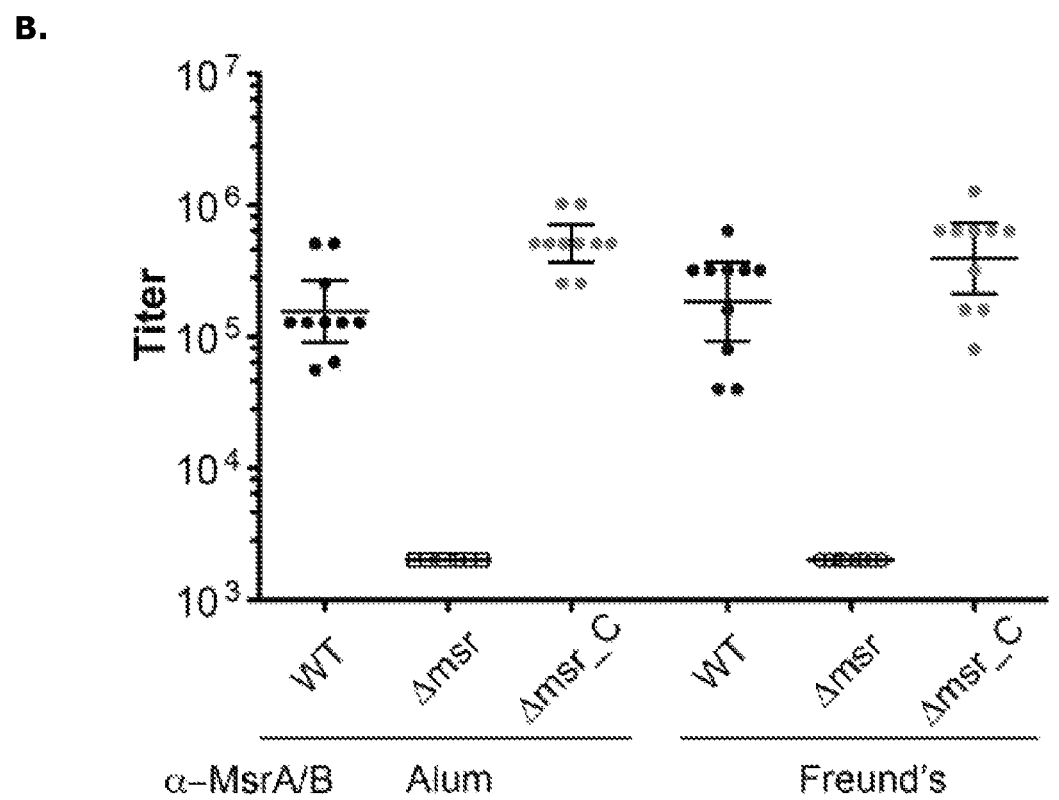

To investigate the immunogenicity of MsrA/B, ten mice were immunized with recombinant MsrA/B with either aluminium hydroxide (MsrA/B-Alum) or Freund's adjuvant (MsrA/B-Freund's). The sera were assessed by ELISA and Western blot. ELISA results with recombinant MsrA/B indicate a dominant IgG1 response in mice immunized with MsrA/B and either adjuvant, with a geometric mean titre (GMT) of 1,222,945 for MsrA/B-Alum and 8,914,438 for MsrA/B-Freund's (FIG. 2A). Higher titres of IgG2a, IgG2b and IgG3 were detected in mice immunized MsrA/B-Freund's compared to MsrA/B-Alum, while IgM titres were similar for both adjuvants (FIG. 2A, Tables 4 and 5).

Whole cell ELISA of the *N. gonorrhoeae* 1291 wild-type, 1291msr::kan mutant, and complemented strains indicated that the MsrA/B antisera from each mouse was able to recognize the native MsrA/B protein on the bacterial surface (FIG. 2B, Tables 4 and 5). There was a similar response against the wild-type from mice immunized with either adjuvant (GMT of 155,496 for MsrA/B-Alum, 183,792 for MsrA/B-Freund's (p=0.52)) and a significantly reduced response to the msr::kan mutant strain (GMT of 2,000 for both adjuvant, p<0.001 vs. wild-type). Analysis of MsrA/B-antisera by Western blotting against whole cell lysates of *N. gonorrhoeae* wild-type and the msr::kan mutant confirmed that MsrA/B antisera specifically recognize MsrA/B. There was no reactivity against MsrA/B in pre-immune sera, while an antibody response was generated by all mice that specifically recognizes MsrA/B in the wild-type strain (Tables 4 and 5).

Figure 3:
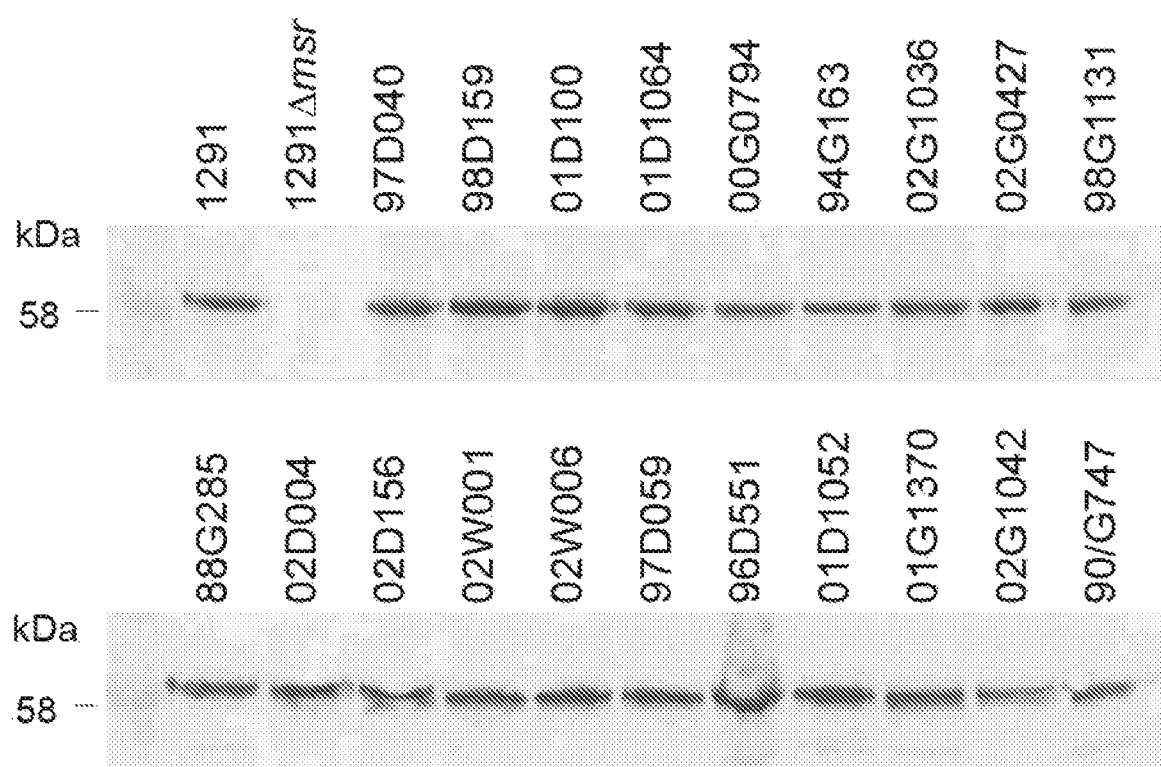
FIG. 3 is a photographic representation showing expression of MsrA/B in a panel of gonococcal strains. Western blot analysis was performed of MsrA/B expression in a panel of *N. gonorrhoeae* strains, including the 1291 wild type and msr::kan mutant (1291Δmsr), and twenty clinical isolates (Power et al, 2007, Infect Immun, 75(6), 3202-4) from mucosal and disseminated gonococcal infections.

This ELISA and Western data confirm that MsrA/B is immunogenic and that anti-MsrA/B antisera can specifically recognize MsrA/B on the surface of *N. gonorrhoeae*. The expression of MsrA/B and the cross-reactivity of the MsrA/B antisera was confirmed by Western blot analysis of twenty clinical isolates from mucosal and disseminated gonococcal infections (FIG. 3).

Example 5

Bactericidal and Opsonophagocytic Activity of MSRA/B Antisera

Figure 4:
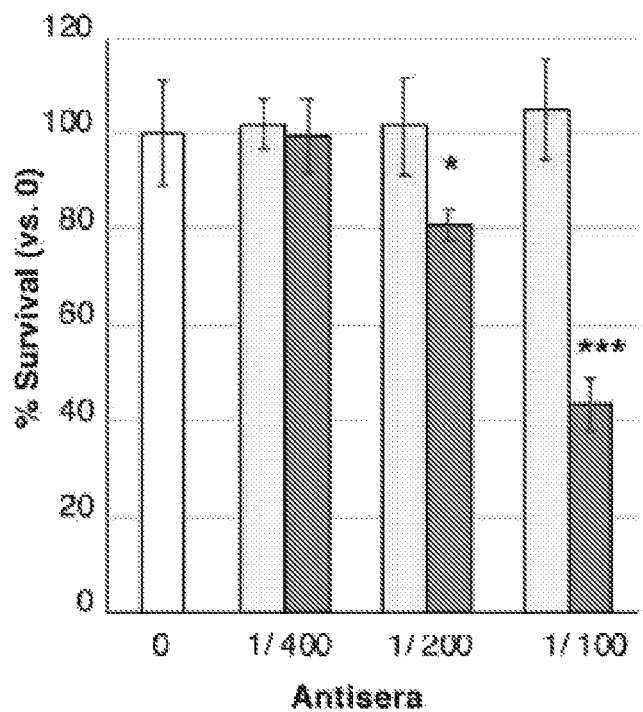
FIG. 4 is a graphical representation showing the functional activity of pooled MsrA/B antisera against *N. gonorrhoeae*. (A) Serum bactericidal activity. The survival of the *N. gonorrhoeae* in the presence of 2-fold dilutions of heat inactivated pre-immune (light grey) or α-MsrA/B (dark grey) sera, plus 10% normal human serum as a complement source is shown. (B) Opsonophagocytic activity. The survival of the *N. gonorrhoeae* in the presence of 2-fold dilutions of heat inactivated pre-immune (light grey) or α-MsrA/B (dark grey) sera, plus primary human polymorphonuclear leukocytes (PMN) and 10% normal human serum as a complement source is shown. For panels A-B, data represent the mean survival (±1 standard deviation) for triplicate samples, as a percentage of bacteria in the absence of antibody (the no antibody control (white) set at 100%, represents $2.0 \times 10^3$ CFU for SBA and $3.5 \times 10^3$ CFU for OPA). (C) Blocking of MsrA/B binding to its substrate methionine sulfoxide (Met(O)). Surface plasmon resonance (SPR) of MsrA/B interaction with Met(O) was performed in the presence of pre-immune (light grey) or α-MsrA/B (dark gray) sera. Data represents the mean MsrA/B-Met(O) binding (±1 standard deviation) for triplicate samples, as a percentage of MsrA/B-Met(O) binding in the absence of antibody (the no antibody control (white) set at 100%, represents a $K_D$ of 15.4±3.7 nM). For panels A-C, statistically significant differences relative to the no serum controls, using a two-tailed Student's t test are indicated: * P<0.05;  P≤0.01; * P≤0.001. For panels A-C, Wilcoxon Signed-Rank Test of activity of sera from individual mice pre vs post immunisation (p<0.01; Table 5).
Figure 4:
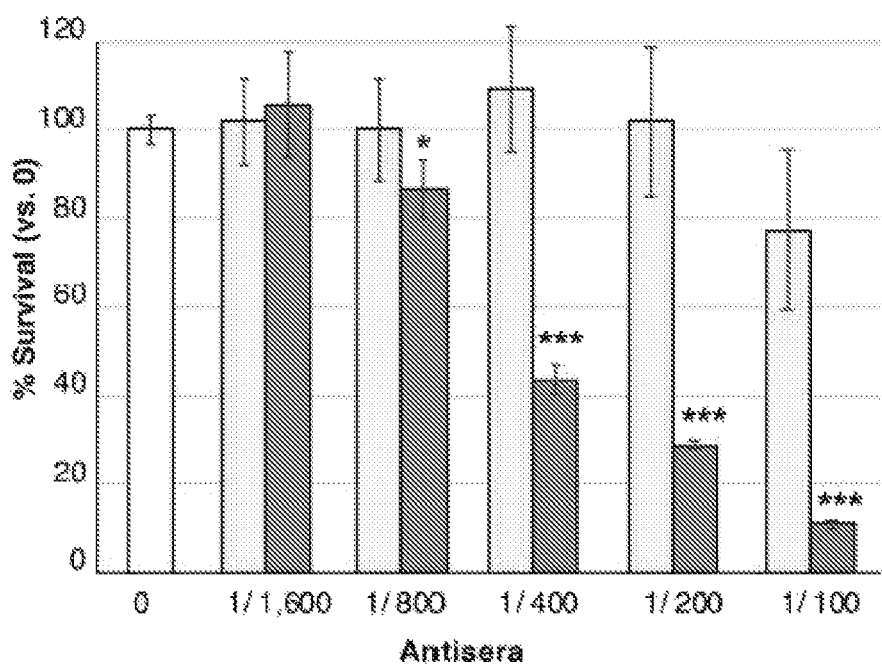
Figure 4:
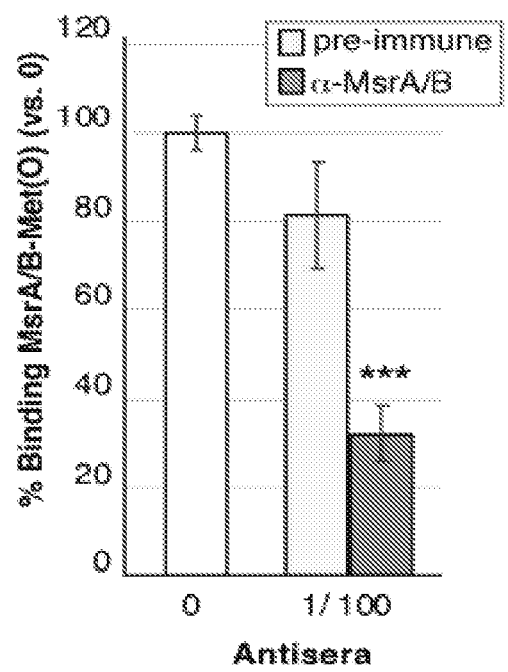

Mouse MsrA/B-Alum and MsrA/B-Freund's antisera were investigated for its ability to elicit serum bactericidal activity (SBA) and opsonophagocytic (OPA) killing of *N. gonorrhoeae*. Incubation of *N. gonorrhoeae* with serial dilutions of pooled MsrA/B antisera and human serum as the complement source, indicated that MsrA/B-Freund's antisera mediated dose-dependent killing, with an SBA titre of 100 (FIG. 4A). SBA analysis of MsrA/B-Freund's sera from the 10 individual mice showed dose-dependent killing for 9/10 mice, and a ≥2 fold increase in SBA titre from pre- to post-immune sera for 9/10 mice (Table 5). Minimal killing was seen for the MsrA/B-Alum serum at the dilutions tested (titre <50; Table 4).

Incubation of *N. gonorrhoeae* with pooled MsrA/B-Freund's antisera, human PMNs and human serum as a complement source, revealed dose-dependent opsonophagocytic killing, with a titre of 400 (FIG. 4B). Analysis of MsrA/B-Freund's serum from the 10 individual mice showed dose-dependent killing, and a 2 fold increase in OPA titre from pre- to post-immune sera for 9/10 mice (Table 5). The MsrA/B-Alum antisera did not mediate any opsonophagocytic killing (Table 4).

Example 6

Effect of MSRA/B Antisera on MSRA/B Binding to Met(O)

To investigate whether MsrA/B antisera was able to block the functional role of MsrA/B, SPR analysis of MsrA/B binding to methionine sulfoxide (Met(O)) was performed in the absence of serum, and in the presence of pre-immune and MsrA/B-Freund's antisera. Recombinant MsrA/B was immobilized on the SPR sensor chip and free Met(O) was flowed over the immobilized protein. MsrA/B bound to Met(O) with a high affinity, with a $K_D$ (equilibrium dissociation constant) of 15.4±3.7 nM (data not shown). A competition assay with pooled MsrA/B-Freund's antisera reduced MsrA/B-Met(O) binding from 100% to 32% (FIG. 4C; p:0.002 vs. no serum or pre-immune sera), while pooled pre-immune sera did not significantly reduce MsrA/B-Met(O) interactions (81±12% binding, p=0.05). Screening of the individual sera showed that 9/10 mice sera significantly blocked MsrA/B-Met(O) binding, compared to no serum and pre-immune serum controls (p<0.05, Table 5), with serum from one mouse blocking >99% of MsrA/B binding to Met(O).

Example 7

Immunisation with MSRA and MSRB Domains

The msrA and msrB domains were amplified from *N. gonorrhoeae* 1291 using primers 15bmsrAFor_NdeI (TTGGGCCATATGAAACATTCGTTCTAC; SEQ ID NO:22) and 15bmsrARev_XhoI (GGCTTTCTCGAGT-TAGCCCGGCAGCGGTTCGT; SEQ ID NO: 23); and 15bmsrBFor_NdeI (GGCAAACATATGAAAGCG-GCAACGTATAAAA; SEQ ID NO:24) and 15bmsr-BRev_XhoI (TGCGGCCTCGAGTTATTTCACTTTGC-CCTTCAA; SEQ ID NO:25), respectively. The resulting PCR products were cloned into pET15b to obtain Msr expression constructs pET15bmsrA and pET15bmsrB. These two constructs were transformed into *E. coli* BL21 Star (DE3)pLysS host strain (Novagen) and MsrA and MsrB were overexpressed and purified. The his-tag of purified MsrA and MsrB protein were removed by Thrombin Clean-Cleave™ kit (Sigma-Aldrich).

The nucleic acid sequence encoding MsrA expressed and purified from pET15bmsrA:

```
                                          (SEQ ID NO: 26)
ATGGGCAGCAGCCATCATCATCATCATCACAGCAGCGGCCTGGTGCCGCG

CGGCAGCCATATGAAACATTCGTTCTACAAACCCGACACTCAGAAAAAGG

ATTCAGCAATCATGAACACGCGCACCATCTACCTCGCCGGCGGCTGCTTC

TGGGGCTTGGAAGCCTATTTCCAACGCATCGACGGCGTGGTTGACGCGGT

ATCCGGCTACGCCAACGGCAACACGGAAAACCCGAGCTACGAAGACGTGT

CCTACCGCCATACGGGCCATGCCGAGACCGTCAAAGTGACCTACGATGCC

GACAAACTCAGCCTGGACGACATCCTGCAATATTATTTCCGCGTCGTTGA

TCCGACCAGCCTCAACAAACAGGGTAACGACACCGGCACGCAATACCGCA

GCGGCGTGTACTACACCGACCCCGCCGAAAAAGCCGTCATCGCCGCCGCC

CTCAAACGCGAGCAGCAAAAATACCAACTGCCCCTCGTTGTTGAAAACGA
```

-continued

ACCGCTGAAAAACTTCTACGACGCCGAGGAATACCATCAGGACTACCTGA

TTAAAAACCCCAACGGCTACTGCCACATCGACATCCGCAAAGCCGACGAA

CCGCTGCCGGGCTAA

The amino acid sequence of MsrA expressed and purified from pET15bmsrA (his-tag region that is removed by thrombin cleavage in bold):

(SEQ ID NO: 27)
MGSSHHHHHHSSGLVPRGSHMKHSFYKPDTQKKDSAIMNTRTIYLAGGCF

WGLEAYFQRIDGVVDAVSGYANGNTENPSYEDVSYRHTGHAETVKVTYDA

DKLSLDDILQYYFRVVDPTSLNKQGNDTGTQYRSGVYYTDPAEKAVIAAA

LKREQQKYQLPLVVENEPLKNFYDAEEYHQDYLIKNPNGYCHIDIRKADE

PLPG

The amino acid sequence of MsrA expressed and purified from pET15bmsrA, with his-tag region by thrombin cleavage:

(SEQ ID NO: 28)
GSHMKHSFYKPDTQKKDSAIMNTRTIYLAGGCFWGLEAYFQRIDGVVDAV

SGYANGNTENPSYEDVSYRHTGHAETVKVTYDADKLSLDDILQYYFRVVD

PTSLNKQGNDTGTQYRSGVYYTDPAEKAVIAAALKREQQKYQLPLVVENE

PLKNFYDAEEYHQDYLIKNPNGYCHIDIRKADEPLPG

The nucleic acid sequence encoding MsrB expressed and purified from pET15bmsrB:

(SEQ ID NO: 29)
ATGGGCAGCAGCCATCATCATCATCATCACAGCAGCGGCCTGGTGCCGCG

CGGCAGCCATATGAAAGCGGCAACGTATAAAAAACCGAGTGACGCCGAAC

TCAAACGCACCCTGACCGAAGAGCAATACCAAGTGACCCAAAACAGCGCG

ACCGAATACGCCTTCAGCCACGAATACGACCATTTGTTCAAACCCGGCAT

TTATGTGGACGTTGTCAGCGGCGAACCCCTGTTCAGCTCCGCCGACAAAT

ATGATTCCGGCTGCGGCTGGCCGAGCTTCACGCGCCCGATTGATGCAAAA

TCCGTTACCGAACACGATGATTTCAGCTTCAATATGCGCCGCACCGAAGT

CAGAAGCCGCGCCGCCGATTCGCACTTGGGACACGTCTTCCCCGACGGCC

CCCGCGACAAAGGCGGACTGCGCTACTGCATCAACGGCGCGAGCTTGAAA

TTCATCCCGCTGGAACAAATGGACGCGGCAGGCTACGGCGCGTTGAAGGG

CAAAGTGAAATAA

The amino acid sequence of MsrB expressed and purified from pET15bmsrB (his-tag region that is removed by thrombin cleavage in bold):

(SEQ ID NO: 30)
MGSSHHHHHHSSGLVPRGSHMKAATYKKPSDAELKRTLTEEQYQVTQNSA

TEYAFSHEYDHLFKPGIYVDVVSGEPLFSSADKYDSGCGWPSFTRPIDAK

SVTEHDDFSFNMRRTEVRSRAADSHLGHVFPDGPRDKGGLRYCINGASLK

FIPLEQMDAAGYGALKGKVK

The amino acid sequence of MsrB expressed and purified from pET15bmsrB, with his-tag region removed by thrombin cleavage:

(SEQ ID NO: 31)
GSHMKAATYKKPSDAELKRTLTEEQYQVTQNSATEYAFSHEYDHLFKPGI

YVDVVSGEPLFSSADKYDSGCGWPSFTRPIDAKSVTEHDDFSFNMRRTEV

RSRAADSHLGHVFPDGPRDKGGLRYCINGASLKFIPLEQMDAAGYGALKG

KVK

Figure 5:
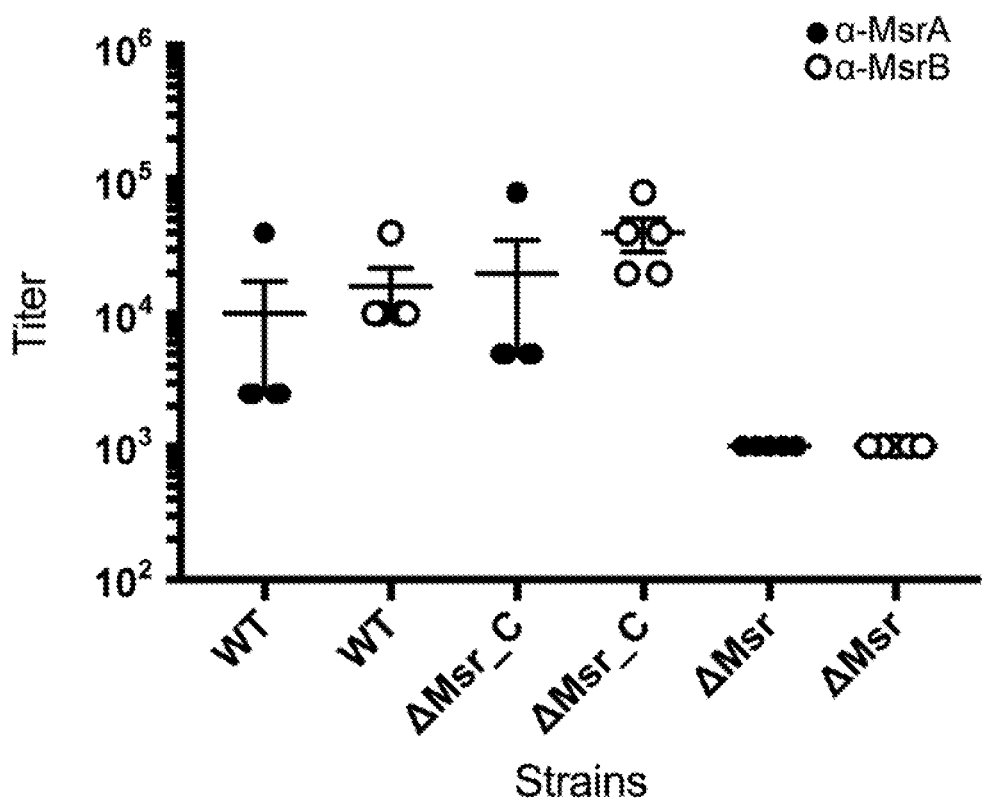
FIG. 5 is a graphical representation showing the immunogenicity of the MsrA and MsrB domains. The titres of the post-immune sera from each mouse immunized with either MsrA and MsrB were determined by ELISA against whole cell *N. gonorrhoeae* 1291 wild type (WT), msr::kan mutant (Δmsr), and complemented (Δmsr_C) strains for IgG. The titre for each of 5 mice are shown. The geometric mean titre (GMT) and 95% Confidence interval are indicated bars. The titres of pre-immune sera against whole cell *N. gonorrhoeae* 1291 strains were ≤200. Mann-Whitney U test for α-MsrA binding to WT vs Δmsr, or α-MsrB binding to WT vs Δmsr (p=0.012); α-MsrA vs α-MsrB binding to WT or Δmsr_C (p=0.12).

To test the immunogenicity of MsrA and MsrB, groups of five mice were immunized with MsrA or MsrB with Freund's adjuvant. The sera were assessed by ELISA and results are shown in FIG. 5. Whole cell ELISA indicates that anti-MsrA and anti-MsrB bound to the wild-type 1291 and 1291 Δmsr_C intact cells. MsrA antisera had an average titre of 10,000 and 20,000 to 1291 and 1291 Δmsr_C, respectively. MsrB antisera had a slightly higher binding titre to 1291 and 1291 Δmsr_C but this difference was not statistically significant (titre of 16,000 and 40,000, respectively). Binding of MsrA and MsrB antisera were significantly reduced to the mutant strains (titre of 1,000 and 1,000, respectively). There was no significant antigenicity difference between MsrA and MsrB. This data demonstrates that each of MsrA and MsrB could be used as an immunogen in a vaccine for *N. gonorrhoeae*.

Example 8

Immunisation with MSRA/B Formulated with OMVS

MsrA/B are formulated with OMVs in the following ways: 1) native *N. gonorrhoeae* OMV plus recombinant MsrA/B, with or without Alum or Freund's; 2) detergent-extracted *N. gonorrhoeae* OMV plus recombinant MsrA/B, with or without Alum or Freund's; 3) native *N. gonorrhoeae* OMV overexpressing MsrA/B, with or without Alum or Freund's; and 4) detergent-extracted *N. gonorrhoeae* OMV overexpressing MsrA/B, with or without Alum or Freund's. Recombinant MsrA/B is formulated with the serogroup B meningococcal vaccine Bexsero®, which contains outer membrane vesicles from a serogroup B strain NZ98/254, formulated with three recombinant proteins: NadA, fHBP and NHBA.

Isolation of Native OMVs

Naturally-secreted native *N. gonorrhoeae* OMVs are isolated as previously described (Semchenko et al. 2017, Infect Immun 85(2)e00898-16). Briefly, native OMV are isolated from a 6-hour culture (GC broth, $OD_{600}$ ~0.8) by brief centrifugation (5,000×g) and subsequent filtration of the supernatant (0.22 μm filter). The filtrate is centrifuged (100,000×g, 1 hour, 4° C.) and the pellet containing OMVs is washed three times with PBS. The pellet is solubilized in PBS containing 0.2% SDS. OMVs are analyzed by SDS-PAGE and protein concentration is measured using the BCA Protein Assay. For native OMVs, the endotoxin activity is attenuated by deletion of the IpxL1 gene.

Isolation of Detergent-Extracted OMVs

Detergent-extracted OMVs are isolated using deoxycholate (DOC) as described previously (Fredriksen et al. 1991, NIPH Ann. 14, 67-79). Briefly, a 6-hour culture is incubated in 0.1 M Tris-HCl, pH 8.6, containing 10 mM EDTA and 0.5% DOC for 30 min at room temperature, then centrifuged (20,000×g; 30 min; 4° C.). The supernatant is ultracentrifuged (125,000×g; 2 hrs; 4° C.) and the OMV pellet resuspended in 50 mM Tris-HCl, pH 8.6, 2 mM EDTA, 1.2%

DOC, 20% sucrose, then subjected to a second round of ultracentrifugation. OMVs are then homogenized in 30% sucrose.

Overexpression of MsrA/B in OMVs

To overexpress MsrA/B in *N. gonorrhoeae*, the full length intact msrA/B gene is introduced into the proB locus in the gonococcal chromosome of the 1291 msr::kan mutant using the complementation construct pCTS32_msr, with msrA/B expression under the control of a strong promoter (e.g. porB promoter). The pCTS32_msr construct used to generate the Δmsr_C complemented strain is modified to incorporate the 100 bp upstream of porB (NC_003112.2 2157429-2157528; CAGACATGGAATCGCCGAAAACGTCGGCGGTA-AATGCAAAGCTAAGCGGCTTGGAAAGCCCG-GCCGGCTTA AATTTCTTAACCAAAAAAGGAATA-CAGCA (SEQ ID NO:32) which will replace 200 bp upstream of msrA/B in the pCTS32_msr construct. Inverse PCR using primers PmeI_For (GTTTAAACAT-GAAACACCGTACTTTCTT; SEQ ID NO:33) and PmeI_Rev (AAAC1T1TGATGTTTCCTGTGTGG; SEQ ID NO:34) is performed to create a restriction site (PmeI) upstream of the msrA/B gene in pCTS32_msr and the resulting PCR is self-ligated to produce pCTS32_msr2. Primers pCTS32_porBPromoter_AflIIFor (AGTTTCCT-TAAGCAGACATGGAATCGCCGAAAACG; SEQ ID NO:35) and pCTS32_porBPromoter_PmeIRev (TTCATTGTTTAAACTGCTGTATTCC11T1TGG; SEQ ID NO:36) are used to amplify 100 bp of upstream porB in *N. meningitidis* strain MC58. The resulting PCR product is digested with restriction enzymes AflII and PmeI and ligated to AflII and PmeI site in pCTS32_msr2. To construct pCTS32_msr, the msrA/B gene and 200 bp upstream was PCR amplified from strain 1291, using primers pCTS32_Msr_AflIIFor (CTCGAGCTTAAGCCGGCGTT-TCCTG1111T1C; SEQ ID NO:37) and pCTS32_Msr_SmaIRev (TGCGGCCCCGGGTTATTTCACTTTGC-CCTTCAACG; SEQ ID NO:38) that generated an AflII site at the 5' end and a SmaI site at the 3' end. The resulting PCR product was cloned into AflII and SmaI-digested pCTS32 to generate pCTS32_msr.

Immunization with MSRA/B Formulated with OMVs

Groups of 10 female BALB/c mice (6 weeks old) are immunized subcutaneously with MsrA/B+OMV (10 μg native or detergent-extracted OMV plus 5 μg of recombinant MsrA/B, or 10 μg OMV overexpressing MsrA/B) in the presence or absence of either Alhydrogel® (aluminium hydroxide, InvivoGen) or Freund's (FCA/FIA, Sigma-Aldrich) adjuvant on days 0, 21, and 28. Terminal bleeds are collected on day 42. Mice are immunised with Bexsero® plus 5 μg of recombinant MsrA/B, in the absence of additional adjuvant. For Freund's adjuvant, Freund's complete adjuvant (FCA) is used on day 0 and Freund's incomplete adjuvant (FIA) is used in the boosts of day 21 and 28. Pre-bleed of each mouse is collected 4 days before immunization.

The level of MsrA/B present in MsrA/B+OMV formulations is assessed as described in Example 1, using anti-MsrA/B sera. The immunogenicity of MsrA/B+OMV formulations, and the activity of MsrA/B+OMV antisera, is assessed as described in Example 1.

TABLE 4

Data for individual and pooled mice sera immunised with MsrA/B-Alum.

| MsrA/B-Alum | ELISA titre vs MsrA/B | | | | | ELISA titre vs whole cells^ | | | SBA titre | | OPA titre | |
|---|---|---|---|---|---|---|---|---|---|---|---|---|
| Mouse | IgG1 | IgG2a | IgG2b | IgG3 | IgM | WT | Δmsr | Δmsr_C | Pre | Post | Pre | Post |
| 1 | 655,360 | 200 | 800 | 200 | 12,800 | 128,000 | 2,000 | 512,000 | — | — | — | — |
| 2 | 2,621,440 | 200 | 3,200 | 200 | 51,200 | 256,000 | 2,000 | 512,000 | — | — | — | — |
| 3 | 1,310,720 | 200 | 800 | 200 | 6,400 | 64,000 | 2,000 | 256,000 | — | — | — | — |
| 4 | 1,310,720 | 200 | 1,600 | 200 | 6,400 | 512,000 | 2,000 | 1,024,000 | — | — | — | — |
| 5 | 655,360 | 200 | 1,600 | 200 | 3,200 | 56,000 | 2,000 | 512,000 | — | — | — | — |
| 6 | 1,310,720 | 200 | 200 | 200 | 3,200 | 128,000 | 2,000 | 512,000 | — | — | — | — |
| 7 | 1,310,720 | 200 | 800 | 200 | 3,200 | 128,000 | 2,000 | 256,000 | — | — | — | — |
| 8 | 1,310,720 | 200 | 6,400 | 200 | 12,800 | 512,000 | 2,000 | 1,024,000 | — | — | — | — |
| 9 | 655,360 | 200 | 400 | 200 | 51,200 | 128,000 | 2,000 | 512,000 | — | — | — | — |
| 10 | 2,621,440 | 200 | 200 | 200 | 3,200 | 128,000 | 2,000 | 512,000 | — | — | — | — |
| GMT | 1,222,945 | 200 | 919 | 200 | 8,445 | 155,496 | 2,000 | 512,000 | — | — | — | — |
| pool | | | | | | | | | <50 | <50 | <50 | <50 |

SBA titre; serum bactericidal titre (reciprocal of the lowest antibody dilution which induced more than 50% killing after 60 min).
OPA titre, opsonophagocytic titre (reciprocal of the lowest antibody dilution which induced more than 50% killing after 90 min).
GMT, geometric mean titre;
—, not determined.
^The titres of pre-immune sera against whole cell *N. gonorrhoeae* 1291 strains were ≤200.

TABLE 5

Data for individual and pooled mice sera immunised with MsrA/B-Freund's.

| MsrA/B Freund's | ELISA titre vs MsrA/B | | | | | ELISA titre vs whole cellscells^ | | | SBA titre* | | OPA titre* | | MsrA/B-Me(O) binding inhibition | |
|---|---|---|---|---|---|---|---|---|---|---|---|---|---|---|
| Mouse | IgG1 | gG2a | gG2b | gG3 | gM | T | msr | msr_C | re | ost | re | ost | re | ost |
| 1 | 10,240,000 | 400 | 51,200 | 25,600 | 12,800 | 320,000 | 2,000 | 640,000 | <50 | 50 | <100 | 200 | 20.5% | 41.9% |
| 2 | 5,120,000 | 800 | 25,600 | 6,400 | 12,800 | 320,000 | 2,000 | 640,000 | <50 | 50 | 100 | 200 | 4.6% | 62.5% |

TABLE 5-continued Data for individual and pooled mice sera immunised with MsrA/B-Freund's.

| MsrA/B Freund's | ELISA titre vs MsrA/B | | | | | ELISA titre vs whole cellscells^ | | | SBA titre* | | OPA titre* | | MsrA/B-Me(O) binding inhibition | |
|---|---|---|---|---|---|---|---|---|---|---|---|---|---|---|
| Mouse | IgG1 | gG2a | gG2b | gG3 | gM | T | msr | msr_C | re | ost | re | ost | re | ost |
| 3 | 10,240,000 | 400 | 25,600 | 6,400 | 6,400 | 320,000 | 2,000 | 640,000 | <50 | 100 | <100 | 200 | 5.7% | 99.7% |
| 4 | 10,240,000 | 800 | 25,600 | 12,800 | 12,800 | 320,000 | 2,000 | 640,000 | <50 | 50 | <100 | 200 | 9.0% | 65.7% |
| 5 | 10,240,000 | 800 | 12,800 | 6,400 | 6,400 | 80,000 | 2,000 | 160,000 | <50 | <50 | <100 | <100 | 6.2% | 12.0% |
| 6 | 20,480,000 | 400 | 12,800 | 1,600 | 6,400 | 40,000 | 2,000 | 160,000 | 50 | 200 | 100 | 800 | 3.2% | 49.0% |
| 7 | 10,240,000 | 200 | 12,800 | 6,400 | 12,800 | 160,000 | 2,000 | 320,000 | <50 | <50 | <100 | 100 | 1.1% | 54.1% |
| 8 | 10,240,000 | 400 | 25,600 | 12,800 | 6,400 | 40,000 | 2,000 | 80,000 | 50 | 100 | 100 | 400 | 6.5% | 54.7% |
| 9 | 5,120,000 | 200 | 12,800 | 800 | 12,800 | 640,000 | 2,000 | 1,280,000 | 50 | 200 | 100 | 400 | 17.2% | 64.9% |
| 10 | 5,120,000 | 400 | 6,400 | 400 | 6,400 | 320,000 | 2,000 | 640,000 | <50 | 50 | <100 | 100 | 0.9% | 55.9% |
| GMT | 8914438 | 429 | 18102 | 4525 | 9051 | 246754 | 2000 | 393966 | 50 | 84 | 55 | 200 | | |
| Mean | | | | | | | | | | | | | 7.5% | 56.0% |
| pool | | | | | | | | | <100 | 100 | <100 | 400 | 18.5% | 67.9% |

SBA titre; serum bactericidal titre (reciprocal of the lowest antibody dilution which induced more than 50% killing after 60 min).
OPA titre, opsonophagocytic titre (reciprocal of the lowest antibody dilution which induced more than 50% killing after 90 min).
GMT, geometric mean titre.
^The titres of pre-immune sera against whole cell *N. gonorrhoeae* 1291 strains was ≤200.
*When a final titre was not reached (i.e., <50 or <100) a value of the next 2-fold dilution (i.e., 25 or 50, respectively) was used to calculate the GMT.
The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

What is claimed is:

1. A method for eliciting an immune response to *N. gonorrhoeae* or *N. meningitidis* in a subject, comprising administering to the subject a composition, comprising:
 a recombinant or synthetic methionine sulfoxide reductase A/B (MsrA/B) polypeptide, or a recombinant or synthetic polynucleotide encoding the MsrA/B polypeptide, and an adjuvant; or
 a viral vector comprising a polynucleotide encoding the MsrA/B polypeptide;
 wherein the MsrA/B polypeptide:
 (a) lacks 1 to 16 amino acids from the N-terminus of a full-length MsrA/B polypeptide, wherein the full-length MsrA/B polypeptide comprises the amino acid sequence set forth in SEQ ID NO:1 or an amino acid sequence having at least 95% sequence identity to the sequence set forth in SEQ ID NO:1; or
 (b) is an antigenic fragment of a polypeptide defined in (a), wherein the antigenic fragment is at least 30 amino acids long.

2. The method of claim 1, wherein the MsrA/B polypeptide comprises amino acids corresponding to amino acids 17-522 of SEQ ID NO:1.

3. The method of claim 1, wherein the antigenic fragment comprises all or a portion of the MsrA domain.

4. The method of claim 1, wherein the antigenic fragment comprises all or a portion of amino acids corresponding to amino acids 181-362 or 199-354 of SEQ ID NO:1.

5. The method of claim 1, wherein the antigenic fragment comprises all or a portion of the MsrB domain.

6. The method of claim 1, wherein the antigenic fragment comprises all or a portion of amino acids corresponding to amino acids 375-522 or 383-506 of SEQ ID NO:1.

7. The method of claim 1, wherein the antigenic fragment comprises all or a portion of the thioredoxin domain.

8. The method of claim 1, wherein the antigenic fragment comprises all or a portion of amino acids corresponding to amino acids 17-174 of SEQ ID NO:1.

9. The method of claim 1, wherein the full-length MsrA/B polypeptide comprising an amino acid sequence having at least 95% sequence identity to the sequence set forth in SEQ ID NO:1 is selected from among SEQ ID NO:9-12.

10. The method of claim 1, wherein the MsrA/B polypeptide is linked to a T helper cell epitope.

11. The method of claim 1, wherein the MsrA/B polypeptide is linked to a carrier protein.

12. The method of claim 10, wherein the carrier protein is selected from among tetanus toxoid, diphtheria toxoid and CRM-197.

13. The method of claim 5, wherein the adjuvant is selected from among an aluminium salt, a water-in-oil emulsion, an oil-in-water emulsion, a toll like receptor (TLR) agonist, a saponin-based adjuvant, a liposome, a virosome, a virus-like particle (VLP), a cytokine, a chemokine and a growth factor.

14. The method of claim 13, wherein the oil-in-water emulsion comprises squalene.

15. The method of claim 13, wherein the saponin-based adjuvant comprises saponins or saponin derivatives from *Quillaja saponaria, Panax ginseng Panax notoginseng, Panax quinquefolium, Platycodon grandiflorum, Polygala senega, Polygala tenuifolia, Quillaja brasiliensis, Astragalus membranaceus* or *Achyranthes bidentate*.

16. The method of claim 13, wherein the saponin-based adjuvant is an iscom or iscom matrix.

17. The method of claim 13, wherein the TLR agonist is a TLR1, TLR2, TLR3, TLR4, TLR5, TLR7, TLR8, TLR9 and/or TLR10 agonist.

18. The method of claim 1, further comprising at least one additional antigen.

19. The method of claim 18, wherein the at least one additional antigen comprises a *N. gonorrhoeae* antigen.

20. The method of claim 19, wherein the *N. gonorrhoeae* antigen is selected from among PilC, PilQ, Opa, AniA, TdfJ, PorB, Lst, TbpB, TbpA, OmpA, OpcA, MetQ, MtrE and the 2C7 epitope or epitope mimetic.

21. The method of claim 18, wherein the at least one additional antigen comprises a *N. meningitidis* antigen.

22. The method of claim 21, wherein the *N. meningitidis* antigen is selected from among NadA, fHbp, NHBA, GNA1030, GNA2091, HmbR, NspA, Nhha, App, Omp85, TbpA, TbpB, Cu,Zn-superoxide dismutase and a capsular polysaccharides or oligosaccharides from meningococcal serogroup A, C, W135 or Y.

23. The method of claim 1, wherein the viral vector is selected from a retrovirus, adenovirus, adeno-associated virus (AAV), herpes virus, alphavirus, astrovirus, coronavirus, orthomyxovirus, papovavirus, paramyxovirus, parvovirus, picornavirus, poxvirus, and togavirus vector.

24. A method for inhibiting the development or progression of a *N. gonorrhoeae* and/or *N. meningitidis* infection in a subject, comprising administering to the subject a composition, comprising:
 a recombinant or synthetic methionine sulfoxide reductase A/B (MsrA/B) polypeptide, or a recombinant or synthetic polynucleotide encoding the MsrA/B polypeptide, and an adjuvant; or
 a viral vector comprising a polynucleotide encoding the MsrA/B polypeptide; wherein the MsrA/B polypeptide:
 (a) lacks 1 to 16 amino acids from the N-terminus of a full-length MsrA/B polypeptide, wherein the full-length MsrA/B polypeptide comprises the amino acid sequence set forth in SEQ ID NO:1 or an amino acid sequence having at least 95% sequence identity to the sequence set forth in SEQ ID NO:1; or
 (b) is an antigenic fragment of a polypeptide defined in (a), wherein the antigenic fragment is at least 30 amino acids long.

25. A method for treating a *N. gonorrhoeae* and/or *N. meningitidis* infection in a subject, comprising administering to the subject a composition, comprising:
 a recombinant or synthetic methionine sulfoxide reductase A/B (MsrA/B) polypeptide, or a recombinant or synthetic polynucleotide encoding the MsrA/B polypeptide, and an adjuvant; or a viral vector comprising a polynucleotide encoding the MsrA/B polypeptide; wherein the MsrA/B polypeptide:
  (a) lacks 1 to 16 amino acids from the N-terminus of a full-length MsrA/B polypeptide, wherein the full-length MsrA/B polypeptide comprises the amino acid sequence set forth in SEQ ID NO:1 or an amino acid sequence having at least 95% sequence identity to the sequence set forth in SEQ ID NO:1; or
  (b) is an antigenic fragment of a polypeptide defined in (a), wherein the antigenic fragment is at least 30 amino acids long.

26. The method of claim 13, wherein the TLR agonist is 3-O-desacyl-4'-monophosphoryl lipid A (MPL), an adjuvant comprising MPL, or an outer membrane vesicle (OMV).

27. The method of claim 26, wherein the OMV is a *N. meningitidis, N. gonorrhoeae, Escherichia coli* or *Pseudomonas aeruginosa* OMV.

* * * * *